United States Patent
Guo

(10) Patent No.: US 9,234,238 B2
(45) Date of Patent: Jan. 12, 2016

(54) MEMBRANE-INTEGRATED VIRAL DNA-PACKAGING MOTOR PROTEIN CONNECTOR BIOSENSOR FOR DNA SEQUENCING AND OTHER USES

(76) Inventor: Peixuan Guo, Mason, OH (US)

( * ) Notice: Subject to any disclaimer, the term of this patent is extended or adjusted under 35 U.S.C. 154(b) by 1110 days.

(21) Appl. No.: 13/094,698

(22) Filed: Apr. 26, 2011

(65) Prior Publication Data

US 2015/0267253 A1    Sep. 24, 2015

Related U.S. Application Data

(63) Continuation-in-part of application No. PCT/US2009/062826, filed on Oct. 30, 2009.

(60) Provisional application No. 61/109,669, filed on Oct. 30, 2008.

(51) Int. Cl.
| | |
|---|---|
| *C12Q 1/68* | (2006.01) |
| *C07K 14/005* | (2006.01) |
| *G01N 33/487* | (2006.01) |
| *G01N 27/447* | (2006.01) |

(52) U.S. Cl.
CPC ............ *C12Q 1/6869* (2013.01); *C07K 14/005* (2013.01); *G01N 27/447* (2013.01); *G01N 33/48721* (2013.01); *C07K 2319/03* (2013.01); *C07K 2319/10* (2013.01); *C07K 2319/21* (2013.01); *C07K 2319/22* (2013.01)

(58) Field of Classification Search
CPC .................................................. C12Q 1/6869
See application file for complete search history.

(56) References Cited

U.S. PATENT DOCUMENTS 6,190,918 B1 * 2/2001 Chu et al. ................ 436/63
2005/0266416 A1   12/2005 Guo

OTHER PUBLICATIONS

Birck Nanotechnology Center (Jan. 3, 2007), downloaded on Apr. 18, 2014 from URL: <http://web.archive.org/web/20070103184716/http://www.vet.purdue.edu/PeixuanGuo/NDC/>.*
Guo et al, Construction and 3-D Computer Modeling of Connector Arrays withT etragonal to Decagonal Transition Induced by pRNA of phi29 DNA-Packaging Motor, Journal of Nanoscience and Nanotechnology, vol. 5, 856-863, 2005.*
Berg et al (Biochemistry, 5th edition, New York: W H Freeman; 2002), downloaded on Apr. 18, 2014 from URL: <http://www.ncbi.nlm.nih.gov/books/NBK22361/>.*
Guasch et al, Detailed Architecture of a DNA Translocating Machine: The High-resolution Structure of the Bacteriophage phi29 Connector Particle, J. Mol. Biol. (2002) 315, 663-676.*
Nature, 2000, vol. 408, pp. 745-750.
ChemBioChem, 2007, vol. 8, pp. 1246-1250.
Nature Nanotech, 2007, vol. 2, pp. 243-238.

* cited by examiner

*Primary Examiner* — Amber D Steele
(74) *Attorney, Agent, or Firm* — Faegre Baker Daniels LLP; Yonghao Hou

(57) ABSTRACT

Compositions and methods are disclosed that exploit the unprecedented modification of double-stranded DNA virus DNA-packaging motor protein connector polypeptides to render them capable of stable incorporation into lipid membranes as a self-assembled homodocamer that forms an aperture through which conductance can occur when an electrical potential is applied across the membrane. The aperture permits use of the modified protein as a biosensor, for dsDNA sequencing, SNP detection and highly sensitive affinity capture and fingerprinting of analytes, and also finds use in electropotential-driven solute translocation, such as for liposomal loading to form therapeutic nanoparticles (e.g., gene delivery) and bioreactors, and for other uses. The aperture can further be used in optical detection of dsDNA or other acceptor labeled analytes in a fluorophore donor labeled single pore channel.

72 Claims, 30 Drawing Sheets

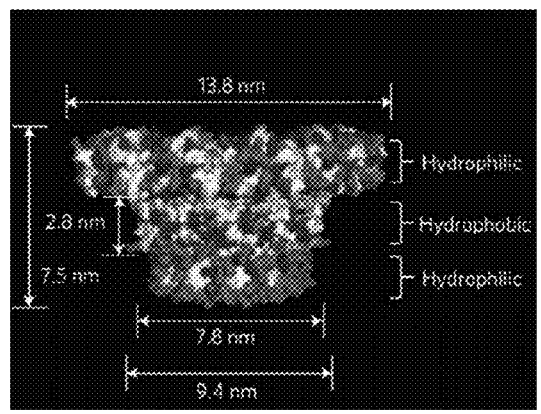 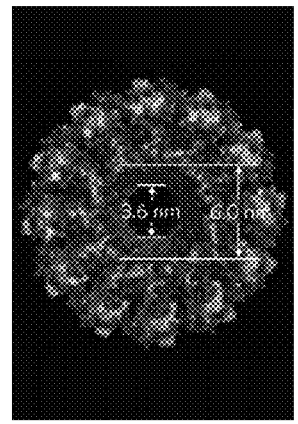
*FIG.1A*  *FIG.1B*
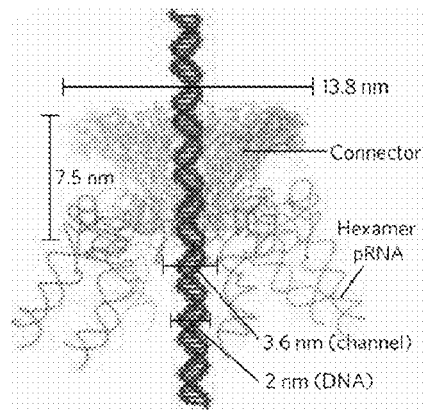 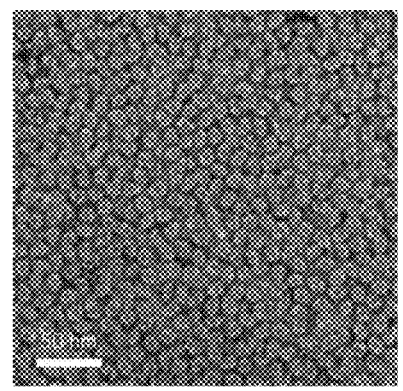
*FIG.1C*  *FIG.1D*
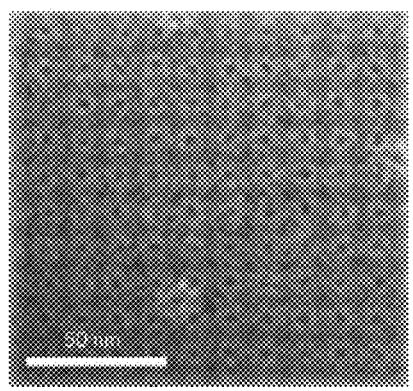 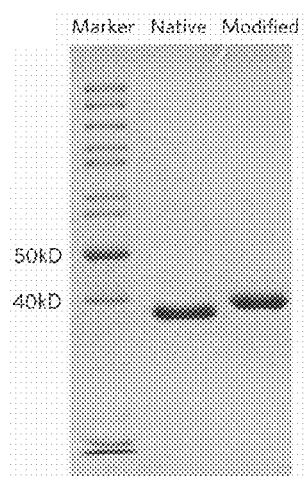
*FIG.1E*  *FIG.1F*

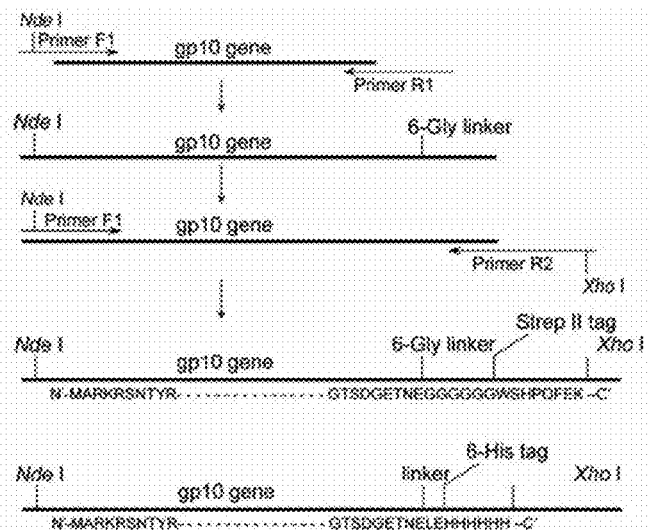
*FIG.2A*
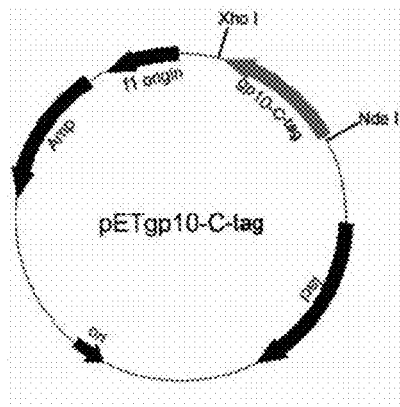
*FIG.2B*
| Primers | Sequence (5'-3') |
|---|---|
| F1 | CGCAGCTGGCATATGGCACGTAAACGCAGTAAC |
| R1 | GGATGACTCCAACCTCCTCCACCACCTCCCTCATTTGTTTCACCGT |
| R2 | ATAATGTTCTCGAGCTACTTTTCGAACTGCGGATGACTCCAACCTC |
*FIG.2C*

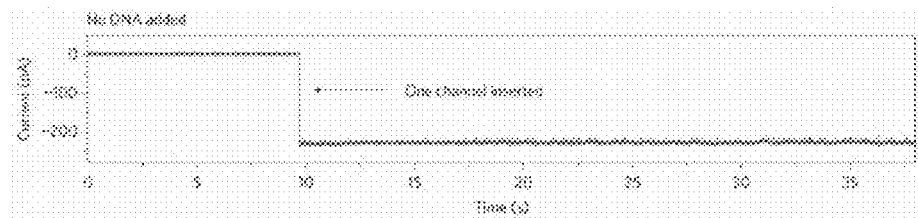
*FIG.8A*
*FIG.8B*
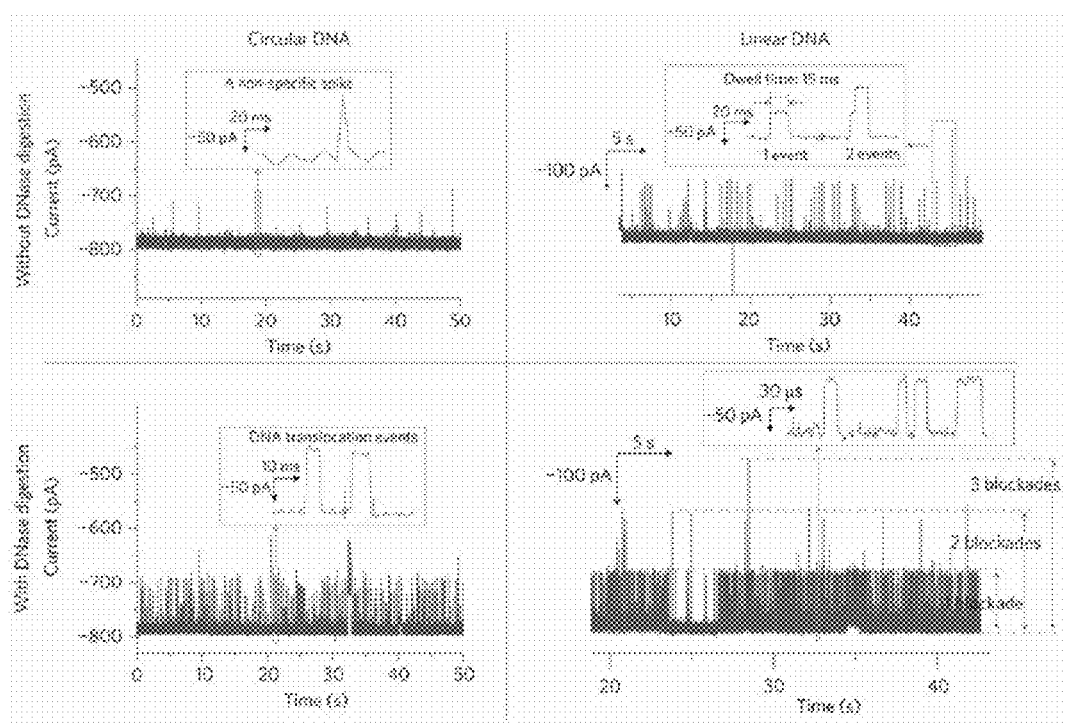

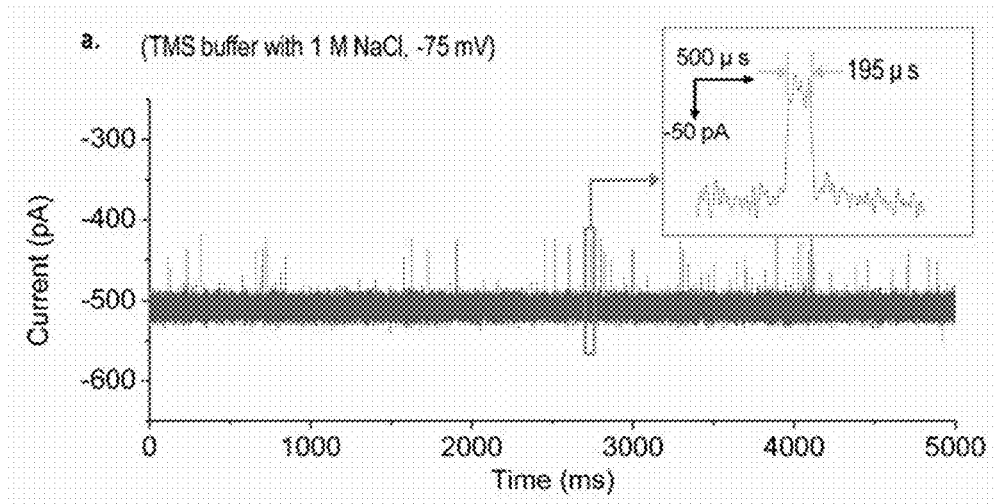
*FIG.10A*
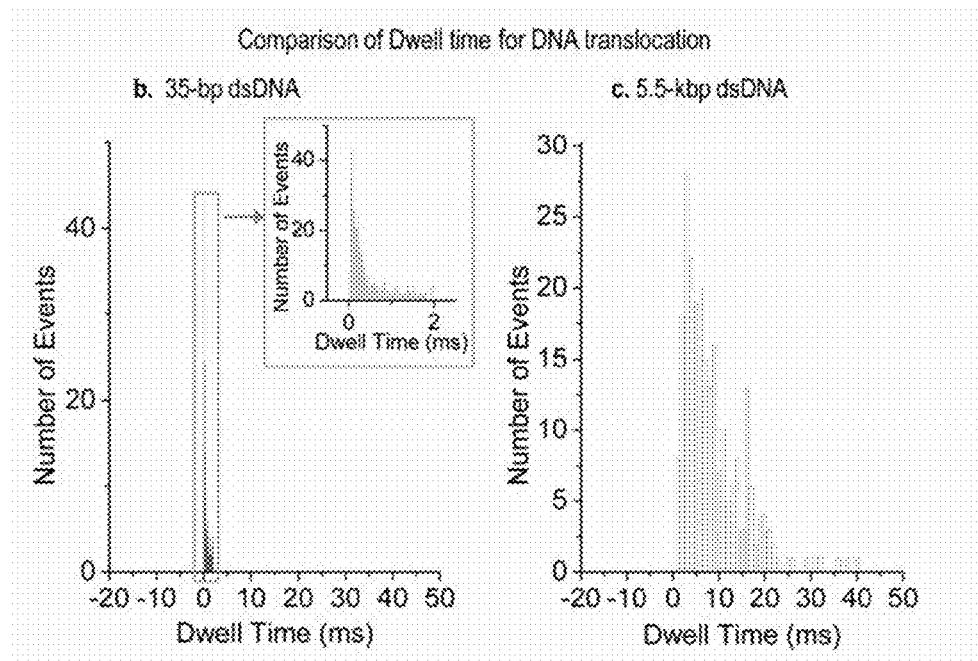
*FIG.10B*   *FIG.10C*

MEMBRANE-INTEGRATED VIRAL DNA-PACKAGING MOTOR PROTEIN CONNECTOR BIOSENSOR FOR DNA SEQUENCING AND OTHER USES

CROSS-REFERENCE TO RELATED APPLICATION

This application is a continuation in part of international patent application PCT/US09/62826, which was filed on Oct. 30, 2009, which claims the benefit of U.S. Provisional Application Ser. No. 61/109,669, filed Oct. 30, 2008.

STATEMENT OF GOVERNMENT INTEREST

This invention was made with government support under Grant No. PN2 EY 018230, awarded by the NIH Nanomedicine Development Center/NIH Roadmap for Medical Research/National Institutes of Health, and Grants No. R01-GM59944, EB 03730 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification entirely. The name of the text file containing the Sequence Listing is CIP_PXG_SEQUENCE_LISTING.txt. The text file is 102 KB, was created on Apr. 15, 2011, and is being submitted electronically via EFS-Web to the U.S. Patent Office, concurrent with the filing of the specification.

The Sequence Listing text file submitted herein does not include any new matter which goes beyond the disclosure of the application as filed.

BACKGROUND

1. Technical Field

The present invention embodiments relate generally to the field of biosensors. More specifically, the compositions and methods described herein relate to an engineered viral DNA-packaging motor protein connector that can be incorporated into a lipid membrane to form an electroconductive aperture (or to form a fluorescence excitation aperture), for use in DNA sequencing and other applications.

2. Description of the Related Art

Highly sensitive detection and characterization of minute quantities of chemicals and biochemicals represent desirable goals of modern analytical technologies. Robust molecular sensing devices would find uses in a wide range of biomedical, industrial, environmental, forensic, security and other contexts, for example, in the detection and identification of pathogens and chemicals at extremely low concentrations for disease diagnosis and environmental monitoring, in high throughput DNA sequencing and other genomics applications, and elsewhere.

Analytical methodologies have been described that employ intermolecular affinity binding interactions, typically non-covalent in nature, to detect binding or "capture" of an analyte of interest by a specific affinity ligand, for instance, including detection of bacterial, viral, parasitic or other microbial pathogens or pathogen-associated antigens, and detection of antibodies, cancer markers, and other analytes (e.g., Kittigul et al., *Am J Trop Med Hyg.* 1998 September; 59(3):352-6; Cordiano et al., *J Immunol Methods.* 1995 Jan. 13; 178(1):121-30; Olson et al., *J Immunol Methods.* 1990 Nov. 6; 134(1):71-9; Nerurkar et al., *J Clin Microbiol.* 1984 July; 20(1):109-14; Jia et al., *J Virol Methods.* 2009 October; 161(1):38-43; He et al., *Clin Vaccine Immunol.* 2007 May; 14(5):617-23; Xu et al., *J Clin Microbiol.* 2006 August; 44(8): 2872-8; Che et al., *J Clin Microbiol.* 2004 June; 42(6):2629-35; Hunt et al., Brown et al., *Am J Trop Med Hyg.* 2001 September; 65(3):208-13; Loa et al., *Avian Dis.* 2000 July-September; 44(3):498-506; Lubenko et al., *Transfus Med.* 2000 September; 10(3):213-8; Chanteau et al., *Int J Tuberc Lung Dis.* 2000 April; 4(4):377-83; Brinker et al., *J Clin Microbiol.* 1998 April; 36(4):1064-9; Vyse et al., *J Virol Methods.* 1997 January; 63(1-2):93-101; Peterson et al., *J Clin Microbiol.* 1997 January; 35(1):208-12; Lairmore et al., *AIDS Res Hum Retroviruses.* 1993 June; 9(6):565-71; Heller et al., *Vet Microbiol.* 1993 October; 37(1-2):127-33; van Loon et al., *Epidemiol Infect.* 1992 February; 108(1):165-74; Wolf-Rogers et al., *J Immunol Methods.* 1990 Oct. 19; 133(2):191-8; Barsoum et al., *Exp Parasitol.* 1990 July; 71(1):107-13; Hierholzer et al., *J Clin Microbiol.* 1989 June; 27(6):1243-9; Hurley et al., *J Immunoassay.* 1986; 7(4):309-36; Wolff et al., *Cancer Res.* 53:2560-65 (1993); see generally, e.g., Harlow and Lane, *Antibodies: A Laboratory Manual*, Cold Spring Harbor Laboratory, 1988; Weir, D. M., *Handbook of Experimental Immunology*, 1986, Blackwell Scientific, Boston, Mass.).

Beyond detection of the presence of an analyte following its involvement in an affinity binding interaction, sophisticated technologies are emerging that permit characterization of the analyte, often by comparing a single- or multiparameter physicochemical profile of the analyte to type-characteristic profiles generated using one or more known reference standards, and hence referred to as "fingerprinting" techniques. (e.g., Li et al., *Rapid Commun Mass Spectrom.* 2009 23(22): 3533-3542; Ali et al., *J Agric Food Chem.* 2009; Leski et al., *Appl Environ Microbiol.* Sep. 18, 2009; Weinkopff et al., *J Parasitol.* Jun. 18, 2009; Song et al., *Proteomics.* 2009 9(11): 3090-9; Ortea et al., *J Agric Food Chem.* 2009 57(13):5665-72; Amini, *Pharmeur Sci Notes.* 2009(1):11-6; Shi et al., *Biol Pharm Bull.* 2009 32(1):142-6; Sun et al., *J Chromatogr A.* 2009 1216(5):830-6; Yin et al., *Phytopathology.* 2003 93(8): 1006-13; Roy et al., *Clin Cancer Res.* 2008 14(20):6610-7; Pei et al., *Zhongguo Zhong Yao Za Zhi.* 2008 33(14):1662-8; Arthur, *Methods Mol Med.* 2008, 141:257-70; Zhao et al., *Se Pu* 2008 26(1):43-9; Woo et al., *Anal Chem.* 2008 80(7): 2419-25; Damodaran et al., *Genomics Proteomics Bioinformatics.* 2007 5(3-4):152-7; Fellström et al., *J Microbiol Methods.* 2008 72(2):133-40; Song et al., *Conf Proc IEEE Eng Med Biol Soc.* 2006 1:4556-9; De Vuyst et al., *Int J Food Microbiol.* 2008 125(1):79-90).

The use of transmembrane channels has been demonstrated in stochastic analyte detection (Bayley et al., 2001 *Nature* 13:225-230), an electrochemical approach relying on the real-time observation of individual binding events between single substrate molecules and a receptor, as evidenced by altered (e.g., decreased or increased in a statistically significant manner) electrical conductance by the channel (receptor) as a result of substrate (analyte) binding. A wide range of processes, such as the transport of DNA, RNA, pharmaceutical agents, peptides, proteins, and polymers, have been studied by such approaches, for example, using electrophysiological measurements of individual membrane channels (Thieffry et al., 1988 *EMBO J* 7:1449; Hinnah et al., 2002 *Biophys J* 83:899; Alcayaga et al., 1992 *FEBS Lett.* 311:246-50; Benz et al., 1986 *J Bacteriol* 165:978; Movileanu et al., 2000 *Nat. Biotechnol.* 18:1091).

For instance, the transient blockade of ionic current through the *Staphylococcus aureus* alpha-hemolysin (α-HL) channel, a bacterial transmembrane pore-forming protein, has been used to measure the length of single-stranded DNA or RNA (Kasianowicz et al. *Proc. Natl. Acad. Sci. USA* 93, 13770-13773 (1996)). Subsequently, DNA hairpin molecules have been used to decelerate the DNA translocation rate through the alpha-hemolysin (α-HL) pore, to demonstrate the ability of a transmembrane ion channel to discriminate between single nucleotide polymorphisms (Vercoutere et al., 2001 *Nat. Biotechnol.* 19:248). Detection of base pair stacking and strand orientation within the pore have also been investigated (Vercoutere et al., 2003 *Nucl Ac. Res.* 31:1311; Howorka et al., 2001 *Nat. Biotechnol.* 19:636; deGuzman et al., 2006 *Nucl. Ac. Res.* 34:6425). The channel of α-HL with a covalently attached adapter molecule has been shown to discriminate the nucleotides A, T, G, and C (Clarke et al., 2009 *Nat. Nanotechnol.* 4:265).

Other protein channels that have been investigated include alamethicin for detection of polyethylene glycol (Bezrukov, 2000 *J Membr Biol.* 174:1-13), and the reengineered MspA protein from *M. smegmatis* for translocation of ssDNA (Butler et al., 2008 *Proc. Nat. Acad. Sci. USA* 105:20647). Most studies involving nucleic acid transport through nanopores have focused on α-HL. However, the limiting lumen diameter of α-HL (1.5 nm) and other channels has restricted their DNA and RNA applications to translocation of single-stranded nucleic acid (Song, 1996 *Science* 274:1859). A similar limitation was also reported for the MspA nanopore (Butler et al., 2008).

In a small number of other membrane pore systems, evidence of double-stranded DNA (dsDNA) transport across the membrane has been presented (Szabo et al., 2002 *Cell Physiol Biochem* 12:127; Mobasheri et al. 2002 *Eur J Bipohys* 31:389; Carneiro et al., 2003 *Biochim Biophys Acta* 1612: 144), but these systems are not robust and represent poor candidates for widespread use such as biomedical applications, due to their undesirable voltage gating properties and the associated signal fluctuation. For this reason, their potential is considered limited and researchers have switched instead to fabricating synthetic metal or silicon nanopores for potential use in DNA sequencing (Smeets et al, 2006 *Nano Lett* 6:89; Wang et al., 2001 *Nat. Biotechnol.* 19:622; Iqbal et al., 2007 *Nat. Nano* 2:243). Such synthetic nanopores, however, suffer from shortcomings due to difficulties in reliably producing replicated structures having consistent properties from batch to batch, and also lack versatility with regard to the ability to engineer modifications to pore structures and/or to serve as substrates for modification by a wide range of chemical conjugation. As a result, the search for superior alternatives to currently available protein nanopores is still ongoing.

Clearly there is a need for improved compositions and methods that would provide a versatile membrane conductive channel platform for sensitively detecting and characterizing a wide range of analytes, having a lumen capable of accommodating dsDNA, that can be reliably and reproducibly assembled, that is not susceptible to voltage gating under working conditions, and that can be readily modified to feature a wide variety of specific affinity receptors for use in the detection and characterization of different analytes. The presently disclosed invention embodiments fulfill such a need, and offer other related advantages.

With regards to optical detection based DNA sequence or other applications within membrane integrated biosensors, current procedures also have their limitations. For example, batch DNA sequencing using fluorescent dyes have been developed by different labs (Shendure J A, et al *Curr. Protoc.* *Mol. Biol.* 2008 January; Chapter 7: Unit 7.1; Bayley H. *Curr. Opin. Chem. Biol.* 2006 December; 10(6):628-37; Korlach J, et al *Nucleosides Nucleotides Nucleic Acids* 2008 September; 27(9):1072-83. PMCID:PMC2582155; Soni G V, Meller A. *Clin. Chem.* 2007 November; 53(11):1996-2001). The traditional optical detection for DNA sequencing normally uses fluorescent 2',3'-dedeoxy nucleotide as the chain terminator; therefore, the traditional approach is limited by the number of base pairs one procedure can achieve.

An improved composition and methods that would provide a membrane integrated reaction pore for high throughput, optical detection based application is in need. This disclosure further presents embodiments that fulfill the concept of a single pore based optical biosensor system.

BRIEF SUMMARY

The present invention provides, in certain embodiments a conductive channel-containing membrane, comprising (a) a membrane layer; and (b) an isolated viral DNA-packaging motor connector protein that is incorporated into the membrane layer to form an aperture through which conductance can occur when an electrical potential is applied across the membrane. In certain embodiments the viral DNA-packaging motor connector protein is artificial. In certain embodiments the viral DNA-packaging motor connector protein comprises a homododecamer of viral DNA-packaging motor connector protein polypeptide subunits, wherein each of said subunits comprises (a) an aperture domain that comprises an isolated viral connector protein polypeptide having an amino terminus and a carboxy terminus; and (b) either or both of (i) at least one flexibility domain that comprises a polypeptide of 4, 5, 6, 7, 8, 9, 10, 11, 12, 13, 14, 15, 16, 17 or 18 contiguous uncharged amino acids and that is fused to at least one of the amino terminus and the carboxy terminus of (a), and (ii) at least one affinity/alignment domain. In certain embodiments the viral DNA-packaging motor connector protein comprises a homododecamer of viral DNA-packaging motor connecting protein polypeptide subunits, wherein each of said subunits comprises (a) an aperture domain that comprises an isolated viral connector protein polypeptide having an amino terminus and a carboxy terminus; and (b) either or both of (i) at least one flexibility domain that comprises a polypeptide of 4, 5, 6, 7, 8, 9, 10, 11, 12, 13 or 14 contiguous uncharged amino acids and that is fused to at least one of the amino terminus and the carboxy terminus of (a), and (ii) at least one affinity/alignment domain that comprises a polypeptide of formula $X_{1a}$-$X_{1a}$-$X_{2a}$-$X_{1b}$-$X_{1b}$-$X_{1b}$-$X_3$-$X_{2b}$ and that is fused to the flexibility domain, wherein each $X_{1a}$ is independently either any uncharged amino acid or no amino acid, each $X_{1b}$ is independently any uncharged amino acid, $X_{2a}$ is a positively charged amino acid selected from lysine, arginine and histidine, $X_3$ is a negatively charged amino acid selected from glutamic acid and aspartic acid, and $X_{2b}$ is a positively charged amino acid selected from lysine, arginine and histidine.

In certain embodiments the viral DNA-packaging motor connector protein comprises a homododecamer of viral DNA-packaging motor connector protein polypeptide subunits, wherein each of said subunits comprises (a) an aperture domain that comprises an isolated viral connector protein polypeptide having an amino terminus and a carboxy terminus; and (b) either or both of (i) at least one flexibility domain that comprises a polypeptide of sequence Gly-Gly-Gly-Gly-Gly-Gly as set forth in SEQ ID NO:23 and that is fused to the carboxy terminus of (a), and (ii) at least one affinity/alignment domain that is fused to the flexibility domain. In certain embodiments the affinity/alignment domain comprises a polypeptide that is selected from (i) a Strep-II tag as set forth in SEQ ID NO:22 [WSHPQRFEK], (ii) a polyhistidine polypeptide tag of 3, 4, 5, 6, 7, 8, 9, 10, 11 or 12 contiguous histidine residues, (iii) a polyarginine polypeptide of 3, 4, 5, 6, 7, 8, 9, 10, 11 or 12 contiguous arginine residues, (iv) an HIV Tat polypeptide of sequence YGRKKRRQRR [SEQ ID NO:39], and (v) a peptide tag of sequence DRATPY [SEQ ID NO:40]. In certain embodiments the viral DNA-packaging motor connector protein comprises a homododecamer of viral DNA-packaging motor connector protein polypeptide subunits, wherein each of said subunits is selected from (i) C-His6-gp10/K234A as set forth in SEQ ID NO:41, (ii) C-His6-gp10/K234C as set forth in SEQ ID NO:42, (iii) C-His6-gp10/C76S/C265S/K234C as set forth in SEQ ID NO:43, (iv) Δ1-14/gp10-Strep-II as set forth in SEQ ID NO:44, and (v) Gp10/Δ285-309-Strep-II as set forth I SEQ ID NO:45.

In certain embodiments the viral DNA-packaging motor connector protein comprises a homododecamer of viral DNA-packaging motor connector protein polypeptide subunits that each comprise a polypeptide selected from (i) all or a transmembrane aperture-forming portion of bacteriophage phi29 DNA-packaging motor connector protein polypeptide having the amino acid sequence set forth in SEQ ID NO:1 [Acc. No. ACE96033] (ii) all or a transmembrane aperture-forming portion of phage T4 DNA-packaging motor connector protein polypeptide having the amino acid sequence set forth in SEQ ID NO:7 [Acc. No. NP_049782], (iii) all or a transmembrane aperture-forming portion of phage lambda DNA-packaging motor connector protein polypeptide having the amino acid sequence set forth in any one of SEQ ID NOS:8-11 [Acc. Nos. gi 549295, gi 6723246, gi 15837315, gi 16764273], (iv) all or a transmembrane aperture-forming portion of phage SPP1 DNA-packaging motor connector protein polypeptide having the amino acid sequence set forth in SEQ ID NO:12 [Acc. No. P54309], (v) all or a transmembrane aperture-forming portion of phage P22 DNA-packaging motor connector protein polypeptide having the amino acid sequence set forth in SEQ ID NO:13 [Acc. No. AAA72961], (vi) all or a transmembrane aperture-forming portion of phage P2 DNA-packaging motor connector protein polypeptide having the amino acid sequence set forth in SEQ ID NO:14 [Acc. No. NP_046757], (vii) all or a transmembrane aperture-forming portion of phage P3 DNA-packaging motor connector protein polypeptide, (viii) all or a transmembrane aperture-forming portion of phage T3 DNA-packaging motor connector protein polypeptide having the amino acid sequence set forth in SEQ ID NO:15 [Acc. No. CAA35152], (ix) all or a transmembrane aperture-forming portion of phage T5 DNA-packaging motor connector protein polypeptide having the amino acid sequence set forth in SEQ ID NOS:16-19 (Accession numbers AAX12078, YP_006980; AAS77191; AAU05287), and (x) all or a transmembrane aperture-forming portion of phage T7 DNA-packaging motor connector protein polypeptide having the amino acid sequence set forth in SEQ ID NO:20 [Acc. No. NP_041995].

In certain embodiments the viral DNA-packaging motor connector protein comprises a homododecamer of viral DNA-packaging motor connector protein polypeptide subunits that each comprise a polypeptide that comprises all or a transmembrane aperture-forming portion of a double-stranded DNA bacteriophage DNA-packaging motor connector protein. In certain embodiments the viral connector protein polypeptide is selected from (i) all or a transmembrane aperture-forming portion of bacteriophage phi29 DNA-packaging motor connector protein polypeptide having the amino acid sequence set forth in SEQ ID NO:1 [Acc. No. ACE96033] (ii) all or a transmembrane aperture-forming portion of phage T4 DNA-packaging motor connector protein polypeptide having the amino acid sequence set forth in SEQ ID NO:7 [Acc. No. NP_049782], (iii) all or a transmembrane aperture-forming portion of phage lambda DNA-packaging motor connector protein polypeptide having the amino acid sequence set forth in any one of SEQ ID NOS:8-11 [Acc. Nos. gi 549295, gi 6723246, gi 15837315, gi 16764273], (iv) all or a transmembrane aperture-forming portion of phage SPP1 DNA-packaging motor connector protein polypeptide having the amino acid sequence set forth in SEQ ID NO:12 [Acc. No. P54309], (v) all or a transmembrane aperture-forming portion of phage P22 DNA-packaging motor connector protein polypeptide having the amino acid sequence set forth in SEQ ID NO:13 [Acc. No. AAA72961], (vi) all or a transmembrane aperture-forming portion of phage P2 DNA-packaging motor connector protein polypeptide having the amino acid sequence set forth in SEQ ID NO:14 [Acc. No. NP_046757], (vii) all or a transmembrane aperture-forming portion of phage P3 DNA-packaging motor connector protein polypeptide, (viii) all or a transmembrane aperture-forming portion of phage T3 DNA-packaging motor connector protein polypeptide having the amino acid sequence set forth in SEQ ID NO:15 [Acc. No. CAA35152], (ix) all or a transmembrane aperture-forming portion of phage T5 DNA-packaging motor connector protein polypeptide having the amino acid sequence set forth in SEQ ID NOS:16-19 (Accession numbers AAX12078, YP_006980; AAS77191; AAU05287), and (x) all or a transmembrane aperture-forming portion of phage T7 DNA-packaging motor connector protein polypeptide having the amino acid sequence set forth in SEQ ID NO:20 [Acc. No. NP_041995].

In certain embodiments the viral DNA-packaging motor connector protein comprises a homododecamer of viral DNA-packaging motor connector protein polypeptide subunits that each comprise a polypeptide that comprises all or a transmembrane aperture-forming portion of bacteriophage phi29 DNA-packaging motor connector protein polypeptide having the amino acid sequence set forth in SEQ ID NO:1 [Acc. No. ACE96033]. In certain embodiments the viral connector protein polypeptide comprises all or a transmembrane aperture-forming portion of bacteriophage phi29 DNA-packaging motor connector protein polypeptide having the amino acid sequence set forth in SEQ ID NO:1 [Acc. No. ACE96033]. In certain embodiments the viral DNA-packaging motor connector protein comprises a detectable label, which may in certain further embodiments be selected from a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label. In certain further embodiments the affinity label is selected from avidin, streptavidin, biotin, an aptamer, an antibody, a lectin, an oligosaccharide, a nucleic acid, an enzyme, a metal ion-binding polypeptide, a Strep-II tag as set forth in SEQ ID NO:22 [WSHPQRFEK], a polyhistidine polypeptide tag of 3, 4, 5, 6, 7, 8, 9, 10 or 12 contiguous histidine residues, a Strep-I tag, a FLAG® peptide tag, a Myc peptide tag, glutathione-S-transferase, maltose binding protein, S. aureus protein A, protein G, HIV Tat polypeptide [SEQ ID NO:39], a peptide having the amino acid sequence DRATPY [SEQ ID NO:40], glutaredoxin-2, and a phage-displayed peptide that specifically binds an affinity ligand. In certain further embodiments the antibody is selected from an intact immunoglobulin, a single-chain antibody, an scFv, a Fab and a (Fab)'$_2$.

In certain embodiments relating to the above described conductive channel-containing membrane, the membrane layer comprises a lipid layer. In a further embodiment the lipid layer comprises amphipathic lipids, which in certain still further embodiments comprise phospholipids and the lipid layer comprises a lipid bilayer. In certain other embodiments the lipid layer is selected from a planar membrane layer and a liposome. In certain embodiments the liposome is selected from a multilamellar liposome and a unilamellar liposome. In certain other embodiments the incorporated viral DNA-packaging motor connector protein is mobile in the membrane layer. In certain other embodiments the conductive channel-containing membrane is capable of translocating double-stranded DNA through the aperture when the electrical potential is applied. In certain embodiments conductance occurs without voltage gating when the electrical potential is applied.

According to certain other embodiments of the present invention, there is provided a method of making a conductive channel-containing membrane, comprising (a) preparing dried amphipathic lipids on a solid substrate by contacting a first solution comprising amphipathic lipids and an organic solvent with the solid substrate and substantially removing the solvent; and (b) resuspending the dried amphipathic lipids in a second solution that comprises an aqueous solvent, an osmotic agent and a plurality of isolated viral DNA-packaging motor connector protein subunit polypeptides that are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when an electrical potential is applied across the membrane, and thereby making a conductive channel-containing membrane.

In certain other embodiments there is provided a method of making a conductive channel-containing membrane, comprising (a) substantially removing solvent from a mixture comprising amphipathic lipids and at least one solvent, to obtain dried amphipathic lipids; and (b) resuspending the dried amphipathic lipids in a second solution that comprises an aqueous solvent, an osmotic agent and a plurality of isolated viral DNA-packaging motor connector protein subunit polypeptides that are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when an electrical potential is applied across the membrane, and thereby making a conductive channel-containing membrane.

In certain further embodiments of the above described methods, the amphipathic lipids comprise phospholipids. In certain further embodiments the phospholipids comprise one or more phospholipids selected from phosphatidylcholine, phosphatidylethanolamine, phosphatidylserine, phosphatidylinositol, phosphatidylglycerol, cardiolipin, 1,2-diphytanoyl-sn glycerol-3-phosphocholine, and 1,2-dioleoyl-sn-glycero-3-phosphocholine. In certain embodiments the organic solvent comprises at least one solvent selected from chloroform, methanol, ethanol, n-propanol, isopropanol, n-butanol, isobutanol, pyridine, and diisopropyl ether. In certain embodiments the osmotic agent comprises at least one agent that is selected from sucrose or another disaccharide, glycerol, mannitol and dextran. In certain embodiments the DNA-packaging motor connector protein subunit comprises any of the above described DNA-packaging motor connector protein subunit polypeptides. In certain embodiments the lipid bilayer is present in a liposome, which in certain further embodiments is selected from a multilamellar liposome and a unilamellar liposome. In certain embodiments the incorporated viral DNA-packaging motor connector protein is mobile in the membrane layer. In certain embodiments the viral DNA-packaging motor connector protein is capable of translocating double-stranded DNA through the aperture when electrical potential is applied to the membrane. In certain embodiments conductance occurs in the conductive channel-containing membrane without voltage gating when electrical potential is applied. In certain further embodiments the applied electrical potential is selected from (i) a potential that is between −100 mV and 100 mV, (ii) a potential that is between −400 mV and 400 mV, (iii) a potential that is between −300 mV and 300 mV, (iv) a potential that is between −200 mV and 200 mV, (v) a potential that is between −150 mV and 150 mV, (vi) a potential that is between −75 mV and 75 mV, and (vii) a potential that is between −50 mV and 50 mV.

According to certain other embodiments of the present invention there is provided a method of concentrating nucleic acid molecules on one side of a conductive channel-containing membrane that comprises a first side and a second side, the method comprising (a) making a conductive channel-containing membrane by a method comprising (i) substantially removing solvent from a mixture comprising amphipathic lipids and at least one solvent, to obtain dried amphipathic lipids; and (ii) resuspending the dried amphipathic lipids in a second solution that comprises an aqueous solvent, an osmotic agent and a plurality of isolated viral DNA-packaging motor connector protein subunit polypeptides that are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when an electrical potential is applied across the membrane, and thereby making a conductive channel-containing membrane; and (b) contacting the conductive channel-containing membrane of (a) with one or a plurality of nucleic acid molecules and with an electrical potential that is applied across the membrane, under conditions and for a time sufficient for electrophoretic translocation of the nucleic acid through the aperture of the connector protein, and thereby concentrating nucleic acid molecules on one side of the conductive channel-containing membrane. In certain further embodiments nucleic acid translocation causes accumulation of the nucleic acid on one side of the membrane and against a nucleic acid concentration gradient. In another embodiment there is provided a nucleic acid-containing liposome that comprises a conductive channel-containing membrane and nucleic acid molecules that are concentrated on one side of the membrane, wherein the liposome is produced according to the method just described. In certain further embodiments the liposome is a nanoparticle, and in certain other embodiments the liposome is a bioreactor. According to certain embodiments there is provided a method for delivering a nucleic acid to a cell, comprising introducing to the cell one or a plurality of the liposomes described above. In one embodiment the cell is introduced to the one or plurality of liposomes in vitro, and in another embodiment the cell is introduced to the one or plurality of liposomes in vivo.

In another embodiment of the present invention there is provided an isolated protein, comprising a homododecamer of viral DNA-packaging motor connector protein polypeptide subunits, wherein each of said subunits comprises a fusion protein which comprises (a) an aperture domain that comprises an isolated viral connector protein polypeptide having an amino terminus and a carboxy terminus; (b) at least one flexibility domain that comprises a polypeptide of 4, 5, 6, 7, 8, 9, 10, 11, 12, 13, 14, 15, 16, 17 or 18 contiguous uncharged amino acids and that is fused to at least one of the amino terminus and the carboxy terminus of (a); and (c) at least one affinity/alignment domain.

In another embodiment there is provided an isolated protein, comprising a homododecamer of viral DNA-packaging motor connector protein polypeptide subunits, wherein each of said subunits comprises a fusion protein which comprises (a) an aperture domain that comprises an isolated viral connector protein polypeptide having an amino terminus and a carboxy terminus; (b) at least one flexibility domain that comprises a polypeptide of 4, 5, 6, 7, 8, 9, 10, 11, 12, 13 or 14 contiguous uncharged amino acids and that is fused to at least one of the amino terminus and the carboxy terminus of (a); and (c) at least one affinity/alignment domain that comprises a polypeptide of formula $X_{1a}$-$X_{1a}$-$X_{2a}$-$X_{1b}$-$X_{1b}$-$X_{1b}$-$X_3$-$X_{2b}$ and that is fused to the flexibility domain, wherein each $X_{1a}$ is independently either any uncharged amino acid or no amino acid, each $X_{1b}$ is independently any uncharged amino acid, $X_{2a}$ is a positively charged amino acid selected from lysine, arginine and histidine, $X_3$ is a negatively charged amino acid selected from glutamic acid and aspartic acid, and $X_{2b}$ is a positively charged amino acid selected from lysine, arginine and histidine.

In one embodiment there is provided an isolated protein, comprising a homododecamer of viral DNA-packaging motor connector protein polypeptide subunits, wherein each of said subunits comprises a fusion protein which comprises (a) an aperture domain that comprises an isolated viral connector protein polypeptide having an amino terminus and a carboxy terminus; (b) at least one flexibility domain that comprises a polypeptide of sequence Gly-Gly-Gly-Gly-Gly-Gly as set forth in SEQ ID NO:23 and that is fused to the carboxy terminus of (a); and (c) at least one affinity/alignment domain that is fused to the flexibility domain. In certain further embodiments the affinity/alignment domain comprises a polypeptide that is selected from (i) a Strep-II tag as set forth in SEQ ID NO:22 [WSHPQRFEK], (ii) a polyhistidine polypeptide tag of 3, 4, 5, 6, 7, 8, 9, 10, 11 or 12 contiguous histidine residues, (iii) a polyarginine polypeptide of 3, 4, 5, 6, 7, 8, 9, 10, 11 or 12 contiguous arginine residues, (iv) an HIV Tat polypeptide of sequence YGRKKRRQRRR [SEQ ID NO:39] and (v) a peptide tag of sequence DRATPY [SEQ ID NO:40].

In another embodiment there is provided an isolated protein, comprising a homododecamer of viral DNA-packaging motor connector protein polypeptide subunits, wherein each of said subunits comprises a polypeptide that is selected from (i) C-His6-gp10/K234A as set forth in SEQ ID NO:41, (ii) C-His6-gp10/K234C as set forth in SEQ ID NO:42, (iii) C-His6-gp10/C76S/C265S/K234C as set forth in SEQ ID NO:43, (iv) Δ1-14/gp10-Strep-II as set forth in SEQ ID NO:44, and (v) Gp10/Δ285-309-Strep-II as set forth I SEQ ID NO:45.

In certain embodiments the aperture domain comprises a polypeptide that is selected from (i) all or a transmembrane aperture-forming portion of bacteriophage phi29 DNA-packaging motor connector protein polypeptide having the amino acid sequence set forth in SEQ ID NO:1 [Acc. No. ACE96033] (ii) all or a transmembrane aperture-forming portion of phage T4 DNA-packaging motor connector protein polypeptide having the amino acid sequence set forth in SEQ ID NO:7 [Acc. No. NP_049782], (iii) all or a transmembrane aperture-forming portion of phage lambda DNA-packaging motor connector protein polypeptide having the amino acid sequence set forth in any one of SEQ ID NOS:8-11 [Acc. Nos. gi 549295, gi 6723246, gi 15837315, gi 16764273], (iv) all or a transmembrane aperture-forming portion of phage SPP1 DNA-packaging motor connector protein polypeptide having the amino acid sequence set forth in SEQ ID NO:12 [Acc. No. P54309], (v) all or a transmembrane aperture-forming portion of phage P22 DNA-packaging motor connector protein polypeptide having the amino acid sequence set forth in SEQ ID NO:13 [Acc. No. AAA72961], (vi) all or a transmembrane aperture-forming portion of phage P2 DNA-packaging motor connector protein polypeptide having the amino acid sequence set forth in SEQ ID NO:14 [Acc. No. NP_046757], (vii) all or a transmembrane aperture-forming portion of phage P3 DNA-packaging motor connector protein polypeptide, (viii) all or a transmembrane aperture-forming portion of phage T3 DNA-packaging motor connector protein polypeptide having the amino acid sequence set forth in SEQ ID NO:15 [Acc. No. CAA35152], (ix) all or a transmembrane aperture-forming portion of phage T5 DNA-packaging motor connector protein polypeptide having the amino acid sequence set forth in SEQ ID NOS:16-19 (Accession numbers AAX12078, YP_006980; AAS77191; AAU05287), and (x) all or a transmembrane aperture-forming portion of phage T7 DNA-packaging motor connector protein polypeptide having the amino acid sequence set forth in SEQ ID NO:20 [Acc. No. NP_041995].

In certain embodiments the aperture domain comprises a polypeptide that comprises all or a transmembrane aperture-forming portion of a double-stranded DNA bacteriophage DNA-packaging motor connector protein. In certain embodiments the aperture domain comprises a polypeptide that is (i) all or a transmembrane aperture-forming portion of bacteriophage phi29 DNA-packaging motor connector protein polypeptide having the amino acid sequence set forth in SEQ ID NO:1 [Acc. No. ACE96033] (ii) all or a transmembrane aperture-forming portion of phage T4 DNA-packaging motor connector protein polypeptide having the amino acid sequence set forth in SEQ ID NO:7 [Acc. No. NP_049782], (iii) all or a transmembrane aperture-forming portion of phage lambda DNA-packaging motor connector protein polypeptide having the amino acid sequence set forth in any one of SEQ ID NOS:8-11 [Acc. Nos. gi 549295, gi 6723246, gi 15837315, gi 16764273], (iv) all or a transmembrane aperture-forming portion of phage SPP1 DNA-packaging motor connector protein polypeptide having the amino acid sequence set forth in SEQ ID NO:12 [Acc. No. P54309], (v) all or a transmembrane aperture-forming portion of phage P22 DNA-packaging motor connector protein polypeptide having the amino acid sequence set forth in SEQ ID NO:13 [Acc. No. AAA72961], (vi) all or a transmembrane aperture-forming portion of phage P2 DNA-packaging motor connector protein polypeptide having the amino acid sequence set forth in SEQ ID NO:14 [Acc. No. NP_046757], (vii) all or a transmembrane aperture-forming portion of phage P3 DNA-packaging motor connector protein polypeptide, (viii) all or a transmembrane aperture-forming portion of phage T3 DNA-packaging motor connector protein polypeptide having the amino acid sequence set forth in SEQ ID NO:15 [Acc. No. CAA35152], (ix) all or a transmembrane aperture-forming portion of phage T5 DNA-packaging motor connector protein polypeptide having the amino acid sequence set forth in SEQ ID NOS:16-19 (Accession numbers AAX12078, YP_006980; AAS77191; AAU05287), and (x) all or a transmembrane aperture-forming portion of phage T7 DNA-packaging motor connector protein polypeptide having the amino acid sequence set forth in SEQ ID NO:20 [Acc. No. NP_041995].

In certain embodiments the aperture domain comprises a polypeptide that comprises all or a transmembrane aperture-forming portion of a bacteriophage phi29 DNA-packaging motor connector protein polypeptide having the amino acid sequence set forth in SEQ ID NO:1 [Acc. No. ACE96033]. In certain embodiments the viral connector protein polypeptide comprises all or a transmembrane aperture-forming portion of bacteriophage phi29 DNA-packaging motor connector protein polypeptide having the amino acid sequence set forth in SEQ ID NO:1 [Acc. No. ACE96033]. In certain embodiments the above described isolated protein is capable of (i) self-assembly into a dodecameric viral connector protein, and (ii) packaging viral dsDNA following incorporation into a viral procapsid. In certain embodiments the isolated protein comprises at least one detectable label, which in certain further embodiments is selected from a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label. In certain further embodiments the affinity label is selected from avidin, streptavidin, biotin, an aptamer, an antibody, a lectin, an oligosaccharide, a nucleic acid, an enzyme, a metal ion-binding polypeptide, a Strep-II tag as set forth in SEQ ID NO:22 [WSHPQRFEK], a polyhistidine polypeptide tag of 3, 4, 5, 6, 7, 8, 9, 10, 11 or 12 contiguous histidine residues, a Strep-I tag, a FLAG® peptide tag, a Myc peptide tag, glutathione-S-transferase, maltose binding protein, S. aureus protein A, protein G, an HIV Tat polypeptide of sequence YGRKKRRQRRR [SEQ ID NO:39], a peptide having the amino acid sequence DRATPY [SEQ ID NO:40], glutaredoxin-2, and a phage-displayed peptide that specifically binds an affinity ligand. In certain embodiments the antibody is selected from an intact immunoglobulin, a single-chain antibody, an scFv, a Fab and a (Fab)'2.

In another embodiment of the present invention there is provided a method for detecting presence of an analyte molecule, comprising (a) contacting a test solution containing the analyte molecule with a conductive channel-containing membrane which comprises a membrane layer and incorporated therein one or a plurality of isolated viral DNA-packaging motor connector proteins that are capable of forming an aperture through which conductance can occur when an electrical potential is applied across the membrane, and that each comprise a homododecamer of viral DNA-packaging motor connector protein polypeptide subunits, wherein each of said subunits comprises (1) an aperture domain that comprises an isolated viral connector protein polypeptide having an amino terminus and a carboxy terminus, and (2) either or both of (i) at least one flexibility domain and (ii) at least one affinity/alignment domain, under conditions and for a time sufficient for specific binding of the analyte molecule to the affinity/alignment domain; and (b) determining, at one or a plurality of time points prior to the step of contacting and at one or a plurality of time points after the step of contacting, a conductance signal that results from the applied electrical potential, wherein an alteration in the conductance signal after the step of contacting relative to the conductance signal prior to the step of contacting indicates binding of the analyte molecule to the connector protein, and therefrom detecting presence of the analyte molecule. In a further embodiment the alteration in the conductance signal indicates binding of the analyte molecule to the affinity/alignment domain.

Turning to another embodiment of the present invention, there is provided a method for identifying an analyte, comprising (a) contacting a test solution containing the analyte molecule with a conductive channel-containing membrane which comprises a membrane layer and incorporated therein one or a plurality of isolated viral DNA-packaging motor connector proteins that are capable of forming an aperture through which conductance can occur when an electrical potential is applied across the membrane, and that each comprise a homododecamer of viral DNA-packaging motor connector protein polypeptide subunits, wherein each of said subunits comprises (1) an aperture domain that comprises an isolated viral connector protein polypeptide having an amino terminus and a carboxy terminus, and (2) either or both of (i) at least one flexibility domain and (ii) at least one affinity/alignment domain, under conditions and for a time sufficient for specific binding of the analyte molecule to the affinity/alignment domain; (b) determining, at one or a plurality of time points prior to the step of contacting and at one or a plurality of time points after the step of contacting, a conductance signal that results from the applied electrical potential and therefrom generating a conductance signal profile, wherein an alteration in the conductance signal after the step of contacting relative to the conductance signal prior to the step of contacting indicates binding of the analyte molecule to the connector protein; and (c) comparing the conductance signal profile from (b) to a reference conductance signal profile for the analyte, and therefrom identifying the analyte molecule. In certain further embodiments, the alteration in the conductance signal indicates binding of the analyte molecule to the affinity/alignment domain.

According to certain embodiments of the above described methods, the step of contacting is repeated one or a plurality of times. In certain embodiments the step of comparing comprises one or more of (i) comparing conductance signal amplitude from the conductance signal profile of (b) to conductance signal amplitude in the reference conductance signal profile for the analyte, and (ii) comparing conductance signal duration from the conductance signal profile of (b) to conductance signal duration in the reference conductance signal profile for the analyte. In certain embodiments of the above described methods, the applied electrical potential results in ionic migration along an electrochemical gradient in the aperture domain. In certain embodiments the analyte comprises a nucleic acid molecule. In certain embodiments the analyte comprises a nucleic acid molecule and the step of comparing comprises identifying at least one nucleotide that is present in the nucleic acid molecule. In certain embodiments the method comprises determining a nucleic acid sequence of the nucleic acid molecule. In certain embodiments the method comprises identifying a single nucleotide polymorphism in the nucleic acid molecule. In certain embodiments voltage gating is not present, which in certain embodiments is not present when the applied electrical potential is selected from (i) a potential that is between −100 mV and 100 mV, (ii) a potential that is between −400 mV and 400 mV, (iii) a potential that is between −300 mV and 300 mV, (iv) a potential that is between −200 mV and 200 mV, (v) a potential that is between −150 mV and 150 mV, (vi) a potential that is between −75 mV and 75 mV, and (vii) a potential that is between −50 mV and 50 mV. In certain embodiments of the just-described methods, the conductive channel-containing membrane is the conductive channel-containing membrane described above. In certain embodiments of the just-described methods, the conductive channel-containing membrane is made according to the methods described above. In certain embodiments of the just-described methods, the isolated viral DNA-packaging motor connector protein comprises the isolated protein as described above.

Yet another embodiment of this disclosure provides an optical channel membrane, comprising (a) a membrane layer, and (b) an isolated viral DNA packaging motor connector protein, said viral DNA packaging motor connector protein is labeled with at least one donor fluorophore and is incorporated into the membrane layer to form a aperture through which fluorescence excitation is captured when an analyte labeled with at least one acceptor fluorophore passes through the membrane layer.

In certain embodiments of this disclosure the optical channel membrane is also a conductive channel membrane, which comprises (a) a membrane layer, and (b) an isolated viral DNA packaging motor connector protein, said viral DNA packaging motor connector protein is labeled with at least one donor fluorophore and is incorporated into the membrane layer to form a aperture through which fluorescence detection is coupled with the current detection when (i) an analyte labeled with at least one acceptor fluorophore passes through the membrane; and (ii) an electrical potential is applied across the membrane.

In the embodiments that contain the optical channel membrane the connector protein is labeled by Quantum Dots (QDs), for example but not limited to QD525, Alexa Fluor™ 488, QD 655 or QD 705 Alexa Fluor™700. The analyte is labeled by the corresponding acceptor that is to be excited by said QDs. The examples of acceptor choices are, not limited to, Cy3™, Alexa Fluor™ 546, Tetramethylrhodamine, TAMRA™, Cy5.5, Alexa Fluor™ 700, IRDye® 700, or Alexa Fluor™ 750, Alexa Fluor™790, Dy750.

Another embodiment of this disclosure provide a method of making an optical channel membrane, comprising: (a) preparing dried amphipathic lipids on a solid substrate by contacting a first solution comprising amphipathic lipids and an organic solvent with the solid substrate and substantially removing the solvent; (b) resuspending the dried amphipathic lipids in a second solution that comprises an aqueous solvent, an osmotic agent and a plurality of isolated viral DNA-packaging motor connector protein subunit polypeptides that are capable of self-assembly into a homododecameric viral DNA-packaging motor connector protein, to obtain a membrane that comprises a lipid bilayer in which is incorporated the viral DNA-packaging motor connector protein; and (c) attaching FRET donors to either N or C terminus of the connector subunits under conditions and for a time sufficient for said connector protein to form an aperture through which fluorescence excitation occurs and is being captured when an analyte labeled with a corresponding acceptor passes through the membrane, thereby making an optical detection membrane.

This disclosure also provides a method of making an optical and conductive channel membrane for synchronous detection of both optical and electrical signals, comprising: (a) preparing dried amphipathic lipids on a solid substrate by contacting a first solution comprising amphipathic lipids and an organic solvent with the solid substrate and substantially removing the solvent; (b) resuspending the dried amphipathic lipids in a second solution that comprises an aqueous solvent, an osmotic agent and a plurality of isolated viral DNA-packaging motor connector protein subunit polypeptides that are capable of self-assembly into a homododecameric viral DNA-packaging motor connector protein, to obtain a membrane that comprises a lipid bilayer in which is incorporated the viral DNA-packaging motor connector protein; and (c) attaching FRET donors to either N or C terminus of the connector subunits under conditions and for a time sufficient for said connector protein to form an aperture through which (i) fluorescence excitation occurs and is being captured when an analyte labeled with a corresponding acceptor passes through the membrane; and (ii) conductance occurs when an electrical potential is applied across the membrane, thereby making an optical and conductive channel containing membrane.

These and other aspects and embodiments of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually.

BRIEF DESCRIPTION OF THE SEVERAL VIEWS OF THE DRAWINGS

FIG. 1 shows structure of the phi29 connector and DNA packaging motor. a, Side view of the phi29 connector showing the acidic (shaded), basic (stippled), and other (white) amino acids. (Simpson et al., *Acta Cryst D*57, 1260-1269 (2001), Guasch et al., *J. Mol. Biol.* 315, 663-676 (2002), Guo et al., *J. Nanosci. Nanotechnol.* 5, 856-863 (2005); b, Top view of the connector showing the diameter of the narrow part and wide part of the channel. c, Illustration of the entire phi29 DNA packaging motor showing DNA translocation through the connector. d-e, A TEM image of purified connectors with C-terminal modification before (c) and after (d) the array formation. f, Coomasie-blue stained SDS-gel showing connectors.

FIG. 2 shows an example of plasmid construction for over-expression of viral DNA-packaging motor protein connectors with C-terminal modification by two-step PCR to include 6-Gly flexibility domain and Strep-II tag affinity/alignment domain. a, The linker was attached to the 3' end of GP10 gene in the first PCR by a primer pair F1-R1. In a second PCR, amino acids were incorporated downstream using primer pair F1-R2, which contained NdeI and XhoI restriction sites, respectively. b, The second PCR product was digested with both NdeI and XhoI, and ligated into the NdeI/XhoI sites of the vector pET-21 a(+). c, Sequences of primers.

FIG. 10 shows translocation of a 35-bp DNA through conductive transmembrane channels formed by apertures of modified DNA-packaging motor protein connectors. a, A typical current trace recorded from the bilayer in the presence of 4 µM of DNA (low-pass filtered at a frequency of 10 kHz and acquired at sampling frequency of 200 kHz); b-c, Comparison of dwell time of channel blockades by the translocation of 35-bp dsDNA (b) and 5.5-kbp dsDNA (c). b-c, TMS buffer with 1 M NaCl, −75 mV.

DETAILED DESCRIPTION

Figure 3:
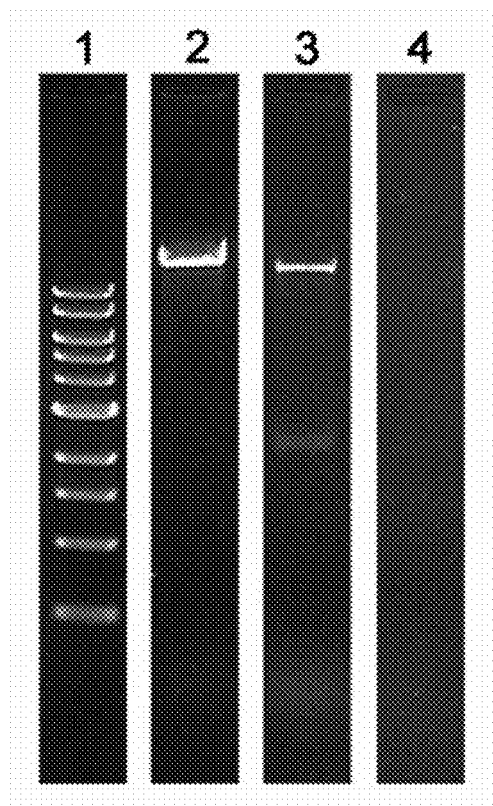
FIG. 3 shows DNA packaging activity of procapsid containing the reengineered phi29 gp10 viral DNA-packaging motor protein connector having C-terminal 6-Gly flexibility domain and Strep-II tag affinity/alignment domain. Lane 1, 1 kb DNA ladder; Lane 2, normal procapsid; Lane 3, procapsid with reengineered connector; Lane 4, negative control, DNA packaging without ATP.

Certain embodiments of the invention disclosed herein are based on the surprising discovery that an isolated double-stranded DNA bacteriophage DNA-packaging motor connector protein can, unexpectedly, be modified and incorporated into a membrane layer such as a phospholipid bilayer membrane, to form an aperture through which conductance can occur when an electrical potential is applied across the membrane, and through which a wide variety of analyte molecules including double-stranded DNA (dsDNA) can be translocated.

These viral DNA-packaging motor protein connectors have previously been characterized as components of dsDNA viral procapsid assembly involving protein-protein and protein-RNA interactions (e.g., Simpson et al., 2000 *Nature* 408: 745; Robinson et al., 2006 *Nucl. Ac. Res.* 34:2698), but prior to the present disclosure they have never been regarded as having the potential to act as integral components of lipid membranes. The herein described embodiments thus exploit heretofore unrecognized molecular attributes of such connector proteins to provide transmembrane aperture-forming biosensors having a number of advantageous properties.

An exemplary unmodified viral DNA-packaging motor connector protein from bacteriophage phi29 has been purified and its three-dimensional structure has been crystallographically characterized (e.g., Guasch et al., 1998 *FEBS Lett.* 430: 283; see also Marais et al., 2008 *Structure* 16:1267). DNA-packaging motor connector proteins of other dsDNA viruses (e.g., T4, lambda, P22, P2, T3, T5 and T7), despite sharing little sequence homology with, and differing in molecular weight from, the phi29 connector, exhibit significant underlying structural similarities (e.g., Bazinet et al., 1985 *Ann Rev. Microbiol.* 39:109-29). Accordingly, a number of preferred embodiments as described herein refer to the phi29 DNA-packaging motor connector protein (e.g., Genbank Acc. No. ACE96033, [SEQ ID NO:1]) and/or to polypeptide subunits thereof including fragments, variants and derivatives thereof (e.g., Acc. Nos. gi 29565762, gi 31072023, gi 66395194, gi 29565739, gi 157738604, [SEQ ID NOS:2-6]), but the invention is not intended to be so limited.

Instead, in certain other embodiments the use of an isolated viral DNA-packaging motor connector protein from other dsDNA viruses is contemplated, including without limitation the isolated viral DNA-packaging motor connector protein from any of phage lambda, P2, P3, P22, T3, T4, T5, SPP1 and T7, or another isolated dsDNA virus DNA-packaging motor connector protein (e.g., T4 (Acc. No. NP_049782) (Driedonks et al., 1981 *J Mol Biol* 152:641), lambda (Acc. Nos. gi 549295, gi 6723246, gi 15837315, gi 16764273) (Kochan et al., 1984 *J Mol Biol* 174:433), SPP1 (Acc. No. P54309), P22 (Acc. No. AAA72961)(Cingolani et al., 2002 *J Struct Biol* 139:46), P2 (Acc. No. NP_046757, P3 (Nutter et al., 1972 *J. Virol.* 10(3):560-2), T3 (Acc. No. CAA35152) (Carazo et al., 1986 *Jl. Ultrastruct Mol Struct Res* 94:105), T5 (Accession numbers AAX12078, YP_006980; AAS77191; AAU05287), T7 (Acc. No. NP_041995)(Cerritelli et al., 1996 *J Mol Biol* 285:299; Agirrezabala et al., 2005 *J Mol Biol* 347:895)) [SEQ ID NOS:7-20]).

Without wishing to be bound by theory, it is believed in this regard that like the phi29 DNA-packaging motor connector protein exemplified herein, these and other dsDNA virus packaging motor connector proteins, which have been substantially structurally characterized, can be modified according to the teachings herein to obtain an isolated DNA-packaging motor connector protein that can be incorporated into a membrane layer to form an aperture through which conductance can occur when an electrical potential is applied across the membrane. Accordingly, disclosure herein with respect to the phi29 connector protein is intended, for certain embodiments, to be illustrative of related embodiments that are contemplated using any of such other isolated dsDNA viral DNA-packaging motor connector proteins, which may be modified for use in such embodiments according to the teachings found herein.

As described in greater detail herein, isolated DNA-packaging motor connector protein polypeptides, including such polypeptides that have been artificially engineered to possess unprecedented properties of membrane incorporation (e.g., stable transmembrane integration in a membrane layer) and functional electroconductive transmembrane aperture formation, exhibit unpredicted and advantageously superior traits to provide a new class of electroconductive biosensors, and in particular embodiments, biosensors that are capable of translocating double-stranded DNA (dsDNA) across a membrane layer in response to an electrical potential. Certain embodiments therefore contemplate the use of these biosensors for DNA sequencing.

Briefly and by way of background, the genome of linear dsDNA viruses is packaged into a preformed procapsid (Black, *Ann Rev Microbiol* 43, 267-292 (1989), Guo, *Seminars in Virology (Editor's Introduction)* 5(1), 1-3 (1994), Guo et al., *Mol. Microbiol.* 64, 886-903 (2007), Rao et al., *Annu. Rev. Genet.* (2008). This entropically unfavorable process is accomplished by an ATP-driven motor (Guo et al. *J Mol Biol* 197, 229-236 (1987), Chemla et al., *Cell.* 122, 683-692 (2005), Hwang et al., *Biochemistry* 35, 2796-2803 (1996), Sabanayagam et al., *Biophys. J* 93, L17-L19 (2007)). In bacteriophage phi29, the motor uses one ATP to package 2 bp (Guo et al., 1987) or 2.5 bp of DNA (Moffitt et al., *Nature* 457, 446-4U2 (2009). The protein hub of this motor is a truncated cone structure, termed a connector (FIG. 1A), that allows dsDNA to enter during maturation and exit during infection (Kochan et al., *J Mol Biol* 174, 433-447 (1984), Rishovd et al., *Virology* 245, 11-17 (1998), Simpson et al., *Acta Cryst* D57, 1260-1269 (2001), Guasch et al., *J. Mol. Biol.* 315, 663-676 (2002), Agirrezabala et al., *J. Mol Biol.* 347, 895-902 (2005). The connector has a central channel (FIG. 1B) formed by twelve GP10 protein subunits. While the connector proteins of viruses share little sequence homology and vary in molecular weight, there is significant underlying structural similarity (Bazinet & King, *Ann. Rev. Microbiol.* 39, 109-129 (1985)). By demonstrating viral DNA packaging and procapsid conversion to infectious virions, phi29 DNA packaging motor was the first to be assembled in vitro in a defined system and remains one of the most well studied (Guo et al., *Proc. Natl. Acad. Sci. USA* 83, 3505-3509 (1986)). The motor utilizes six pRNA (packaging RNA) molecules (Guo et al., *Science* 236, 690-694 (1987), Guo et al., *Mol. Cell.* 2, 149-155 (1998), Zhang, et al., *Mol. Cell.* 2, 141-147 (1998), Shu et al., *EMBO J.* 26, 527-537 (2007)) to gear the machine (FIG. 1c).

As described herein for the first time, phi29 and other isolated dsDNA viral DNA-packaging motor protein connectors, including engineered and mutated versions thereof such as fusion proteins that retain their aperture domain and comprise either or both of an affinity/alignment domain and a flexibility domain, may be usefully incorporated into membrane layers to form apertures permitting their use as conductive channels when an electrical potential is applied across the membrane. Modified isolated double-stranded DNA virus DNA-packaging motor protein connectors such as the phi29 connector may be engineered to have desired structures for use in the presently disclosed embodiments (Jiminez et al., 1986 *Science* 232:1113: Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450: 176 (2007); Qian et al., *Nature* 450:259 (2007)), where protein crystallographic structural data are readily available (e.g., Simpson et al., *Acta Cryst* D57, 1260-1269 (2001), Guasch et al., *J. Mol. Biol.* 315, 663-676 (2002), Cai et al., *Nanomedicine* 4, 8-18 (2008), Guo et al., *J. Nanosci. Nanotechnol.* 5, 856-863 (2005). Furthermore, the procedures for large scale production and purification of phi29 connector have been developed (Guo et al., 2005; Ibanez et al., *Nucleic Acids Res.* 12, 2351-2365 (1984), Robinson et al., *Nucleic Acids Res.* 34, 2698-2709 (2006), Xiao et al., *ACS Nano* 3, 100-107 (2009).

Embodiments described herein will accordingly find use in a variety of molecular analytical contexts, including, for example, sensitive detection and characterization of chemical and biochemical analytes for biomedical, clinical, industrial, chemical, pharmaceutical, environmental, forensic, national security, toxicological and other purposes, including any situation where rapid, specific and exquisitely sensitive detection and/or characterization of an analyte (e.g., preferably a soluble analyte that is provided in solution) may be desired. Expressly contemplated are embodiments in which the presently disclosed compositions and methods are used for DNA sequencing as described in greater detail below, including dsDNA sequencing, high-throughput DNA sequencing, genomics, SNP detection, molecular diagnostics and other DNA sequencing applications.

Exemplary analytes thus include nucleic acids such as DNA and RNA (including dsDNA and dsRNA), including for the detection and identification of single nucleotide polymorphisms (SNPs) and/or mutations in such nucleic acids, and/or nucleic acid sequence determination. Other exemplary analytes that may be detected and/or characterized using the herein described compositions and methods include other biopolymers (e.g., proteins, glycoproteins, peptides, glycopeptides, oligosaccharides, polysaccharides, lipids, glycolipids, phospholipids, etc.) and other biomolecules (e.g., soluble mediators, cofactors, vitamins, bioactive lipids, metabolites, and the like), drugs and other pharmaceutical and pharmacological agents, including natural and synthetic compounds, food and cosmetics agents such as flavorants, odorants, preservatives, antioxidants, antimicrobial agents, stabilizers, carriers, excipients, modifying agents and the like, natural and synthetic toxins, dyes, and other compounds.

Accordingly and in certain embodiments, any analyte for which detection and/or characterization is desired may be used, where it will be recognized from the disclosure herein that the analyte is preferably soluble in a solvent that does not compromise the integrity of the particular membrane layer in which the isolated viral DNA-packaging motor connector protein is incorporated to form an aperture through which conductance can occur when an electrical potential is applied across the membrane. Analyte selection may thus vary as a function of the composition of the particular membrane layer being used, which may therefore influence solvent selection. Those skilled in the art will be familiar with criteria to be employed for selecting a solvent that is compatible with a membrane layer of any particular composition. In preferred embodiments, the membrane layer comprises a phospholipid bilayer and the solvent in which the analyte is provided comprises an aqueous solvent, e.g., a solvent that comprises water.

The presently disclosed compositions and methods may include in certain embodiments the practice of measuring electrical conductance, across a membrane layer in which the herein-described isolated viral DNA-packaging motor connector protein is incorporated, by adapting established electrophysiology instrumentation and methodologies. For example, and as described in greater detail below, modifications may be made to patch-clamp or planar membrane techniques for generating transmembrane potentials and measuring conductance across such membranes. Exemplary descriptions of such methodologies may also be found, for example, in Kasianowicz et al., 1996 *Proc Nat. Acad. Sci USA* 93:13770; Gu et al., 1999 *Nature* 398:686; Kasianowicz et al., 2001 *Anal. Chem.* 73:2268; Henrickson et al., 2000 *Phys. Rev. Lett.* 85:3057; Hromada et al., 2008 *Lab Chip.* 8:602; Robertson et al., 2007 *Proc. Nat. Acad. Sci. USA* 104:8207; U.S. Pat. Nos. 6,267,872; 6,746,594; and 6,936,433. Those familiar with the art will appreciate general methodologic approaches from these and similar references, and it will be further understood that advantages as described herein may be derived in part from the present disclosure, for the first time, of novel conductive channel-containing membranes that comprise an incorporated isolated viral DNA-packaging motor connector protein that forms an aperture having a larger lumen than many heretofore described protein nanopores, and that functions as a conductive channel across a wide range of applied electrical potentials without undesirable interruptions in conductivity due to voltage gating behavior, which is seen with many previously described protein nanopore channels. Thus, for example by way of illustration and not limitation, using known electrophysiology methodologies such as those referenced above and described herein, conductance occurs in the presently disclosed conductive channel-containing membrane without voltage gating when an electrical potential is applied that may in selected embodiments be between −100 mV and 100 mV, between −400 mV and 400 mV, between −300 mV and 300 mV, between −200 mV and 200 mV, between −150 mV and 150 mV, between −75 mV and 75 mV, between −50 mV and 50 mV, or within another voltage range as may vary according to the particular conductance conditions that are employed, as will be apparent to the skilled person based on the present disclosure.

Further, and according to non-limiting theory, the present conductive channel-containing membranes offer advantageous detection sensitivities that may derive in part from the aperture formed by the present viral DNA-packaging motor protein connectors, and also provide advantageous analyte characterization capabilities that may derive in part from the stable membrane incorporation of a protein conductive channel that can be engineered or mutated to have desired functional properties such as any of a wide variety of analyte-accessible affinity interaction domains by which to engage analyte in a specific binding interaction.

For methods of detecting an analyte, these and related embodiments contemplate sensitivity that is obtained by observation of an altered (e.g., increased or decreased in a statistically significant manner) level of conductance through the aperture in the conductive channel-containing membrane across which electrical potential is applied, when the incorporated connector protein is engaged in a specific binding interaction with the analyte, relative to the level of conductance when no such specific binding interaction is present. Accordingly in certain preferred embodiments there is provided a method for detecting presence of an analyte molecule, comprising (a) contacting a test solution containing the analyte molecule with a conductive channel-containing membrane which comprises a membrane layer and incorporated therein one or a plurality of isolated viral DNA-packaging motor connector proteins that are capable of forming an aperture through which conductance can occur when an electrical potential is applied across the membrane, and that each comprise a homododecamer of viral DNA-packaging motor connector protein polypeptide subunits, wherein each of said subunits comprises (1) an aperture domain that comprises an isolated viral connector protein polypeptide having an amino terminus and a carboxy terminus, and (2) either or both of (i) at least one flexibility domain and (ii) at least one affinity/alignment domain, under conditions and for a time sufficient for specific binding of the analyte molecule to the affinity/alignment domain; and (b) determining, at one or a plurality of time points prior to the step of contacting and at one or a plurality of time points after the step of contacting, a conductance signal that results from the applied electrical potential, wherein an alteration in the conductance signal after the step of contacting relative to the conductance signal prior to the step of contacting indicates binding of the analyte molecule to the connector protein, and therefrom detecting presence of the analyte molecule. In certain related further embodiments, the alteration in the conductance signal indicates binding of the analyte molecule to the affinity/alignment domain.

By way of illustration and not limitation, the aperture formed by the membrane-incorporated connector protein is believed to be at least partially obstructed or occluded when analyte is present and is bound to the channel-conductive membrane, resulting in altered, and typically decreased, conductance across the membrane. In the absence of bound analyte, no such constraint is placed on conductance through the channel, such that altered levels of conductance may be readily detected when bound and unbound states of the analyte are observed. As shown below in the Examples, the present conductive channel-containing membrane is believed according to non-limiting theory to afford exquisite sensitivity in the detection of analyte by permitting observation of such an analyte binding-associated alteration in conductance at the level of a single analyte molecule binding to a single membrane-incorporated isolated viral DNA-packaging motor connector protein that has formed a conductive transmembrane aperture. In certain other embodiments, conductance signals may be detected from multiple conductive channels formed by multiple transmembrane apertures of the connectors described herein.

In certain conceptually related embodiments, information beyond the mere detection of the absence or presence of an analyte may be obtained, where a conductance signal profile is generated, for instance, by collecting a record that reflects the amplitude of conductance, including altered conductance as described herein at one or a plurality of time points, and the duration of conductance, including altered conductance as described herein, at one or a plurality of timepoints. Such a signal profile may reflect any number of properties of the analyte in the course of its interaction with the connector protein(s), for example, binding affinity and/or binding avidity (e.g., if the analyte is multivalent), and also potentially, physicochemical properties of the analyte such as relative molecular mass, charge, and/or hydrophobicity, which may vary as a function of the particular analyte, the particular connector protein, the membrane composition, the solvent conditions, the applied electrical potential, and other factors.

In certain particularly preferred embodiments, a reference conductance signal profile may be generated using an analyte of known molecular structure, to which reference profile a conductance signal profile that is generated by the interaction of a test solution containing an analyte for which structural information is desired can be compared.

Hence, in these and related embodiments there is provided a method for identifying an analyte, comprising (a) contacting a test solution containing the analyte molecule with a conductive channel-containing membrane which comprises a membrane layer and incorporated therein one or a plurality of isolated viral DNA-packaging motor connector proteins that are capable of forming an aperture through which conductance can occur when an electrical potential is applied across the membrane, and that each comprise a homododecamer of viral DNA-packaging motor connector protein polypeptide subunits, wherein each of said subunits comprises (1) an aperture domain that comprises an isolated viral connector protein polypeptide having an amino terminus and a carboxy terminus, and (2) either or both of (i) at least one flexibility domain and (ii) at least one affinity/alignment domain, under conditions and for a time sufficient for specific binding of the analyte molecule to the affinity/alignment domain; (b) determining, at one or a plurality of time points prior to the step of contacting and at one or a plurality of time points after the step of contacting, a conductance signal that results from the applied electrical potential and therefrom generating a conductance signal profile, wherein an alteration in the conductance signal after the step of contacting relative to the conductance signal prior to the step of contacting indicates binding of the analyte molecule to the connector protein; and (c) comparing the conductance signal profile from (b) to a reference conductance signal profile for the analyte, and therefrom identifying the analyte molecule.

In certain further embodiments the alteration in the conductance signal indicates binding of the analyte molecule to the affinity/alignment domain. In any of the above described methods for detecting an analyte and for identifying an analyte, the step of contacting may be repeated one or a plurality of times, for instance, to generate a conductance signal profile. As noted above, comparison of a reference conductance signal profile for a known analyte to a test conductance signal profile for a test analyte may permit identification of the test analyte, an approach that may be employed, for example, in the characterization of nucleic acid molecules, such as identifying one or more single nucleotide polymorphisms in a nucleic acid molecule, or sequencing a nucleic molecule (including dsDNA) by determining a series of characteristic alterations in conductance as a linear DNA molecule is translocated through the aperture. In these and related embodiments it will be appreciated that based on the disclosure herein, the skilled person can, readily and without undue experimentation, determine conditions (e.g., selection of membrane, connector protein, solution conditions, applied electrical potential, etc.) under which a reference conductance signal profile can be generated, and therefrom generate a test conductance signal profile to which it can be compared.

Thus in certain embodiments the step of comparing comprises one or more of (i) comparing conductance signal amplitude from the test conductance signal profile to conductance signal amplitude in the reference conductance signal profile for the analyte, and (ii) comparing conductance signal duration from the test conductance signal profile to conductance signal duration in the reference conductance signal profile for the analyte. In certain embodiments, for example those in which complete or partial translocation of the analyte through the aperture is achieved, the applied electrical potential may result in ionic migration along an electrochemical gradient in the aperture domain. Thus in certain related embodiments of the instant methods, the analyte comprises a nucleic acid molecule, and in certain other related embodiments the step of comparing comprises identifying at least one nucleotide that is present in the nucleic acid molecule, which method in certain further embodiments comprises determining a nucleic acid sequence of the nucleic acid molecule.

It will be appreciated that certain preferred embodiments as described herein relate to an isolated DNA-packaging motor connector protein that comprises a dodecamer of chimeric or fusion polypeptide subunits, i.e., a non-naturally occurring polypeptide that is the product of recombinant genetic engineering techniques with which those skilled in the art will be familiar. In these and related embodiments, the fusion polypeptide comprises (i) an aperture domain, which may be all or an aperture-forming portion of a double-stranded DNA virus DNA-packaging motor protein connector polypeptide such as those discussed above and elsewhere herein (e.g., any polypeptide set forth in SEQ ID NOS:1-20 or other related DNA-packaging motor protein polypeptide, including variants, fragments and derivatives); and (ii) either or both of at least one flexibility domain and at least one affinity/alignment domain. Exemplary connectors may comprise homododecamers of viral DNA-packaging motor protein connector polypeptide subunits such as those having the amino acid sequences set forth in SEQ ID NOS:31-35 and 41-45.

Typically, the flexibility domain and/or the affinity/alignment domain may be present as a peptide sequence attached to the C-terminus and/or the N-terminus of the aperture domain, but the invention is not intended to be so limited and also contemplates inclusion of the flexibility and/or affinity/alignment domains at other locations within the connector polypeptide sequence. As noted elsewhere herein, detailed crystallographic structural data are available for the instant viral DNA-packaging motor protein connector polypeptides, and sophisticated three-dimensional structural protein modeling software programs are well known in the art for predicting the effects of structural modifications to proteins.

According to non-limiting theory, isolated DNA-packaging motor connector proteins as disclosed herein may be stabilized for retention and functional incorporation in membrane layers such as phospholipid bilayers, by modifying those portions of the connector polypeptides that interact with, respectively, hydrophilic phospholipid polar head groups and hydrophobic phospholipid fatty acyl chains, in a manner that energetically favors integration of the connector in the membrane to form a transmembrane aperture. Compositions and methods for introducing proteins to membranes, and for determining their incorporation into membranes, and further for ascertaining their disposition in the membranes as integral or transmembrane proteins, are known in the art and exemplified herein, as also are methodologies for determining functional incorporation of such proteins as electroconductive transmembrane channels.

Hence, and as presented herein, for example, a C-terminal modification comprising a flexibility domain of uncharged amino acids such as 4, 5, 6, 7, 8, 9, 10, 11, 12, 13, 14, 15, 16, 17, 18 or more contiguous uncharged amino acids (e.g., $Gly_6$, SEQ ID NO:23), and C-terminally attached thereto an affinity/alignment domain such as a peptide of formula I:

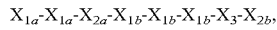  [I]

wherein each $X_{1a}$ is independently either any uncharged amino acid or no amino acid, each $X_{1b}$ is independently any uncharged amino acid, $X_{2a}$ is a positively charged amino acid selected from lysine, arginine and histidine, $X_3$ is a negatively charged amino acid selected from glutamic acid and aspartic acid, and $X_{2b}$ is a positively charged amino acid selected from lysine, arginine and histidine, for example, the peptide WSHPQFEK (SEQ ID NO:22) sometimes referred to as a "Strep-II" tag, is believed advantageously to influence the physicochemical properties of a dsDNA viral DNA-packaging motor protein connector in a manner that favors its retention as a transmembrane channel in a lipid bilayer, and that also advantageously exposes the tag to the surrounding milieu for interaction with solutes such as analytes. Thus, for instance and as a non-limiting illustrative example, under suitable conditions such as are provided by a buffered solution at or near physiological pH and with an electrical potential applied across the membrane, charge interactions may favor engagement of DNA in solution by the conductive channel and electrodiffusive forces may promote DNA translocation through the conductive channel aperture, which as noted herein can accommodate dsDNA.

The aperture domain may thus be provided by any dsDNA viral DNA-packaging motor protein connector polypeptide as described herein, and from available structural characterization of such proteins in view of the present disclosure regarding membrane incorporation of the modified connectors and their functional testing both for membrane integration and for establishment of an aperture through which conductance can occur when a membrane potential is applied, it will be appreciated that an aperture-forming portion includes a sufficient portion of such connector polypeptide subunits as may be needed for an assembled connector to exhibit these properties. As noted above, in certain embodiments a flexibility domain of about 4-18 contiguous uncharged amino acids may be advantageously fused to a viral DNA-packaging motor protein connector sequence as provided herein.

As also noted above, an affinity/alignment domain may be any peptide or polypeptide domain that can be fused to the viral DNA-packaging motor protein connector polypeptide subunit sequence, with or without an intervening flexibility domain being present, that promotes retention of the connector in the membrane layer and/or that provides an affinity interaction domain such as a receptor, ligand, binding site, counter-receptor or the like, which may be used to engage in specific binding of an analyte and/or to encourage analyte interaction with the conductive channel and/or both.

An exemplary affinity/alignment domain described for use herein in certain embodiments is the "Strep-II" peptide tag, WSHPQFEK [SEQ ID NO:22], by way of non-limiting example situated in a fusion protein construct as a C-terminal affinity tag, (e.g., Schmidt et al., *Protein Eng.* 1993; 6:109-22; Schmidt et al., *J. Mol. Biol.* 1996; 255:753-6.) or any of a number of other known peptide or polypeptide or other structures that have been identified as being capable of participating in specific affinity binding interactions with a cognate binding partner, such as, e.g., an antibody or an antigen-binding portion thereof (as also described below), the "AviD" tag having the sequence DRATPY [SEQ ID NO:40] (Gaj et al., 2007 *Prot. Expr. Purif.* 56:54), glutaredoxin-2 (Lundberg et al., 2006 *Prot Expr Purif* 45:37), or other known moieties such as avidin, streptavidin, lectins, antibodies, receptors, cell adhesion molecule recognition components, lectins, metal ion-binding polypeptides (e.g., polyhistidines such as hexa-histidine or a polypeptide tag of 3, 4, 5, 7, 8, 9, 10, 11 or 12 contiguous histidine residues), a polyarginine polypeptide of 3, 4, 5, 6, 7, 8, 9, 10, 11 or 12 contiguous arginine residues, a FLAG peptide tag, a Myc peptide tag having an antibody-defined epitope, glutathione-S-transferase (GST), maltose binding protein, immunoglobulin constant-region-binding *S. aureus* protein A or protein G, HIV Tat peptide (e.g., SEQ ID NO:39), a phage-displayed peptide that specifically binds an affinity ligand, an aptamer, or any other of a large number of well known affinity-interacting molecules that are known to the art, such as those described in the references cited herein. Other receptors, binding domains, ligands, counterreceptors and the like, all or parts of which may be used to produce affinity/alignment domains, include those disclosed in WO/2005/097997, WO/2002/056910, WO/2005/017148, and WO/2005/037989. Certain embodiments contemplate viral DNA-packaging motor connector proteins as provided herein that further comprise a detectable label, which, it will be appreciated, may be any of a wide variety of chemical, biochemical, radiochemical or nanomolecular moieties that permits detection using established techniques and instrumentation. Exemplary detectable labels are known in the art and include those described in WO/2007/075253 and US/2008/0176209.

As described in greater detail in the examples below, according to certain preferred embodiments the presently described conductive channel-containing membrane may be formed by incorporating the isolated viral DNA-packaging motor connector protein as provided herein, including connectors comprised of polypeptide subunits which comprise fusion proteins having an aperture domain and either or both of a flexibility domain and an affinity/alignment domain as described herein, into a liposomal membrane. The membrane typically comprises amphipathic lipids such as phospholipids (e.g., one or more of phosphatidylserine, phosphatidylethanolamine, phosphatidylcholine, phosphatidylinositol, phosphatidylglycerol, cardiolipin, 1,2-diphytanoyl-sn glycerol-3-phosphocholine, 1,2-dioleoyl-sn-glycero-3-phosphocholine, or other phospholipids with which the skilled artisan will be familiar), which tend to form bilayers when exposed under appropriate conditions to an aqueous milieu.

It will be appreciated that as described below, viral DNA-packaging motor protein connectors may be effectively incorporated into membranes by first providing amphipathic lipids from which solvent (e.g., an organic solvent such as one or more of chloroform, methanol, ethanol, n-propanol, isopropanol, n-butanol, isobutanol, pyridine, diisopropyl ether) has been substantially removed (e.g., such that little or no residual solvent can be detected by visual inspection, and preferably such that the lipid preparation is regarded as dry), and then resuspending the dried amphipathic lipids in a solution that comprises an aqueous solvent, an osmotic agent, and a plurality of isolated viral DNA-packaging motor protein connector subunit polypeptides that are capable of self-assembly into homododecameric connector proteins. Without wishing to be bound by theory, it is believed that the inclusion of the osmotic agent advantageously facilitates functional DNA-packaging motor connector incorporation into the membrane as conductive channels, by influencing the formation and size of, and/or intermolecular dynamics within, substantially spherical liposomes, although it is recognized that other methods for producing conductive channel-containing membranes should not be excluded. Non-limiting examples of osmotic agents that may be used in these and related embodiments include sucrose or other disaccharides, glycerol, mannitol and dextran.

In certain embodiments the liposome comprising the conductive channel-containing membrane may be used in liposomal form, for example, as a vehicle for delivery to cells in vitro or in vivo of nucleic acid molecules that have been concentrated or accumulated in the liposome, such as by electric potential-driven translocation, against the nucleic acid concentration gradient that would otherwise limit the nucleic acid concentration that can be achieved according to recognized equilibrium principles, through the connector apertures, to obtain nucleic acid-containing liposomes. Such liposomes may advantageously find use as therapeutic agents, instance in gene therapy and related strategies. A wide range of formulations are available for in vitro and in vivo therapeutic administration of nucleic acid-containing liposomes, and may be modified for use with liposomes produced according to the present disclosure. See, e.g., WO/2002/034236; WO/2002/036767; WO/2003/094963; WO/2005/034979; WO/2005/120461; WO/2000/03683; Lasic, *Liposomes in Gene Delivery*, 1997, CRC Press, Boca Raton, Fla.; WO 96/40964; WO 1998/51278; WO 2009/086558; US 2007/0042031; US 2006/0240093; US 2006/0083780; US 2004/0142025. Multilamellar and unilamellar liposomes are contemplated, with unilamellar liposomes being preferred in certain embodiments.

Also contemplated are embodiments in which the membrane-bound compartments defined by the presently described conductive channel-containing membrane may be advantageously employed as bioreactors. As will be appreciated by those skilled in the art, according to the present teachings the herein described conductive channel may be used to selectively translocate any of a large number of analytes, biomolecules, synthetic small molecules, ionic species and/or other solutes, depending on the properties of such compounds and of the particular conductive channel being employed (e.g., the nature of the affinity/alignment domain, the connector structure, the membrane composition, the connector orientation, the applied potential, etc.). Accordingly, within the membrane-bound compartment, which may be liposomal or nanoparticulate or one side of a planar membrane within a suitable apparatus, one or more desired molecular species can be accumulated, (e.g., at desired concentrations that may be electrodiffusively accumulated against a concentration gradient that would otherwise limit the concentrations attainable as a function of equilibrium dynamics) under conditions that favor a desired biomolecular or biochemical reaction such as a reaction useful for nucleic acid sequencing, SNP determination, nucleic acid amplification, nucleic acid synthesis, ligation or cleavage, macromolecular assembly, analyte detection or any other desired biochemical or synthetically engineered bioreaction.

As also described herein, certain embodiments contemplate incorporation of the herein described isolated viral DNA-packaging motor protein connectors into membrane layers to form liposomes, which may then donate membrane-integrated connectors to planar membrane systems, such as planar bilayer membrane (BLM) systems, by way of artificial membrane fusion manipulations according to art-known methodologies. Accordingly, conductive channel-containing membranes as described herein for the first time may be configured as desired for a particular purpose and/or to accommodate use with certain instrumentation, including but not limited to liposomal and/or nanoparticle (including carrier particle) delivery, planar membrane layers, microfluidic chambers, micropore and nanopore electroconductivity chambers, patch-clamp apparatus, fluorescence labeled analyte detection/characterization, and any other configuration compatible for use with the instant conductive channel-containing membrane as may be adapted based on the present disclosure and in view of knowledge in the art. As also described elsewhere herein, certain preferred embodiments contemplate the use of the present conductive channel-containing membrane for nucleic acid sequencing and SNP identification, including DNA sequencing and preferably including dsDNA sequencing, and in particular embodiments including real-time fingerprinting of dsDNA as it is translocated through the presently described conductive channel, by potential-driven translocation accompanied by detection and recording of altered conductance amplitude and/or duration over a plurality of time points to generate a conductance profile that can be compared to a reference conductance profile. In certain embodiments, an independent optical detection of dsDNA or a synchronous optical and electrical detection of DNA translocation is achieved by the combination of both conductance and optical single molecule detection system.

Antibodies. As noted above, also contemplated by certain embodiments of the present invention are affinity/alignment domains that comprise an antibody, including anti-analyte binding molecules that are peptides, polypeptides and other molecules that specifically bind to an analyte the detection and/or analysis of which is desired. Such binding molecules can be used in a method for detecting presence of an analyte, or in a method for identifying an analyte (for example, in a test solution), as described herein. An antibody, or another affinity/alignment domain as provided herein, is said to specifically bind to a particular cognate antigen or analyte (e.g., the analyte of interest) if it reacts (e.g., binds) at a detectable level with the antigen/analyte but does not react detectably with structurally distinct or unrelated molecules. Preferred binding molecules thus include antibodies, which may be, for example, polyclonal, monoclonal, single chain, chimeric, humanized, anti-idiotypic, or CDR-grafted immunoglobulins, or antigen-binding fragments thereof, such as proteolytically generated or recombinantly produced immunoglobulin F(ab')$_2$, Fab, Fab', Fv, and/or Fd fragments, single domain antibodies ("dAbs"; Holt et al., 2003 *Trends Biotech.* 21:484) and diabodies (Hudson et al., 1999 *J. Immunol. Meth.* 231: 177). An antibody according to the present invention may belong to any immunoglobulin class, for example IgG, IgE, IgM, IgD, or IgA. It may be obtained from or derived from an animal, for example, fowl (e.g., chicken) or a mammal, which includes but is not limited to a mouse, rat, hamster, rabbit, or other rodent, a cow, horse, sheep, goat, camel, human, or other primate. The antibody may be an internalizing antibody, or the antibody may be modified so that it may be easily transported across a cell membrane.

For purposes of identifying and preparing a desired antibody or affinity/alignment domain as provided herein, the binding properties of an antibody (used here in exemplary and non-limiting fashion as illustrative of affinity/alignment domains) to its specific antigen (used here in exemplary and non-limiting fashion as illustrative of analytes) may generally be assessed using conventional immunodetection methods including, for example, an enzyme-linked immunosorbent assay (ELISA), immunoprecipitation, radioimmunoassays, immunoblotting and the like, which may be readily performed by those having ordinary skill in the art. A skilled artisan will also be familiar with such immunodetection methods which, when used to detect an antibody that binds to a conformational epitope of an antigen/ligand, may preferably avoid any reagent or condition which could potentially denature the antigen and thus alter or destroy the ligand conformational epitope.

Methods well known in the art and described herein may be used to generate antibodies, including polyclonal antisera or monoclonal antibodies, that are specific for a particular antigen as may be desired. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species (see, e.g., Morrison et al., *Proc. Natl. Acad. Sci. USA*, 81:6851-55 (1984); Shin et al., *Methods Enzymol.* 178:459-76 (1989); Walls et al., *Nucleic Acids Res.* 21:2921-29 (1993); U.S. Pat. No. 5,482,856). Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions (see, e.g., Jones et al., *Nature* 321:522-25 (1986); Riechmann et al., *Nature* 332:323-27 (1988); Padlan et al., *FASEB* 9:133-39 (1995); Chothia et al., *Nature,* 342:377-383 (1989); Bajorath et al., *Ther. Immunol.* 2:95-103 (1995); EP-0578515-A3). Fragments of these molecules may be generated by proteolytic digestion, or optionally, by proteolytic digestion followed by mild reduction of disulfide bonds and alkylation. Alternatively, such fragments may also be generated by recombinant genetic engineering techniques (e.g., Harris, W. J., Adair, J. R., (*Eds.*) 1997 Antibody Therapeutics, CRC Press, Boca Raton, Fla.).

An antibody that is immunospecific (or an affinity/alignment domain that is specific) or that specifically binds to a cognate antigen (or analyte) as provided herein reacts at a detectable level with the antigen/analyte and not with molecules having distinct or unrelated structures, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinity of an antibody for its cognate antigen is also commonly expressed as a dissociation constant $K_D$, and an antibody specifically binds to the antigen if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of binding partners or antibodies can be readily determined using conventional techniques, for example, those described by Scatchard et al. (*Ann. N.Y. Acad. Sci. USA* 51:660 (1949)) or by surface plasmon resonance (BIAcore, Biosensor, Piscataway, N.J.). See, e.g., Wolff et al., *Cancer Res.* 53:2560-2565 (1993), or may be determined according to other methodologies as described herein.

Antibodies may generally be prepared by any of a variety of techniques known to those skilled in the art. See, e.g., Harlow et al., *Antibodies: A Laboratory Manual*, Cold Spring Harbor Laboratory (1988). In one such technique, an animal is immunized with an immunogenic form of the antigen/analyte, for instance, as a hapten on a suitable carrier according to established methodologies, as an antigen to generate polyclonal antisera. Suitable animals include, for example, rabbits, sheep, goats, pigs, cattle, and may also include smaller mammalian species, such as mice, rats, and hamsters, or other species.

An immunogen may comprise a purified or partially purified antigen or analyte of interest, or may be comprised of cells expressing the antigen (e.g., for an antigen which is a polypeptide or a polynucleotide or a metabolite) or to which the antigen has been introduced in a manner that enhances its immunogenicity. Peptide or polypeptide antigens may be generated using standard recombinant genetic methodologies, or by proteolytic cleavage of naturally occurring proteins, or may be chemically synthesized. Peptides may be isolated by techniques known in the art such as polyacrylamide gel electrophoresis or any of a variety of other separation methods such as liquid chromatography or other suitable methodologies.

For raising antibodies to antigens that are polypeptides or peptides, peptides useful as immunogens typically may have an amino acid sequence of at least 4 or 5 consecutive amino acids from the polypeptide sequence, and preferably have at least 6, 7, 8, 9, 10, 11, 12, 14, 15, 16, 18, 19 or 20 consecutive amino acids of the polypeptide sequence. Certain other preferred peptide immunogens may comprise 21-25, 26-30, 31-35, 36-40, 41-50 or more consecutive amino acids of a polypeptide sequence. Polypeptides or peptides useful for immunization may also be selected by analyzing the primary, secondary, and tertiary structure of a polypeptide antigen/analyte of interest according to methods known to those skilled in the art, in order to determine amino acid sequences more likely to generate an antigenic response in a host animal. See, e.g., Novotny, 1991 Mol. Immunol. 28:201-207; Berzofsky, 1985 Science 229:932-40; Chang et al. J. Biochem. 117:863-68 (1995); Kolaskar et al. Viology 261:31-42 (1999)). Preferably, the polypeptide or peptide comprises a sufficient number of amino acids to fold in a manner that approximates the conformation of the polypeptide/analyte in its biologically active form.

Immunogens may be prepared and animals immunized according to methods well known in the art. See, e.g., Harlow et al., Antibodies: A Laboratory Manual, Cold Spring Harbor Laboratory (1988). The immune response may be monitored by periodically bleeding the animal, separating the sera out of the collected blood, and analyzing the sera in an immunoassay, such as an ELISA or Ouchterlony diffusion assay, or the like, to determine the specific antibody titer. Once an antibody titer is established, the animals may be bled periodically to accumulate the polyclonal antisera. Polyclonal antibodies that bind specifically to the antigen may then be purified from such antisera, for example, by affinity chromatography using S. aureus protein A or protein G, which specifically binds to a constant region (heavy or light chain) of the antibody(ies) to be purified, or using the antigen/analyte, immobilized on a suitable solid support.

Monoclonal antibodies that specifically bind to the antigen, and hybridomas, which are immortal eukaryotic cell lines that produce monoclonal antibodies having the desired binding specificity, may also be prepared, for example, using the technique of Kohler and Milstein (Nature, 256:495-497; 1976, Eur. J. Immunol. 6:511-519 (1975)) and improvements thereto with which a skilled artisan will be familiar. An animal—for example, a rat, hamster, or a mouse—is immunized with an immunogen; lymphoid cells that include antibody-forming cells, typically spleen cells, are obtained from the immunized animal; and such cells may be immortalized by fusion with a selection agent-sensitized myeloma (e.g., plasmacytoma) cell fusion partner.

Monoclonal antibodies may be isolated from the supernatants of hybridoma cultures or isolated from a mouse that has been treated (e.g., pristane-primed) to promote formation of ascites fluid containing the monoclonal antibody. Antibodies may be purified by affinity chromatography using an appropriate ligand selected based on particular properties of the monoclonal antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody and the antigen/analyte for which specific antibodies are desired. Human monoclonal antibodies may be generated by any number of techniques with which those having ordinary skill in the art will be familiar.

Antibodies and other affinity/alignment domain polypeptides may also be identified and isolated using well known phage display techniques, for example, from human immunoglobulin phage libraries, from rabbit immunoglobulin phage libraries, and/or from chicken immunoglobulin phage libraries (see, e.g., Winter et al., 1994 Annu. Rev. Immunol. 12:433-55; Burton et al., 1994 Adv. Immunol. 57:191-280; U.S. Pat. No. 5,223,409; Huse et al., 1989 Science 246:1275-81; Schlebusch et al., 1997 Hybridoma 16:47-52 and references cited therein; Rader et al., J. Biol. Chem. 275:13668-76 (2000); Popkov et al., J. Mol. Biol. 325:325-35 (2003); Andris-Widhopf et al., J. Immunol. Methods 242:159-31 (2000)), or by other methodologies such as ribosome display (e.g., Hanes et al., 1998 Proc. Nat. Acad. Sci. USA 95:14130) or yeast display (e.g., Colby et al., 2004 Meths. Enzymol. 388:348) or the like. Antibodies isolated from non-human species or non-human immunoglobulin libraries may be genetically engineered according to methods described herein and known in the art, for example to optimize affinity, or to chimerize, or to "humanize" the antibody or fragment thereof.

In certain embodiments, a B cell from an immunized animal that is producing an antibody having desired specificity is selected and the light chain and heavy chain variable regions are cloned from the B cell according to molecular biology techniques known in the art (WO 92/02551; U.S. Pat. No. 5,627,052; Babcook et al., Proc. Natl. Acad. Sci. USA 93:7843-48 (1996)) and described herein. Preferably B cells from an immunized animal are isolated from the spleen, lymph node, or peripheral blood sample by selecting a cell that is producing an antibody that specifically binds to the antigen/analyte of interest. B cells may also be isolated from humans, for example, from a peripheral blood sample.

An antibody fragment may also be any synthetic or genetically engineered protein that acts like an antibody in that it binds to a specific antigen to form a complex. For example, antibody fragments include isolated fragments consisting of the light chain variable region; "Fv" fragments consisting of the variable regions of the heavy and light chains; recombinant single chain polypeptide molecules in which light and heavy variable regions are connected by a peptide linker (scFv proteins); and minimal recognition units consisting of the amino acid residues that mimic the hypervariable region. Such an antibody fragment preferably comprises at least one variable region domain. (see, e.g., Bird et al., Science 242: 423-26 (1988); Huston et al., Proc. Natl. Acad. Sci. USA 85:5879-5883 (1988); EP-B1-0318554; U.S. Pat. No. 5,132,405; U.S. Pat. No. 5,091,513; and U.S. Pat. No. 5,476,786).

In certain embodiments, an antibody that specifically binds to an antigen/analyte may be an antibody that is expressed as an intracellular protein. Such intracellular antibodies are also referred to as intrabodies and may comprise an Fab fragment, or preferably comprise a scFv fragment (see, e.g., Lecerf et al., Proc. Natl. Acad. Sci. USA 98:4764-49 (2001)). The framework regions flanking the CDR regions can be modified to improve expression levels and solubility of an intrabody in an intracellular reducing environment (see, e.g., Worn et al., J. Biol. Chem. 275:2795-803 (2000)). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., Mol. Cell Biol. 15:1182-91 (1995); Lener et al., Eur. J. Biochem. 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

The polynucleotides encoding an antibody or fragment thereof that specifically bind an antigen/analyte of interest, as described herein, may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be in a eukaryotic host cell, including yeast (e.g., *Saccharomyces cerevisiae, Schizosaccharomyces pombe*, and *Pichia pastoris*), fungi (e.g., *Neurospora* cells such as those of *N. crassa*) animal cells (including mammalian cells) or plant cells. Examples of suitable animal cells include, but are not limited to, myeloma, COS, CHO, or hybridoma cells. Examples of plant cells include tobacco, corn, soybean, and rice cells. Antibodies that specifically bind to the antigen/analyte of interest may be screened in assays for determining antibody affinity as described above, such as assays for determining Kd of an antibody.

Viral DNA-Packaging Motor Connector Protein Polypeptides

The polypeptides of the present invention include mutant viral DNA-packaging motor connector protein-derived polypeptides and fusion proteins having amino acid sequence regions that are identical or similar to sequences known in the art, or fragments or portions thereof. For example by way of illustration and not limitation, a mutant bacteriophage phi29 viral DNA-packaging motor connector protein [e.g., SEQ ID NO:1, Genbank Acc. No. ACE96033] or an engineered bacteriophage phi29 viral DNA-packaging motor connector protein-derived polypeptide fusion protein (e.g., SEQ ID NOS: 31-35 and 41-45) is contemplated for use according to the instant invention, as are polypeptides having at least 80% similarity (preferably a 80% identity) and more preferably 90% similarity (more preferably a 90% identity) to the reported polypeptide and still more preferably a 95% similarity (still more preferably a 95% identity) to the herein disclosed polypeptides and to portions of such polypeptides, wherein such portions of a mutant or engineered phi29 viral DNA-packaging motor connector protein-derived polypeptide generally contain at least 150, 175, 200, 225, 250, 275 or more amino acids and more preferably at least 240, 260, 280, 285, 290, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330 or more amino acids.

In like fashion, certain other embodiments contemplate other mutant double-stranded DNA bacteriophage virus motor connector proteins such as mutated forms of phage T4 DNA-packaging motor connector protein polypeptide [SEQ ID NO:7], lambda phage DNA-packaging motor connector protein polypeptide [SEQ ID NOS:8-11] (Accession numbers gi549295, gi6723246, gi15837315, gi16764273, phage SPP1 DNA-packaging motor connector protein polypeptide [SEQ ID NO:12] (Accession number P54309), phage P22 DNA-packaging motor connector protein polypeptide [SEQ ID NO:13] (Accession number AAA72961), phage P2 DNA-packaging motor connector protein polypeptide [SEQ ID NO:14] (Accession number NP_046757), phage P3 DNA-packaging motor connector protein polypeptide (Nutter et al., 1972 *J. Virol.* 10(3):560-2), phage T3 DNA-packaging motor connector protein polypeptide [SEQ ID NO:15] (Accession number CAA35152, phage T5 DNA-packaging motor connector protein polypeptide [SEQ ID NOS:16-19] (Accession numbers AAX12078, YP_006980; AAS77191; AAU05287), and phage T7 DNA-packaging motor connector protein polypeptide [SEQ ID NO:20] (Accession number NP_041995).

Certain embodiments of the present invention relate to viral DNA-packaging motor connector protein polypeptides, mutant viral DNA-packaging motor connector protein polypeptides and engineered viral DNA-packaging motor connector polypeptide fusion proteins, and certain embodiments relate to constructs encoding viral DNA-packaging motor connector proteins such as mutant viral DNA-packaging motor connector protein polypeptides and engineered viral DNA-packaging motor connector polypeptide fusion proteins, for example viral DNA-packaging motor connector protein fusion polypeptides containing a motor protein connector aperture domain as provided herein and also containing one or both of a flexibility domain and an affinity/alignment domain as also provided herein, and in particular to methods for making a conductive channel-containing membrane using polypeptide products of recombinant constructs encoding such proteins that are capable of self-assembly into a homododecameric viral DNA-packaging motor connector protein and that may be expressed, for example and in certain related embodiments, as fragments, analogs and derivatives of such polypeptides.

Variants, fragments, derivatives, truncations, and the like of such mutant viral DNA-packaging motor connector protein polypeptides are also contemplated and are discussed in greater detail below, including routine methodologies for their production, structural characterization (e.g., for the presence of an aperture domain and either or both of a flexibility domain and an affinity alignment domain as provided herein) and functional testing (e.g., for their aperture-forming properties when incorporated into lipid membranes, as also described herein). According to certain preferred embodiments, a mutant viral DNA-packaging motor connector polypeptide for use in the compositions and methods disclosed herein may comprise an amino acid sequence that has at least 80 percent, 85 percent, 90 percent, 95 percent, 96, 97, 98, 99 or greater percent sequence identity to a double-stranded DNA bacteriophage DNA-packaging motor connector protein polypeptide such as a viral DNA-packaging motor connector protein polypeptide subunit as provided herein, for example by way illustration and not limitation, a polypeptide that comprises the amino acid sequence set forth in any one of SEQ ID NOS:1-20, 31-35 and 41-45.

The terms "fragment," "derivative" and "analog" when referring to viral DNA-packaging motor connector proteins or polypeptides, refers to any mutant viral DNA-packaging motor connector protein-derived polypeptide described herein, or a fusion protein comprising such polypeptide, that retains essentially the same biological function or activity as such polypeptide. Thus, an analog includes a proprotein which can be activated by cleavage of the proprotein portion to produce an active viral DNA-packaging motor connector polypeptide, which in preferred embodiments may be incorporated into a membrane layer to form an aperture through which conductance can occur when an electrical potential is applied across the membrane and/or may be capable of self-assembly into a homododecameric viral DNA-packaging motor connector protein such as may form such an aperture to obtain a conductive channel-containing membrane.

A fragment, derivative or analog of a viral DNA-packaging motor connector protein-derived polypeptide described herein, including polypeptides or fusion proteins or domains or portions thereof encoded by the cDNAs referred to herein and for which nucleotide coding sequences may be known to the art and/or can be deduced from the polypeptide sequences disclosed herein, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mutant viral DNA-packaging motor connector protein-derived polypeptide, including amino acids that are employed for detection or specific functional alteration of the mutant or engineered viral DNA-packaging motor connector protein-derived polypeptide or a proprotein sequence. Such fragments, derivatives and analogs are deemed to be within the scope of those skilled in the art from the teachings herein.

As known in the art "similarity" between two polypeptides is determined by comparing the amino acid sequence and conserved amino acid substitutes thereto of the polypeptide to the sequence of a second polypeptide. Fragments or portions of the nucleic acids encoding polypeptides according to the presently disclosed embodiments may be used to synthesize full-length nucleic acids encoding a mutant or engineered viral DNA-packaging motor connector protein-derived polypeptide. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 *Nucl. Ac. Res.* 25:3389) which weights sequence gaps and sequence mismatches according to the default weightings provided by the National Institutes of Health/NCBI database (National Center for Biotechnology Information, Bethesda, Md.).

The term "isolated" means that the material is removed from its original environment (e.g., the natural environment if it is naturally occurring). For example, a naturally occurring nucleic acid or polypeptide present in a living animal or intact naturally occurring virus is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

As described herein, certain invention embodiments provide mutant or engineered viral DNA-packaging motor connector protein-derived polypeptides and fusion proteins encoded by nucleic acids that have the mutant or engineered viral DNA-packaging motor connector protein-derived polypeptide coding sequence fused in frame to an additional fusion polypeptide encoding sequence to provide for expression of a mutant or an engineered viral DNA-packaging motor connector protein-derived polypeptide sequence fused to an additional functional fusion polypeptide sequence that permits, for example by way of illustration and not limitation, detection, functional alteration, isolation and/or purification of the resulting fusion protein.

Such fusion proteins may permit functional alteration of a mutant or engineered viral DNA-packaging motor connector protein-derived polypeptide by containing additional polypeptide sequences that influence behavior of the fusion product, for example, by altering the availability of protein surface-exposed charged and/or hydrophobic amino acid side chains in such a manner as to alter (e.g., increase or decrease in a statistically relevant manner relative to an appropriate control) interactions with a membrane such as with amphipathic membrane components such as phospholipids in a membrane bilayer. According to non-limiting theory, in these and related embodiments the mutant or engineered viral DNA-packaging motor connector protein-derived fusion polypeptide may exhibit more stable incorporation into the membrane and/or may form an aperture through which conductance can occur when an electrical potential is applied across the membrane in a manner that provides an aperture having desirable properties, such as increased aperture dimensions and/or altered distribution of hydrophilic, hydrophobic, neutral and/or charged amino acid side chains and/or preservation of the conductive aperture structure despite truncation of the viral DNA-packaging motor connector protein sequence or addition of polypeptide domains (e.g., a flexibility domain or an affinity/alignment domain as provided herein) that are not found in the wild-type DNA-packaging motor connector protein.

Determination of the three-dimensional structures of representative polypeptides (e.g., mutant or engineered DNA-packaging motor connector protein subunits as provided herein, for instance, a polypeptide fusion protein having a flexibility domain and/or an affinity/alignment domain as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007). Some additional non-limiting examples of computer algorithms that may be used for these and related embodiments, such as for rational design of flexibility domains or affinity/alignment domains as provided herein, include Desktop Molecular Modeler (See, for example, Agboh et al., *J. Biol. Chem.*, 279, 40: 41650-57 (2004)), which allows for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488).

In one embodiment, the present invention provides truncated components (e.g., fragments of a mutant or engineered viral DNA-packaging motor connector protein-derived polypeptide) for use in a mutant or engineered viral DNA-packaging motor connector protein-derived polypeptide fusion protein, and in another embodiment the invention provides nucleic acids encoding a mutant or engineered viral DNA-packaging motor connector protein-derived polypeptide fusion protein having such truncated components.

A truncated molecule may be any molecule that comprises less than a full length version of the molecule, for example, a truncated viral DNA-packaging motor protein polypeptide subunit. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

In other preferred embodiments, truncated molecules are polypeptides that comprise less than the full length amino acid sequence of a particular protein or polypeptide component. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues. In certain particularly preferred embodiments truncated nucleic acid molecules may have a deletion of 3-75 contiguous nucleotides. In certain other particularly preferred embodiments truncated polypeptide molecules may have a deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, or 41-50 contiguous amino acids.

Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, Jan. 1985, 12-19); Smith et al. (*Genetic Engineering: Principles and Methods BioTechniques*, Jan. 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest. An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed by certain embodiments of the invention. For example, according to certain contemplated embodiments, sequences encoding Cys residues that are not desirable or essential for biological activity can be altered to cause the Cys residues to be deleted or replaced with other amino acids, preventing formation of incorrect or undesirable intramolecular disulfide bridges upon renaturation.

Modification of the polypeptide may be effected by any means known to those of skill in the relevant art. The preferred methods herein rely on modification of DNA encoding the fusion protein and expression of the modified DNA. DNA encoding one of the mutant or engineered viral DNA-packaging motor connector protein-derived polypeptide fusions discussed above may be mutagenized using standard methodologies, including those described below. For example, cysteine residues that may otherwise facilitate multimer formation or that may mediate interactions with reactive groups present on analytes being detected by the herein described conductive channel-containing membrane or that may promote particular molecular conformations, can be deleted from a polypeptide or replaced, e.g., cysteine residues that are responsible for undesired aggregate formation. If necessary, the identity of cysteine residues that contribute to such aggregate formation may be determined empirically, by deleting and/or replacing a cysteine residue and ascertaining whether the resulting protein forms aggregates in solutions containing physiologically acceptable buffers and salts. In addition, fragments of mutant or engineered viral DNA-packaging motor connector protein-derived polypeptide fusions may be constructed and used, which in certain preferred embodiments includes fragments that comprise a transmembrane aperture-forming portion of such polypeptides. Design, production and testing of such fragments may be achieved based on the present disclosure and using art-known methodologies, including, for example, computer-modeled polypeptide design, recombinant expression, functional incorporation into membrane layers, and conductance testing, as discussed herein.

Conservative substitutions of amino acids are well known and may be made generally without altering the biological activity of the resulting mutant or engineered viral DNA-packaging motor connector protein-derived polypeptide molecule. For example, such substitutions are generally made by interchanging within the groups of polar residues, charged residues, hydrophobic residues, small residues, and the like. If necessary, such substitutions may be determined empirically merely by testing the resulting modified protein for the ability to alter (i.e., increase or decrease in a statistically significant manner) e.g., dodecamer self-assembly, incorporation into a membrane layer, conductive aperture formation, and/or analyte detection, in in vitro assays, such as those described herein.

The present invention further relates to nucleic acids which hybridize to mutant or engineered viral DNA-packaging motor connector protein-derived polypeptide encoding polynucleotide sequences as provided herein, or their complements, as will be readily apparent to those familiar with the art, if there is at least 70%, preferably 80-85%, more preferably at least 90%, and still more preferably at least 95%, 96%, 97%, 98% or 99% identity between the sequences. The present invention particularly relates to nucleic acids which hybridize under stringent conditions to the mutant or engineered viral DNA-packaging motor connector protein-derived polypeptide encoding nucleic acids referred to herein. As used herein, the term "stringent conditions" means hybridization will occur only if there is at least 90-95% and preferably at least 97% identity between the sequences. The nucleic acids which hybridize to mutant or engineered viral DNA-packaging motor connector protein-derived polypeptide encoding nucleic acids referred to herein, in preferred embodiments, encode polypeptides which retain substantially the same biological function or activity (e.g., dodecameric self-assembly, incorporation into membrane layers, conductive aperture formation, ability to detect analyte) as the mutant or engineered viral DNA-packaging motor connector protein-derived polypeptides described herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

The nucleic acids of the present invention, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes a mutant or engineered viral DNA-packaging motor connector protein-derived polypeptide for use according to certain invention embodiments may contain sequence regions that are identical to portions of the viral DNA-packaging motor connector protein coding sequences known in the art, or may for such reasons have a different coding sequence, which, as a result of the redundancy or degeneracy of the genetic code, encodes the same regions of such a viral DNA-packaging motor connector protein polypeptide.

The nucleic acids which encode mutant or engineered viral DNA-packaging motor connector protein-derived polypeptides for use according to certain invention embodiments may include, but are not limited to: only the coding sequence for the mutant or engineered viral DNA-packaging motor connector protein-derived polypeptide; the coding sequence for the mutant or engineered viral DNA-packaging motor connector protein-derived polypeptide and additional coding sequence; the coding sequence for the mutant or engineered viral DNA-packaging motor connector protein-derived polypeptide (and optionally additional coding sequence) and non-coding sequence, such as introns or non-coding sequences 5' and/or 3' of the coding sequence for the mutant or engineered viral DNA-packaging motor connector protein-derived polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" or "polynucleotide encoding" a mutant or engineered viral DNA-packaging motor connector protein-derived polypeptide encompasses a nucleic acid which include's only coding sequence for a mutant or engineered viral DNA-packaging motor connector protein-derived polypeptide as well as a nucleic acid which includes additional coding and/or non-coding sequence(s).

Nucleic acids and oligonucleotides for use as described herein can be synthesized by any method known to those of skill in this art (see, e.g., WO 93/01286, U.S. application Ser. No. 07/723,454; U.S. Pat. No. 5,218,088; U.S. Pat. No. 5,175,269; U.S. Pat. No. 5,109,124). Identification of oligonucleotides and nucleic acid sequences for use in the presently disclosed embodiments involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

Host organisms include those organisms in which recombinant production of mutant or engineered viral DNA-packaging motor connector protein-derived polypeptide products encoded by the recombinant constructs of certain presently disclosed invention embodiments may occur, such as bacteria (for example, *E. coli*), yeast (for example, *Saccharomyces cerevisiae* and *Pichia pastoris*), insect cells and mammals, including in vitro and in vivo expression. Host organisms thus may include organisms for the construction, propagation, expression or other steps in the production of the compositions provided herein. Presently preferred host organisms are *E. coli* bacterial strains.

The DNA construct encoding the desired mutant or engineered viral DNA-packaging motor connector protein-derived polypeptide is introduced into a plasmid for expression in an appropriate host. In certain preferred embodiments, the host is a bacterial host. The sequence encoding the ligand or nucleic acid binding domain is preferably codon-optimized for expression in the particular host. Thus, for example, if a mutant or engineered viral DNA-packaging motor connector protein-derived polypeptide is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding a mutant or engineered viral DNA-packaging motor connector protein-derived polypeptide may also include DNA encoding a secretion signal, whereby the resulting peptide is a precursor protein. The resulting processed protein may be recovered from the periplasmic space or the fermentation medium.

In preferred embodiments, the DNA plasmids also include a transcription terminator sequence. As used herein, a "transcription terminator region" is a sequence that signals transcription termination. The entire transcription terminator may be obtained from a protein-encoding gene, which may be the same or different from the inserted mutant or engineered viral DNA-packaging motor connector protein-derived polypeptide encoding gene or the source of the promoter. Transcription terminators are optional components of the expression systems herein, but are employed in preferred embodiments.

The plasmids used herein include a promoter in operative association with the DNA encoding the protein or polypeptide of interest and are designed for expression of proteins in a suitable host as described above (e.g., bacterial, murine or human) depending upon the desired use of the plasmid. Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see Nakamura et al., *Cell* 18:1109-1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S. Pat. No. 4,952,496; and Studier et al., *Meth. Enzymol.* 185:60-89, 1990) and the TAC promoter.

The plasmids may optionally include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Amps), tetracycline resistance gene (Tcr) and the kanamycin resistance gene (Kang).

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol. Biol.* 184:99-105, 1985). In addition, the bacterial pelB gene secretion signal (Lei et al., *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99-105, 1985), as may also be a fusion domain comprising the *E. coli* YebF carrier protein (Zhang et al., 2006 *Nat. Biotechnol.* 24:100). Using the methods described herein, one of skill in the art can substitute secretion signals that are functional in yeast, insect or mammalian cells to secrete proteins from those cells.

Preferred plasmids for transformation of *E. coli* cells include the pET expression vectors (e.g., pET-11a, pET-12a-c, pET-15b; see U.S. Pat. No. 4,952,496; available from Novagen, Madison, Wis.). Other preferred plasmids include the pKK plasmids, particularly pKK 223-3, which contains the tac promoter (Brosius et al., *Proc. Natl. Acad. Sci.* 81:6929, 1984; Ausubel et al., *Current Protocols in Molecular Biology; U.S. Pat. Nos.* 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance gene with a kanamycin resistance gene. (Available from Pharmacia; obtained from pUC4K, see, e.g., Vieira et al. (*Gene* 19:259-268, 1982; and U.S. Pat. No. 4,719,179.) Baculovirus vectors, such as pBlueBac (also called pJVETL and derivatives thereof), particularly pBlueBac III (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. Other plasmids include the pIN-IIIompA plasmids (see U.S. Pat. No. 4,575,013; see also Duffaud et al., *Meth. Enz.* 153:492-507, 1987), such as pIN-IIIompA2.

Preferably, the DNA molecule is replicated in bacterial cells, preferably in *E. coli*. The preferred DNA molecule also includes a bacterial origin of replication, to ensure the maintenance of the DNA molecule from generation to generation of the bacteria. In this way, large quantities of the DNA molecule can be produced by replication in bacteria. Preferred bacterial origins of replication include, but are not limited to, the fl-ori and col E1 origins of replication. Preferred hosts contain chromosomal copies of DNA encoding T7 RNA polymerase operably linked to an inducible promoter, such as the lacUV promoter (see U.S. Pat. No. 4,952, 496). Such hosts include, but are not limited to, lysogens *E. coli* strains HMS174(DE3)pLysS, BL21(DE3)pLysS, HMS174(DE3) and BL21(DE3). Strain BL21(DE3) is preferred. The pLys strains provide low levels of T7 lysozyme, a natural inhibitor of T7 RNA polymerase.

The DNA molecules provided may also contain a gene coding for a repressor protein. The repressor protein is capable of repressing the transcription of a promoter that contains sequences of nucleotides to which the repressor protein binds. The promoter can be derepressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Preferred repressor proteins include, but are not limited to the *E. coli* lacI repressor responsive to IPTG induction, the temperature sensitive λ cI857 repressor, and the like. The *E. coli* lacI repressor is preferred.

In general, recombinant constructs of the subject embodiments will also contain elements necessary for transcription and translation. In particular, such elements are preferred where the recombinant expression construct containing nucleic acid sequences encoding mutant or engineered viral DNA-packaging motor connector protein-derived polypeptides is intended for expression in a host cell or organism. In certain embodiments of the present invention, cell type preferred or cell type specific expression of a mutant or engineered viral DNA-packaging motor connector protein-derived polypeptide encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters. Promoter regions have been identified in the genes of many eukaryotes including higher eukaryotes, such that suitable promoters for use in a particular host can be readily selected by those skilled in the art.

Inducible promoters may also be used. These promoters include MMTV LTR (PCT WO 91/13160), inducible by dexamethasone; metallothionein promoter, inducible by heavy metals; and promoters with cAMP response elements, inducible by cAMP. By using an inducible promoter, the nucleic acid sequence encoding a mutant or engineered viral DNA-packaging motor connector protein-derived polypeptide may be delivered to a cell by the subject invention expression construct and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed may be used when expression of a particular mutant or engineered viral DNA-packaging motor connector protein-derived polypeptide-encoding gene is desired in concert with expression of one or more additional endogenous or exogenously introduced genes.

In addition to the promoter, repressor sequences, negative regulators, or tissue-specific silencers may be inserted to reduce non-specific expression of mutant or engineered viral DNA-packaging motor connector protein-derived polypeptide encoding genes in certain situations, such as, for example, a host or host cell in which it may be desired transiently and/or cell type-specifically or tissue-specifically or site-specifically to alter transmembrane electroconductivity as part of an experimental or therapeutic strategy. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol Cell Biol* 17: 182-9, 1997; Gdula et al., *Proc Natl Acad Sci USA* 93:9378-83, 1996, Chan et al., *J Virol* 70: 5312-28, 1996; Scott and Geyer, *EMBO J* 14:6258-67, 1995; Kalos and Fournier, *Mol Cell Biol* 15:198-207, 1995; Chung et al., *Cell* 74: 505-14, 1993) and will silence background transcription.

Repressor elements have also been identified in the promoter regions of the genes for type II (cartilage) collagen, choline acetyltransferase, albumin (Hu et al., *J. Cell Growth Differ.* 3(9):577-588, 1992), phosphoglycerate kinase (PGK-2) (Misuno et al., *Gene* 119(2):293-297, 1992), and in the 6-phosphofructo-2-kinase/fructose-2,6-bisphosphatase gene. (Lemaigre et al., *Mol. Cell Biol.* 11(2):1099-1106.) Furthermore, the negative regulatory element Tse-1 has been identified in a number of liver specific genes, and has been shown to block cAMP response element-(CRE) mediated induction of gene activation in hepatocytes. (Boshart et al., *Cell* 61(5):905-916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well known techniques.

Other elements may be incorporated into the mutant or engineered viral DNA-packaging motor connector protein-derived polypeptide encoding constructs of the present invention. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary for, or that enhance, propagation in bacteria are incorporated. Such elements include an origin of replication, a selectable marker and the like.

As provided herein, an additional level of controlling the expression of nucleic acids encoding mutant or engineered viral DNA-packaging motor connector protein-derived polypeptide delivered to cells using the constructs of the present invention embodiments may be provided by simultaneously delivering two or more differentially regulated nucleic acid constructs. The use of such a multiple nucleic acid construct approach may permit coordinated regulation of viral DNA-packaging motor connector protein expression. Those familiar with the art will appreciate that multiple levels of regulated gene expression may be achieved in a similar manner by selection of suitable regulatory sequences, including but not limited to promoters, enhancers and other well known gene regulatory elements.

The present invention also relates in certain embodiments to vectors, and to constructs prepared from known vectors that include nucleic acids of the present invention, and in particular to "recombinant expression constructs" that include any nucleic acids encoding mutant or engineered viral DNA-packaging motor connector protein-derived polypeptides according to certain invention embodiments as provided herein; and to host cells which are genetically engineered with vectors and/or constructs of the invention. Mutant or engineered viral DNA-packaging motor connector protein-derived polypeptides can be expressed in virtually any host cell under the control of appropriate promoters, depending on the nature of the construct (e.g., type of promoter, as described above), and on the nature of the desired host cell (e.g., whether postmitotic terminally differentiated or actively dividing; e.g., whether the expression construct occurs in a host cell as an episome or is integrated into the host cell genome). Appropriate cloning and expression vectors for use with prokaryotic and eukaryotic hosts are described by Sambrook, et al., *Molecular Cloning: A Laboratory Manual*, Third Edition, Cold Spring Harbor, N.Y., (2001).

Typically, the constructs are derived from plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.; and others). Presently preferred constructs may be prepared that include a dihydrofolate reductase (DHFR) encoding sequence under suitable regulatory control, for promoting enhanced production levels of the mutant or engineered viral DNA-packaging motor connector protein-derived polypeptides, which levels result from gene amplification following application of an appropriate selection agent (e.g., methotrexate).

Generally, recombinant expression vectors will include origins of replication and selectable markers permitting transformation of the host cell, and a promoter derived from a highly-expressed gene to direct transcription of a downstream structural sequence, as described above. The heterologous structural sequence is assembled in appropriate phase with translation initiation and termination sequences. Thus, for example, the mutant or engineered viral DNA-packaging motor connector protein-derived polypeptide encoding nucleic acids as provided herein may be included in any one of a variety of expression vector constructs as a recombinant expression construct for expression in a host cell.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (2004 *Current Protocols in Molecular Biology*, John Wiley & Sons, Inc., Boston, Mass.); Sambrook et al. (2001 *Molecular Cloning*, Third Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); and elsewhere.

The DNA sequence in the expression vector is operatively linked to at least one appropriate expression control sequences (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a mutant or engineered viral DNA-packaging motor connector protein-derived polypeptide is described herein.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

As provided herein, in certain embodiments the vector may be a viral vector such as a retroviral vector. (Miller et al., 1989 *BioTechniques* 7:980; Coffin and Varmus, 1996 Retroviruses, *Cold Spring Harbor Laboratory Press*, NY.) For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present invention, an expression construct may comprise a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems which have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' of the coding genes, and the three coding genes gag, pol, and env. These three genes gag, pol, and env encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector producing cell lines have been developed because of safety concerns regarding the uses of retroviruses, including their use in expression constructs as provided by the present invention. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

"Retroviral vector construct" refers to an assembly which is, within preferred embodiments of the invention, capable of directing the expression of a sequence(s) or gene(s) of interest, such as mutant or engineered viral DNA-packaging motor connector protein-derived polypeptide encoding nucleic acid sequences. Briefly, the retroviral vector construct must include a 5' LTR, a tRNA binding site, a packaging signal, an origin of second strand DNA synthesis and a 3' LTR. A wide variety of heterologous sequences may be included within the vector construct, including for example, a sequence which encodes a protein (e.g., a desired supplementary gene or a replacement gene), or which is itself useful as a transcribed molecule (e.g., as a ribozyme or antisense sequence).

Retroviral vector constructs of the present invention may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning: A Laboratory Manual*, 2d ed., Cold Spring Harbor Laboratory Press, 1989; Kunkle, *PNAS* 82:488, 1985).

Suitable promoters for use in viral vectors generally may include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

As described above, the retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the mutant or engineered viral DNA-packaging motor connector protein-derived polypeptides or fusion proteins. Such retroviral vector particles then may be employed, to transduce eukaryotic cells, either in vitro or in vivo. The transduced eukaryotic cells will express the nucleic acid sequence(s) encoding the mutant or engineered polypeptide or fusion protein. Eukaryotic cells which may be transduced include, in preferred embodiments, smooth muscle cells (e.g., vascular smooth muscle cells including arterial smooth muscle cells and venous smooth muscle cells, gastrointestinal tract smooth muscle cells, respiratory tract smooth muscle cells, urogenital tract smooth muscle cells), fibroblasts, myofibroblasts, chondrocytes, pericytes, glial cells, glioma cells, macrophages, and endothelial cells, but the invention is not intended to be so limited such that cells to be transduced may in certain embodiments also include, for example, embryonic stem cells, as well as hematopoietic stem cells, hepatocytes, fibroblasts, circulating peripheral blood mononuclear and polymorphonuclear cells including myelomonocytic cells, lymphocytes, myoblasts, tissue macrophages, dendritic cells, Kupffer cells, lymphoid and reticuloendothelia cells of the lymph nodes and spleen, keratinocytes, endothelial cells, and bronchial epithelial cells.

As another example of an embodiment of the invention in which a viral vector is used to prepare the recombinant mutant or engineered viral DNA-packaging motor connector protein-derived polypeptide encoding expression construct, in one preferred embodiment, host cells transduced by a recombinant viral construct directing the expression of mutant or engineered polypeptides may produce viral particles containing expressed mutant or engineered polypeptides that are derived from portions of a host cell membrane incorporated by the viral particles during viral budding.

In another embodiment, the present invention relates to host cells containing the above described recombinant mutant or engineered viral DNA-packaging motor connector protein-derived polypeptide encoding expression constructs. Host cells are genetically engineered (transduced, transformed or transfected) with the vectors and/or expression constructs of these and related invention embodiments which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding mutant or engineered viral DNA-packaging motor connector protein-derived polypeptides. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of mutant or engineered viral DNA-packaging motor connector protein-derived polypeptide encoding expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

As used herein and in the appended claims, the singular forms "a," "and," and "the" include plural referents unless the context clearly dictates otherwise. Thus, for example, reference to "a polypeptide" or "the polypeptide" includes reference to one or more polypeptides (i.e., a plurality of polypeptides) and equivalents thereof known to those skilled in the art, and so forth, unless clearly indicated otherwise. Reference throughout this specification to "one embodiment," or "an embodiment," or "in another embodiment," or "in some embodiments" means that a particular referent feature, structure, or characteristic described in connection with the embodiment is included in at least one embodiment. Thus, the appearance of the phrases "in one embodiment," or "in an embodiment," or "in another embodiment" in various places throughout this specification are not necessarily all referring to the same embodiment. Furthermore, the particular features, structures, or characteristics may be combined in any suitable manner in one or more embodiments.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

The practice of the present invention will employ, unless indicated specifically to the contrary, conventional methods of chemistry, biochemistry, organic chemistry, molecular biology, microbiology, recombinant DNA techniques, genetics, immunology, cell biology, stem cell protocols, cell culture and transgenic biology that are within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Fire et al., *RNA Interference Technology: From Basic Science to Drug Development* (Cambridge University Press, Cambridge, 2005); Schepers, *RNA Interference in Practice* (Wiley-VCH, 2005); Engelke, *RNA Interference (RNAi): The Nuts & Bolts of siRNA Technology* (DNA Press, 2003); Gott, *RNA Interference, Editing, and Modification: Methods and Protocols* (Methods in Molecular Biology; Human Press, Totowa, N.J., 2004); Sohail, *Gene Silencing by RNA Interference: Technology and Application* (CRC, 2004); Clarke and Sanseau, *microRNA: Biology, Function & Expression* (Nuts & Bolts series; DNA Press, 2006); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In*

Cell And Molecular Biology (Mayer and Walker, eds., Academic Press, London, 1987); Handbook Of Experimental Immunology, Volumes I-IV (D. M. Weir and C C Blackwell, eds., 1986); Roitt, Essential Immunology, 6th Edition, (Blackwell Scientific Publications, Oxford, 1988); Embryonic Stem Cells: Methods and Protocols (Methods in Molecular Biology) (Kurstad Turksen, Ed., 2002); Embryonic Stem Cell Protocols: Volume I: Isolation and Characterization (Methods in Molecular Biology) (K. Turksen, Ed., 2006); Embryonic Stem Cell Protocols: Volume II: Differentiation Models (Methods in Molecular Biology) (K. Turksen, Ed., 2006); Human Embryonic Stem Cell Protocols (Methods in Molecular Biology) (K. Turksen Ed., 2006); Mesenchymal Stem Cells: Methods and Protocols (Methods in Molecular Biology) (D. J. Prockop, D. G. Phinney, and B. A. Bunnell Eds., 2008); Hematopoietic Stem Cell Protocols (Methods in Molecular Medicine) (C. A. Klug, and C. T. Jordan Eds., 2001); Hematopoietic Stem Cell Protocols (Methods in Molecular Biology) (K. D. Bunting Ed., 2008) Neural Stem Cells: Methods and Protocols (Methods in Molecular Biology) (L. P. Weiner Ed., 2008); Hogan et al., Methods of Manipulating the Mouse Embyro ($2^{nd}$ Edition, 1994); Nagy et al., Methods of Manipulating the Mouse Embryo ($3^{rd}$ Edition, 2002), and The zebrafish book. A guide for the laboratory use of zebrafish (Danio rerio), 4th Ed., (Univ. of Oregon Press, Eugene, Oreg., 2000).

EXAMPLES

Example 1

Assembly of Conductive Channel-Containing Membrane Using Isolated Viral DNA-Packaging Motor Connector Protein This example describes redesign of the dsDNA phage phi29 DNA-packaging motor connector protein to include distinct regions of hydrophilicity.

Materials.

The phospholipids 1,2-diphytanoyl-sn glycerol-3-phosphocholine (DPhPC) and 1,2-Dioleoyl-sn-Glycero-3-Phosphocholine (DOPC) were purchased from Avanti Polar Lipids (Alabaster, Ala.). N-(7-nitrobenz-2-oxa-1,3-diazol-4-yl)-1,2-dihexadecanoyl-sn-glycero-3-phosphoethanolamine, triethylammonium salt (NBD-PE) were purchased from Invitrogen. n-Decane and chloroform were purchased from Fisher and TEDIA, respectively.

Reengineering of Phi29 Connector.

The construction of the plasmid for the expression of the connector protein and the assembly of the dodecameric connector have been reported previously (Guo et al., J. Nanosci. Nanotechnol. 5, 856-863 (2005)). The subsequent terminal modifications of the connectors were also essentially as described except for the use of the specified flexibility and affinity/alignment domains as disclosed herein (Cai et al., Nanomedicine 4, 8-18 (2008); Sun et al., Nucleic Acids Res. 34(19), 5482-5490 (2006); Robinson et al., Nucleic Acids Res. 34, 2698-2709 (2006)). Briefly, the modification of one of the plasmids was, for example, achieved by a two-step PCR. First, the primer pair F1-R1 was used to amplify the GP10 gene The first PCR product was used as a template for a second step PCR with primer pair F1 and R2, which contained affinity Tags ($His_6$-tag and/or Strep-II tag, WSHPQFEK, SEQ ID NO:22) as well as the restriction sites for NdeI and XhoI, respectively. The second PCR product was digested with NdeI/XhoI and ligated into the NdeI/XhoI sites of the vector pET-21a(+) (Novagen) to generate the plasmid.

Expression and Purification of the Connector.

Plasmid pETgp10-C-strep-II or -C-$His_6$ was transformed into the E. coli strain HMS174 (DE3) for protein expression. A volume of 10 mL of the E. coli culture was incubated overnight at 37° C. in Luria-Bertani (LB) medium containing 100 μg/mL ampicillin and agitated at 250 rpm. A volume of 5 mL of the culture was inoculated into 500 mL medium and induced with 0.5 mM IPTG when the cell density reached 0.5-0.6 unit at $OD_{600}$. Cells were harvested 3 hours after IPTG induction by centrifugation at 5000×g for 20 min in a Beckman JS-7.5 rotor and then stored at −70° C. before use.

The Strep-II-tagged connector was purified by affinity chromatography with Strep-Tactin (IBA, St. Louis, Mo.). Cells were resuspended with Buffer W (15% glycerol, 0.5 M NaCl, 1 mM EDTA, 100 mM Tris-HCl, pH 8.0), and the cleared lysate was loaded onto a Strep-Tactin Sepharose Column and washed with Buffer W. The Strep-II-tagged connector was eluted by buffer E (15% glycerol, 0.5 M NaCl, 1 mM EDTA, 2.5 mM desthiobiotin, 100 mM Tris-HCl, pH 8.0). The His-tagged connector was purified with Nickel affinity chromatography (Novagen) essentially as described in Robinson et al. (2006).

In Vitro DNA Packaging Assay Using Phi29 Motor.

The purification of procapsids, GP16, and DNA-GP3 (Lee et al., J. Virol. 69, 5024-5032 (1995); Guo et al., Proc. Natl. Acad. Sci. USA 83, 3505-3509 (1986)), and the procedure for DNA packaging using the phi29 DNA packaging motor in vitro have been previously described (Guo et al., 1986; Lee et al., J. Virol. 69, 5018-5023 (1995). Briefly, a volume of 10 μL of 0.3 μg/μL of purified normal procapsids or reengineered procapsid C-strep were mixed with 100 ng of pRNA in TMS (100 mM Tris-HCl, pH 8.0, 10 mM $MgCl_2$, 100 mM NaCl) for 30 min at room temperature. The presence of $Mg^{2+}$ in TMS buffer promoted binding of pRNA to the procapsid. These pRNA-enriched procapsids were mixed with 3 μL reaction buffer (10 mM ATP/6 mM spermidine/3 mM β-mercaptoethanol in TMS), 100 ng of DNA-gp3, and 6 μL of 0.5 μg/μL DNA packaging enzyme gp16. The mixtures were then incubated for 30 min at room temperature. DNA packaging efficiency was verified by agarose gel electrophoresis using a DNase protection assay (Guo et al., Virology 185, 395-400 (1991)). The packaged DNA, which was protected by the procapsid, was shown on the gel.

The biological activity of the DNA-filled capsid was tested for its ability to be converted into infectious phi29 virion. After 30 min of DNA packaging, the neck, tail, and morphogenic proteins were added to complete the assembly of the infectious virions, which were then assayed by standard plaque formation (Guo et al., 1986; Lee et al., J. Virol. 69, 5018-5023 (1995)).

Fluorescence Labeling of the Connector.

The connector was labeled using a Fluoro Tag™ FITC conjugation kit (Sigma, St. Louis, Mo.). Buffer E was changed to a sodium carbonate-bicarbonate buffer using column chromatography. FITC solution was added drop wise into the connector solution and incubated for 2 hours with gentle stirring. Free FITC was removed by column chromatography, and FITC-labeled connector was eluted with PBS. FITC-connector was identified by SDS-PAGE. Labeling efficiency was determined from fluorescein/protein molar ratio and measured by UV-Vis spectrophotometry.

Preparation of Giant Lipid Vesicles Containing the Reengineered Connector.

To prepare the fluorescent giant lipid vesicles, 1 mL of 1 mg/mL DOPC or DPhPC and 1% (molar ratio) NBD-PE were mixed in a vial. Chloroform was evaporated by a gentle stream of nitrogen gas, and the lipid vial was further dried in a desiccator overnight. To rehydrate the lipid film, 2 mL of 200 mM-300 mM sucrose was used as exemplary osmotic agent to bud vesicles off the glass and into the solution. The vial was then covered with parafilm and stored overnight. An aliquot was taken from the middle of the solution and then transferred into a Petri dish. After settling, the vesicles were observed with epi-fluorescence microscopy (FIG. 5).

Incorporation of the viral DNA-packaging motor protein connector into giant vesicles was accomplished as described above, except the NBD-PE was omitted. A volume of 100 µL of FITC-labeled reengineered connectors was added to the above dehydrated lipid with a final lipid:connector mole ratio of 75:1 (or as low as 4000:1 to 16000:1 for BLM experiments) (FIG. 5).

Insertion of the Connector into Planar Bilayer Lipid Membrane.

Figure 5A:
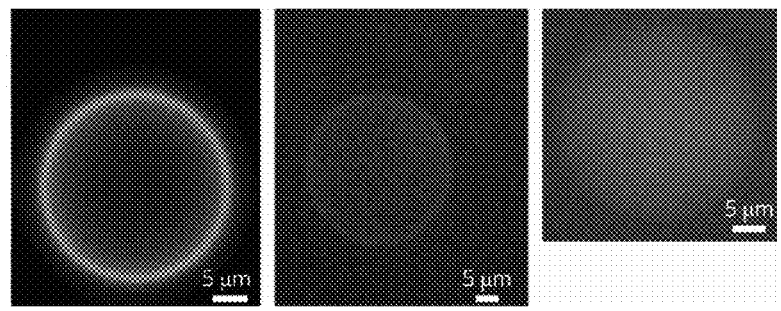
FIG. 5 shows images of giant liposome containing the modified phi29 gp10 connector. a-c, Epifluorescence images of liposome: lipid labeled with NBD-PE without connector (a); a proteoliposomes reconstituted by FITC labeled connectors (b); FITC-connector mixed non-specifically with liposomes (c). d-f, Membrane filtration isolated most of the free connectors. g, Separation of liposome/FITC-connector complexes by sucrose gradient sedimentation. Free connectors appeared in the top fractions while proteoliposomes remained in the lower fractions. Fractions #1-12 are not shown. h, Fluidity of fluorescent (red) lipid bilayer demonstrated by FRAP (Fluorescence Recovery After Photobleaching) showing that the fluorescence intensity of photobleached area (black) was gradually increased over time due to lipid diffusion. i, Schematic showing the insertion of the connector into a planar lipid bilayer.
Figure 5B:
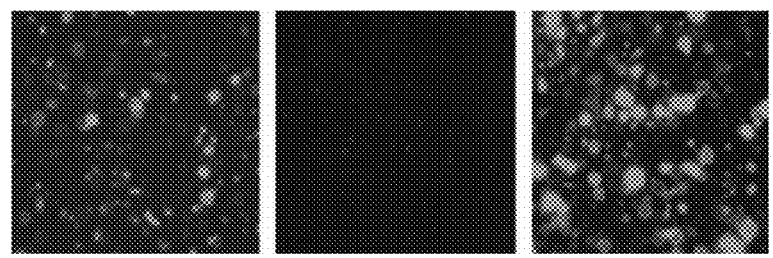
Figure 5C:
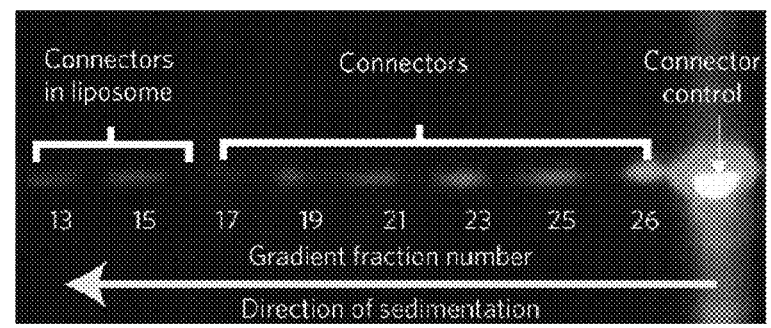
Figure 5D:
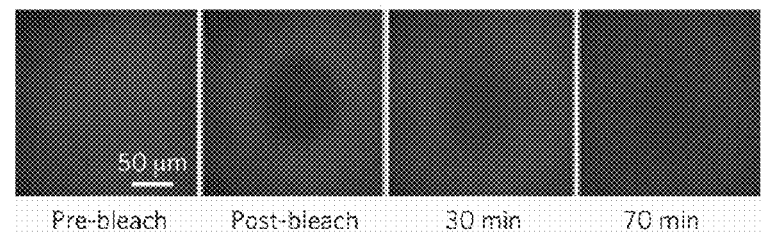

A two-step approach was used to incorporate the connector into the planar bilayer lipid membrane (BLM). The first step was the preparation of unilamellar lipid vesicles containing the reengineered connector as described above. The next step was to fuse the extruded liposome into a planar BLM (FIG. 5). The fluidity of the lipid bilayer was demonstrated by FRAP (Fluorescence Recovery After Photobleaching) (FIG. 5D). An excitation light was focused continuously on the bilayer to bleach the dye. The photobleached area appeared dark. But after the light was switched off, the appearance of fluorescence gradually recovered due to the return by diffusion of the fluorescent lipid into the photobleached area.

A standard BLM chamber (BCH-1A from Eastern Scientific LLC, Rockville, Md.) was utilized to form horizontal BLMs. A thin Teflon film with an aperture of 70-120 µm (TP-01 from Eastern Sci. LLC) or 180-250 µm (TP-02 from Eastern Sci. LLC) in diameter was used as a partition to separate the chamber into cis- (working volume 250 µL) and trans- (working volume 2.5 mL) compartments. After the aperture was pre-painted twice with 0.5 µL 3% (w/v) DPhPC n-decane solution to ensure the complete coating of the entire edge of the aperture, these compartments were filled with conducting buffers (5 mM Tris/pH 7.9, TMS, or 5 mM HEPES/pH 7.9, with varying concentration of NaCl or KCl).

Figure 5E:
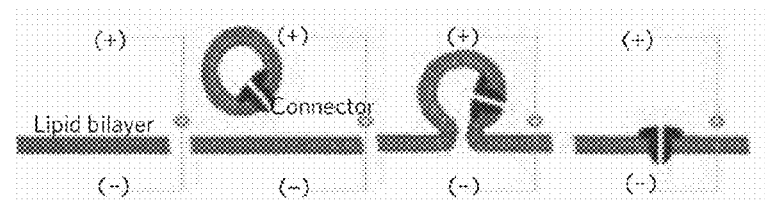

Formation of the bilayer membrane on the partition was a precursor step for viral DNA-packaging motor protein connector insertion into the bilayer (FIG. 5E). The occurrence of successful viral DNA-packaging motor protein connector insertions was about 47-83% in the studies described here (approximately 280 separate BLM experiments).

For single conductance measurements, the giant liposome/connector complex prepared earlier was extruded using a polycarbonate membrane with pore size of 200 nm or 400 nm to generate small unilamellar liposomes. This liposome stock solution was further diluted by 10-20 fold for the BLM experiments before use. For insertion of viral DNA-packaging motor protein connectors, 0.5-2 µL of the diluted liposome solution was loaded into the cis-chamber.

Conductance was measured in two ways: the first was derived at specific but constant holding potentials, and the second from the slope of the current trace induced by a scanning potential starting at −100 mV and ramping to 100 mV after incorporation of phi29 GP10 viral DNA-packaging motor protein connector into the lipid membrane (FIG. 6).

Q-PCR Analysis.

Figure 11A:
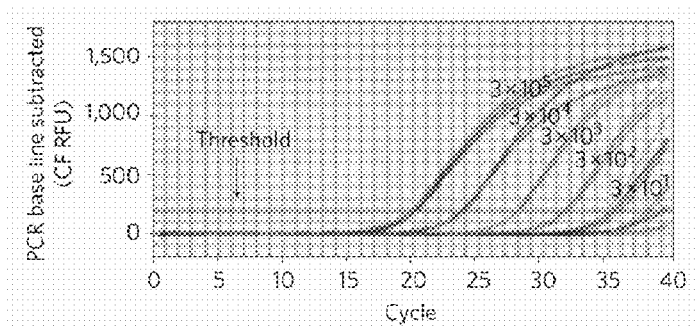
FIG. 11 shows Quantitative PCR (Q-PCR) analysis of DNA translocation events. a, Q-PCR amplification curves of the dilution series run in triplicate. b, A standard curve with the $C_T$ plotted against the log of the starting quantity of template for each dilution. c, Quantitative analysis of the total number of DNA passing through one of the connectors in the lipid membrane from the trans-chamber to the cis-chamber (top). Negative controls (bottom) were carried out under the same condition but without connectors. The error bars represent standard deviations of the mean from 9 independent experiments and 4 negative control experiments.
Figure 11B:
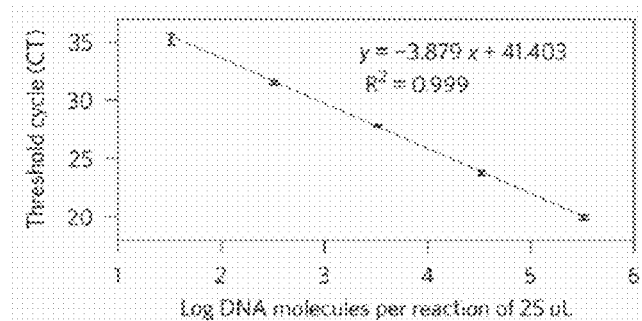
Figure 11C:
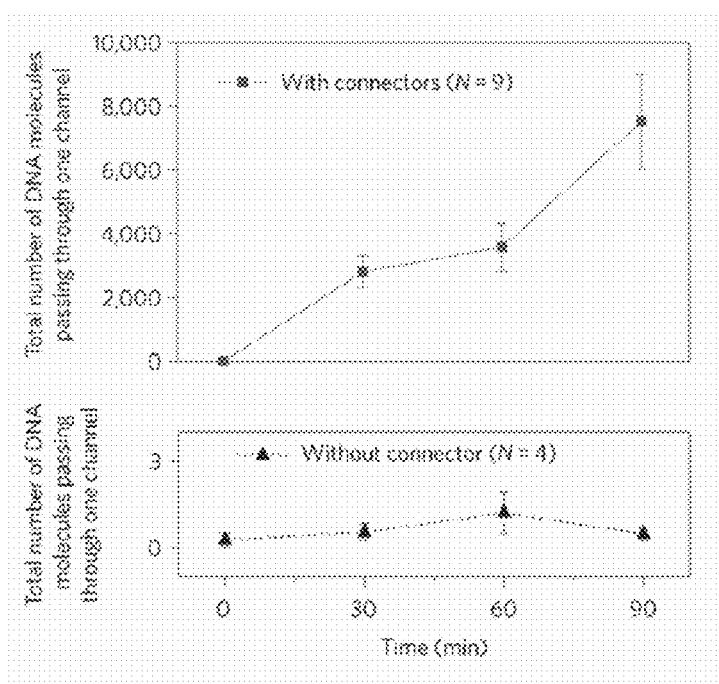

For Q-PCR analysis, the connector/liposome complexes were added to the cis-side (working volume 500 µL). 141-bp DNA was added to the trans-side with a final concentration of 25 nM. As a negative control, the DNA was added without the addition of connector/liposome complexes. A potential of −95 mV was applied and samples were collected from the cis-side at 30 min intervals for Q-PCR analysis. DNA concentration was determined by a DU530 UV/Vis spectrometer (Beckman Coulter, Fullerton, Calif.). Absolute quantification was used to determine the copy number of DNA in samples collected. Standard curves were constructed using the 141-bp DNA with 10 fold dilution of known concentration (FIG. 11). Each dilution was assayed in triplicate. iQ™ SYBR Green Supermix (Bio-Rad, Hercules, Calif.) was used for the Q-PCR reaction. Q-PCR was carried out in the iCycler iQ™ multicolor real-time PCR detection system (Bio-Rad). The sequences for forward and reverse oligonucleotide primers corresponding to the DNA template were 5'-TAA TAC GAC TCA CTA TTA GAA CGG CAT CAA GGT GAA CTC AAG ATT TTG TAT GTT GGG GAT TA-3' [SEQ ID NO:48] and 5'-AAG AAC GGC ATC AAG GTG AAC TTC AAG ATA ATT GAC AGC AGG CAA TCA AC-3' [SEQ ID NO:49], respectively (oligos were purchased from Integrated DNA Technologies, Inc. ("IDT"), Coralville, Iowa).

Example 2

Incorporation of Isolated Viral DNA-Packaging Motor Connector Protein into Liposomes to Form Conductive Channel-Containing Membrane This example describes insertion into liposomes and a lipid bilayer of the modified viral DNA-packaging motor connector protein that was designed and prepared as described above, including in Example 1, and characterization of the resulting conductive channel. The presence of the channel across the lipid bilayer that was formed by the connector protein was confirmed by single channel conductance measurements and translocation of dsDNA.

Separation and Detection of Liposome/Connector Complex by Sucrose Gradient Sedimentation.

A 5-20% linear sucrose gradient sedimentation in TMS (50 mM Tris, pH 8.0, 100 mM NaCl, 10 mM $MgCl_2$) (Guo et al., 1986) was performed to separate the liposome/connector complexes from the free connector. A 0.1 mL sample was loaded at the top of the 5-mL centrifugation tube. After spinning in a Beckman L-80 ultracentrifuge at 27,000 rpm for 30 min at 20° C. in a SW55 rotor, fractions were collected from the bottom of the tube and analyzed by 10% SDS-PAGE (FIG. 2).

Filtration.

The proteoliposomes were filtered with a 0.45 µm cellulose acetate membrane (Life Science Products, Inc.) to separate the free connector from the liposome/connector complex. A volume of 500 µL of connector-incorporating DOPC liposome vesicles in 200 mM sucrose solution was added to the filtration tube and filled with the same solution. Less than 200 µL of liquid was retained after spinning at 3000×g for 15 min. This microfiltration process was repeated five times. The liposomes/connector complexes retained on the top of the filter were imaged by fluorescence microscopy (FIG. 5).

Preparation of dsDNA for Translocation Experiments.

A 35-bp dsDNA was prepared by annealing two single stranded DNA, 5'-TTA TAG GGA TAG TTG TAA GCT AAA GAA TAC GTT AC-3' (Integrated DNA Technologies, Inc. ("IDT"), Coralville, Iowa) and 5'-GTA ACG TAT TCT TTA GCT TAC AAC TAT CCC TAT AA-3' (IDT). The annealing was performed at 65° C. for 3 min and the sample was incubated at room temperature for 2 hrs. A 16% PAGE gel was used to purify the dsDNA. After releasing the DNA from the gel, it was concentrated by ethanol precipitation.

A linear 5.5 kilo-base plasmid DNA was prepared from an in-house constructed circular plasmid, Cx43, with a bluntend cut by an endonuclease, EcoRV. After purification with a QIAGEN MiniElute Reaction Cleaning-up kit (QIAGEN), the DNA was added to trans-side directly for DNA translocation experiments.

Electrophysiological Measurements.

A pair of Ag/AgCl electrodes connected directly to the head-stage of a current amplifier were used to measure the current traces across the bilayer lipid membrane, and the trace was recorded using an Axopatch 200B patch clamp amplifier coupled with the Axon DigiData 1322A or Axon DigiData 1440 analog-digital converter (Axon Instruments, Inc., Union City, Calif.). All the voltages reported are those of the trans-compartment. Data were low-pass filtered at a frequency of 1 kHz and acquired at sampling frequency of 2 kHz, if not specified. The PClamp 9.1 software (Axon Instruments) was used to collect the data, and the software Clampfit was used for data analysis.

Double-Stranded DNA Translocation Experiments.

In the DNA translocation experiments, DNA was added to the trans-side, if not specifically stated. C-His$_6$ tagged connector (viral DNA-packaging motor protein connector having C-terminal hexahistidine modification) was used to evaluate translocation events. TMS/1M NaCl buffer was used as DNA translocation buffer. Two methods were used to add DNA to the chamber for the translocation experiments. Method 1: DNA was added under a voltage of 0 mV after connector insertion. When the voltage was switched back, the DNA moved towards connector channels by free diffusion of DNA and applied voltage; Method 2: DNA was premixed with buffer completely in the chamber before connector insertion. The DNA movement relied mainly on applied voltage. All experiments were performed using Method 1 unless otherwise specified.

Modifying the Phi29 DNA-Packaging Motor Connector Protein.

Figure 4:
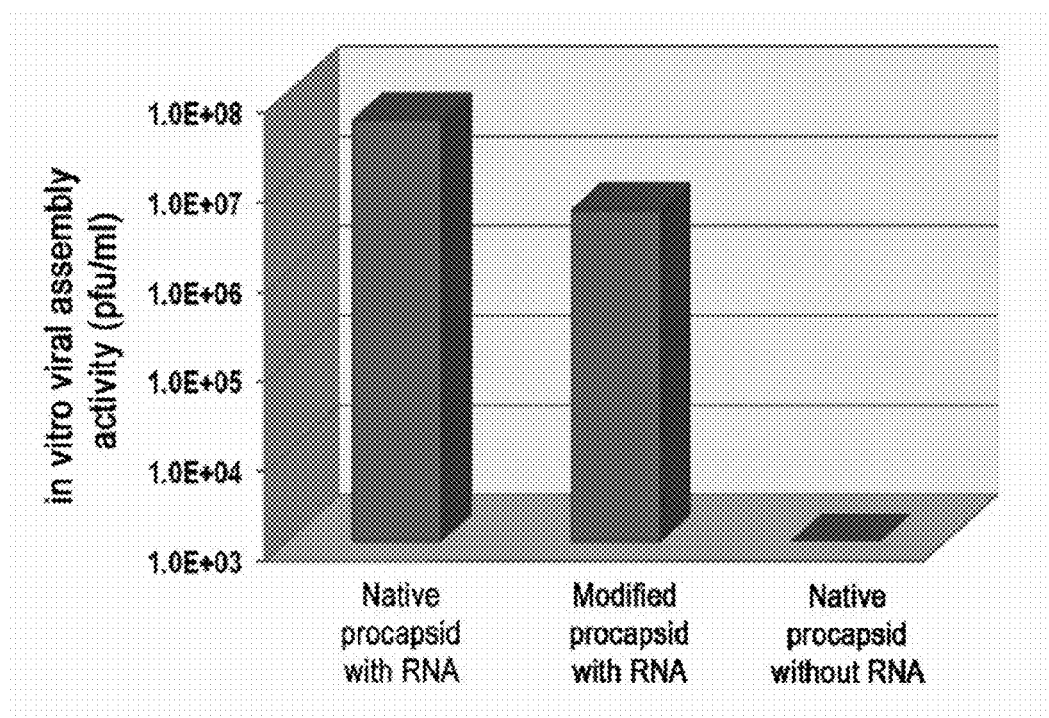
FIG. 4 shows phi29 virion assembly activity of procapsid containing the reengineered connector having C-terminal 6-Gly flexibility domain and Strep-II tag affinity/alignment domain. In vitro viral assembly activity of the reengineered procapsid was compared to that of native procapsid in the presence of pRNA.

In general, membrane pores and ion channels contain a hydrophobic domain which anchors the protein in the membrane. Analysis of the surface charge of the phi29 connector revealed that its central surface region exhibited slight hydrophobicity compared with the two flanking layers at the wide and narrow ends, respectively (FIG. 1)(Simpson et al., 2001 *Acta Crys. D*57:1260-69; Guasch et al., 2002 *J Mol Biol* 315:663-676). To facilitate connector purification, an affinity/alignment domain comprising a C-terminal His (His$_6$) or Strep-II (WSHPQFEK) tag was inserted just downstream of a flexibility domain comprising a six glycine linker for improved affinity tag flexibility. Six-glycine linkers were included to provide end-flexibility (FIG. 2). After purification to homogeneity, it was found that the modified DNA-packaging motor protein connector polypeptide, GP10, self-assembled into the motor protein connector dodecameric structure with similar morphology to the 12-fold symmetric wild type connector (FIG. 1F), as observed by transmission electron microscopy, TEM (FIG. 1D,E). The existence of a native and authentic motor configuration was verified through its competency to package the double-stranded DNA after incorporation into the procapsid (FIG. 3) and to assemble the resulting DNA-filled capsid into the infectious phi29 virion (FIG. 4).

Reconstituting the Connector into Liposomes.

A procedure for reconstituting the connector into liposomes was developed by co-incubation of the connector with the lipid in the presence of sucrose as an exemplary osmotic agent. Such incubation provided an opportunity for the hydrophobic layer of the connector to interact with the hydrophobic domain of the lipid molecules. The dehydration-rehydration method (Lasic, D. D., *Liposomes in Gene Delivery*. CRC Press LLC., (1997), Boca Raton, Fla.) led to the production of giant liposomes up to 50 μm in diameter (FIG. 5). The insertion of the connector protein into the lipid membrane was confirmed by fluorescence microscopy, filtration assay, and sedimentation analysis (FIG. 5). The presence of the connector in the membrane was visible with fluorescence microscopy, showing a clear fluorescent ring around the liposome (FIG. 5). The fluorescent ring was very similar in appearance to the liposome generated with fluorescent lipids NBD-PE (FIG. 5A). No fluorescent ring was observed when the fluorescently-tagged connector was mixed non-specifically with the non-connector inserted liposome (FIG. 5). The free connectors were removed by filtration using a membrane with a pore size of 0.45 μm or by 5-20% sucrose gradient ultracentrifugation (FIG. 5).

Incorporating the Connector into Planar Lipid Membranes.

Figure 6A:
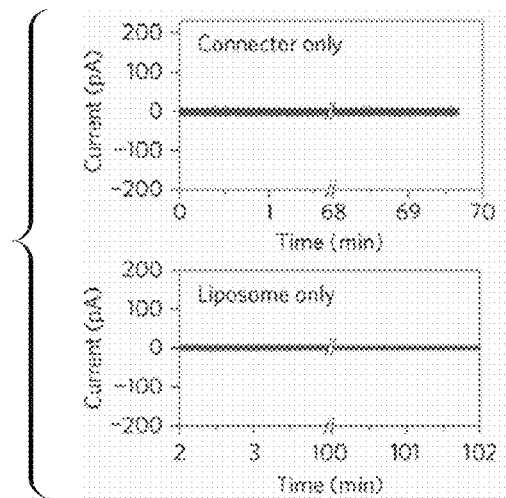
FIG. 6 shows conductance assay to confirm the insertion of the modified phi29 gp10 connector into bilayer lipid membranes (BLM). a, BLM with connector only (top) or liposomes only (bottom). b, Addition of connector-containing proteoliposomes resulted in multiple insertions. (Reproduced in over 200 experiments.) Inserts: Insertion of one (top) and two connectors simultaneously (bottom). c, One connector insertion at positive voltage (top) and at negative voltage (bottom). d, Distribution of current jump after multiple connector insertions. e, Current-voltage relationship of single connector channels. Error bars represent 3-5 insertions under each applied voltage from a total of 38 inserted connectors in 4 individual experiments. f-g, Slopes of current traces with 1, 2 or 3 connectors (f) and 1 connector in the presence of dsDNA (cis-chamber) (g). d-f, 5 mM Tris buffer, pH 7.9 with 0.5M NaCl. g, TMS with 1M NaCl.
Figure 6B:
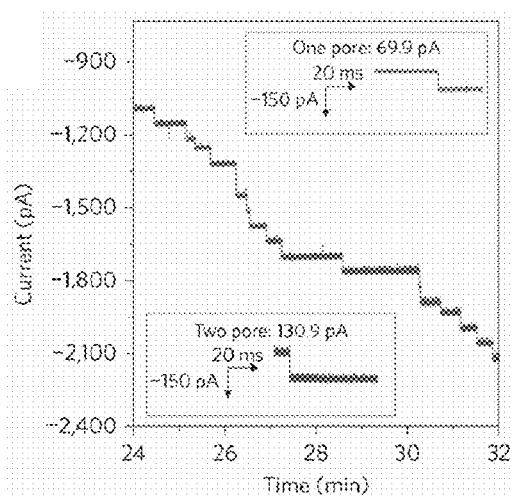
Figure 6C:
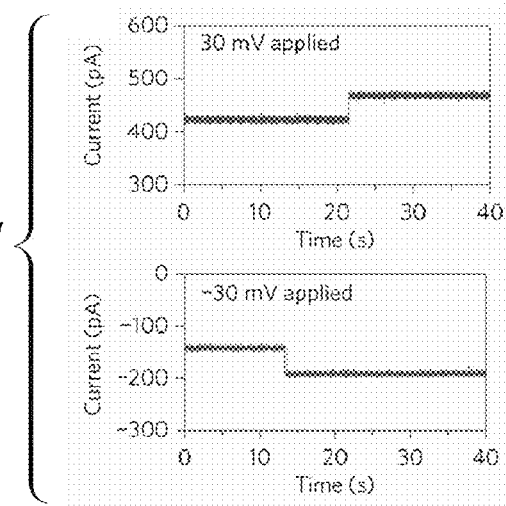

Since none of the above experiments could distinguish between loose attachment of the connector to the bilayer surface and tight incorporation of it into the bilayer membrane to form a channel via retention of its aperture when integrated into the bilayer, a single channel conductance assay was performed. Results showed that direct incubation of the connector protein with liposomes or with a planar lipid bilayer did not lead to channel formation in the bilayer membrane (FIG. 6A). Connector insertion into the bilayer only occurred when the connector protein-reconstituted proteoliposomes were fused into the bilayer (FIG. 6B-C) The channel insertion was observed through a discrete step-wise increase in conductance as shown in a continuous current trace (FIG. 6), under either positive or negative transmembrane voltage.

Figures 6D, 6E, 6F, 6G:
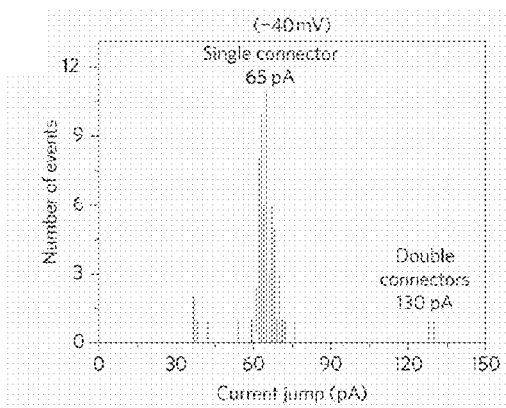
Figure 7:
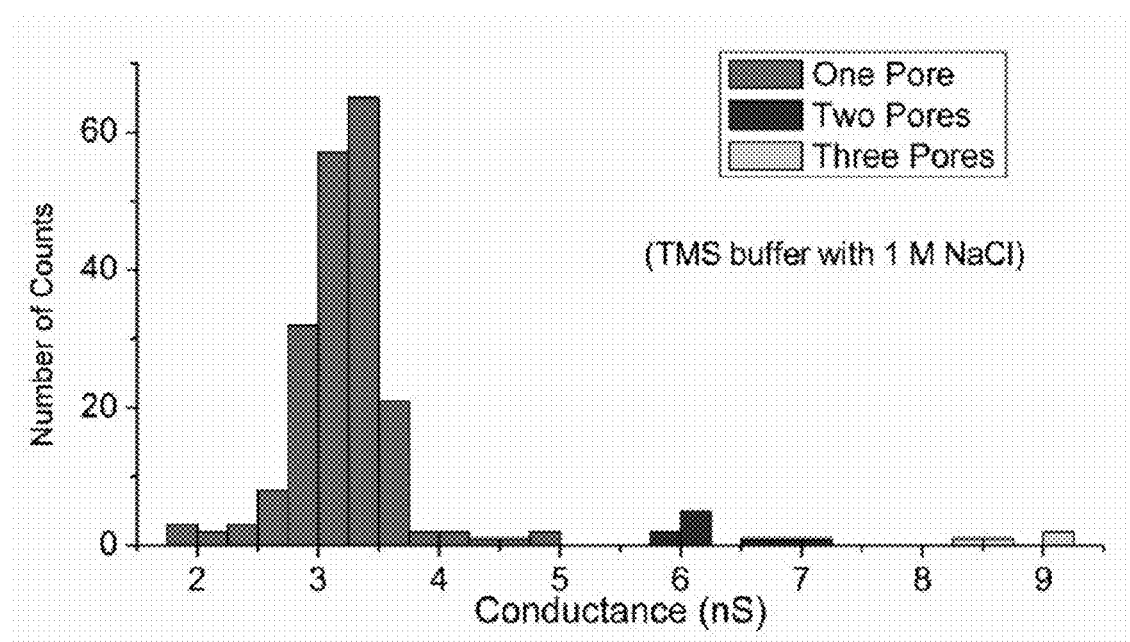
FIG. 7 shows a histogram of sizes of the conductance steps caused by insertions of modified phi29 DNA-packaging motor protein connector having C-terminal 6-Gly flexibility domain and Strep-II tag affinity/alignment domain. The data were obtained from a total of 213 insertions in 40 individual experiments.

Typically, the insertion of one connector into the bilayer resulted in an increase in the current of approximately 65 pA (equivalent to 1.6 nS) at a potential of −40 mV in the presence of a solution of 5 mM Tris (pH 7.9)/0.5 M NaCl. Occasionally a 130.9 pA jump, attributed to membrane insertion of two connectors, was also observed (FIG. 6D). Similar results were obtained when the channel conductance was measured in TMS/1 M NaCl (FIG. 7). In this case, the occurrence of simultaneous insertion of two connectors and three connectors was 4.7% and 1.9%, respectively.

For conductance measurements, a plot of the I-V curve was obtained under different voltages (FIG. 6E). The average conductance per single pore was 1.57±0.16 nS/pore (a total of 38 inserted connectors) in a 5 mM Tris/0.5 M NaCl (FIG. 6E) and 3.21±0.51 nS/pore (a total of 213 inserted connectors) in a TMS/1 M NaCl buffer (FIG. 7). As a comparison, the conductance measurements were also performed for connector channels under a ramp voltage (FIG. 6F,G]). The slopes from the fitted curves representing the conductance of formed channels in the 5 mM Tris/0.5 M NaCl were 1.59 nS/single pore, 3.40 nS/two pores, and 4.98 nS/three pores, respectively. When NaCl concentration increased to 1 M (TMS buffer with 1 M NaCl), the slope of the curve was 3.12 nS/single pore. A buffer of 5 mM HEPES/1 M KCl was also used for conductance measurements (Table 1).

TABLE 1

Comparison of Single Channel Conductance from the GP-10 Connector (phi29 motor protein connector) and α-Hemolysin

| Proteins | Pore diameter (nm) | Cross section area (nm$^2$) | Conductance (nS/pore)$^a$ | |
|---|---|---|---|---|
| | | | at 0.5M NaCl | at 1M KCl |
| Connector | 3.6 | 10.2 | 1.57 ± 0.16 | 4.84 ± 0.15 |
| α-HL | 1.5$^{30}$ | 1.8 | 0.31 ± 0.05$^b$ | 0.94 ± 0.01$^c$ |

TABLE 1-continued

Comparison of Single Channel Conductance from the GP-10
Connector (phi29 motor protein connector) and α-Hemolysin

| Proteins | Pore diameter (nm) | Cross section area (nm$^2$) | Conductance (nS/pore)$^a$ | |
|---|---|---|---|---|
| | | | at 0.5M NaCl | at 1M KCl |
| Ratio (Connector/α-HL) | 2.4 | 5.7 | 5.1 | 5.1 |

$^a$ The data for connector conductance at 0.5M NaCl, and 1M KCl were obtained from a total of 38 and 36 insertions, respectively. The data for α-HL conductance at both 0.5M NaCl and 1M KCl were from a total of 4 insertions, respectively.
$^b$ Conductance of α-HL at 1M NaCl has been reported to be 0.68 nS/pore (Braha et al., 1997 Chem. Biol. 4: 497).
$^c$ Conductance of α-HL at 1M KCl has been reported to be 0.80 (Wong et al., 2006 Nanotechnol. 17: 3710) or 1.0 (Vercoutere et al., 2001 Nat. Biotechnol. 19: 248) nS/pore.

The channel conductance of the connector was compared with that of *S. aureus* alpha-hemolysin (α-HL) using solutions of different ionic strength (Table 1). It has been reported that the diameter of the narrow end of the connector channel is 3.6 nm, while the channel formed by α-HL has a diameter of only 1.5 nm (Song et al., 1996 *Science* 274:1859). Therefore, the ratio of the cross-sectional area of the channels between the connector and α-HL was 5.7. The ratio of measured conductance of the connector to α-HL was 5.1 (Table 1).

Since the conductance of a channel is proportional to its cross-sectional area, it can be concluded that the cross-sectional area of the aperture formed by the viral DNA-packaging motor protein connector in the buffer solutions was approximately 5.1 fold greater than that of α-HL, which compared well with the ratio of cross-sectional areas from the crystal data of both proteins. Moreover, compared with other transmembrane proteins or ion channel proteins with larger channels, e.g., Streptolysin (Gilbert et al., 1999 *Cell* 97:647), Kir (Lopatin et al., 1996 *Biophys J* 71:682), VDAC (Szabo et al., 1998 *FASEB J* 12:495) and bacterial porins (Iqbal et al., 2007 *Nat. Nanotechnol.* 2:243), the connector channel had additional advantages. For example, the viral DNA-packaging motor protein connector channels were stable and, unlike the previously described transmembrane channels, did not exhibit voltage gating under the reported conditions. The channel conductance was uniform, demonstrating a linear response to applied voltages between −100 mV and 100 mV (FIG. 6F,G).

Translocation of Double-Stranded DNA.

Both linear and circular plasmid Cx43 DNA (5.5 kb) were used to examine the translocation of dsDNA through the aperture formed by the viral DNA-packaging motor protein connector channel. In the case of the linear DNA plasmid, DNA translocation induced numerous current blockades which led to the current jump of single connector insertion transiently reduced by 25-45% (FIG. 8). Similar results were also found in translocation experiments of a 35-bp dsDNA (FIG. 9). However, when the linear Cx43 was added to the cis-chamber, no such blockades were observed until the voltage was switched to positive potential (FIG. 6G). The short-lived blockades could be attributed to the occurrence of DNA translocations. In contrast, in the absence of DNA, the current trace was quiescent (FIGS. 8, 9). Occasionally, unspecific blockades were observed with a minimum detectable time. These unspecific blockades rarely occurred compared to DNA translocation events. They were usually characterized with detectable time very close to the limit of sampling frequency. (FIGS. 8B, 6G). When circular plasmid dsDNA Cx43 was used, no translocation of the circular plasmid was observed (FIG. 8B, upper left). Interestingly, when the same amount of circular plasmid digested by DNase I was added to the chamber, a burst of transient blockades occurred (FIG. 8*b* lower left). The same results were also observed when the linear Cx43 digested by DNase I was used (FIG. 8B lower right). All the above results confirmed that only the linear dsDNA passed through the connector channels.

Figure 8C:
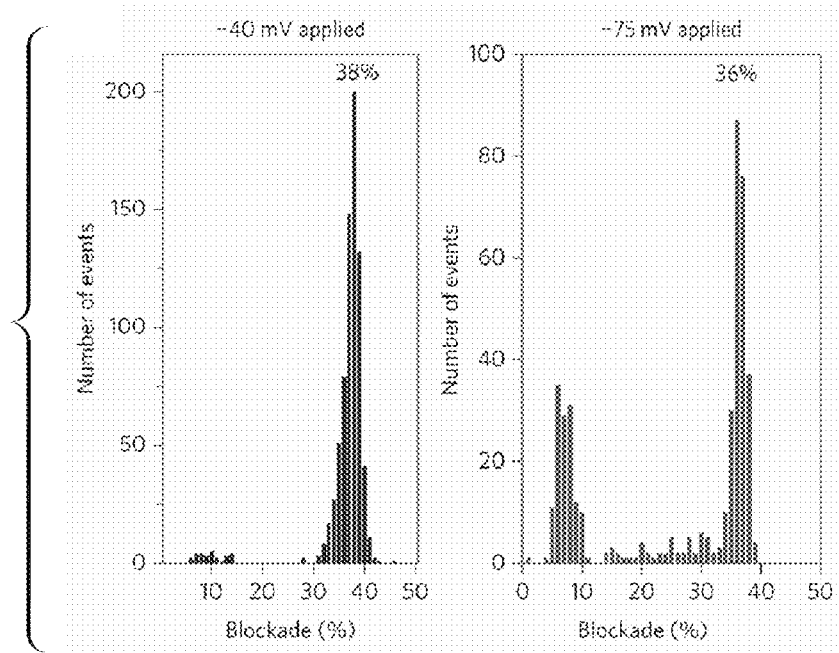
FIG. 8 shows translocation of dsDNA through modified phi29 gp10 connector channels in bilayer membrane (BLM). a, A typical current trace when BLM contains a connector but no DNA (Control). b, Representative blockades caused by 45 pM double-stranded circular and linear plasmid DNA without and with DNase digestion in BLM containing 3 connectors. c, d, Histogram showing the percentage of current blockade (c) and dwell time (d) caused by linear plasmid dsDNA under −40 mV and −75 mV. DNA translocation experiment was repeated 45 times.
Figure 8D:
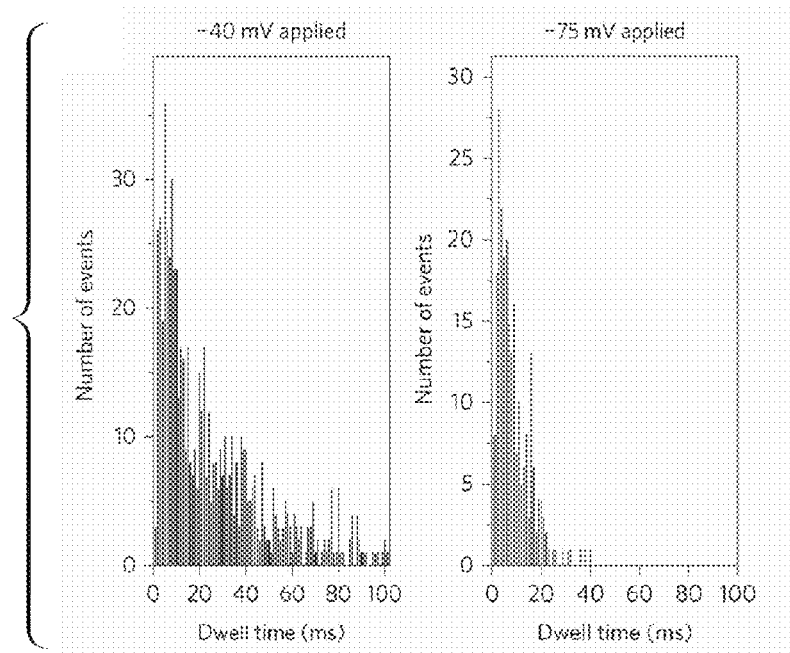
Figure 9A:
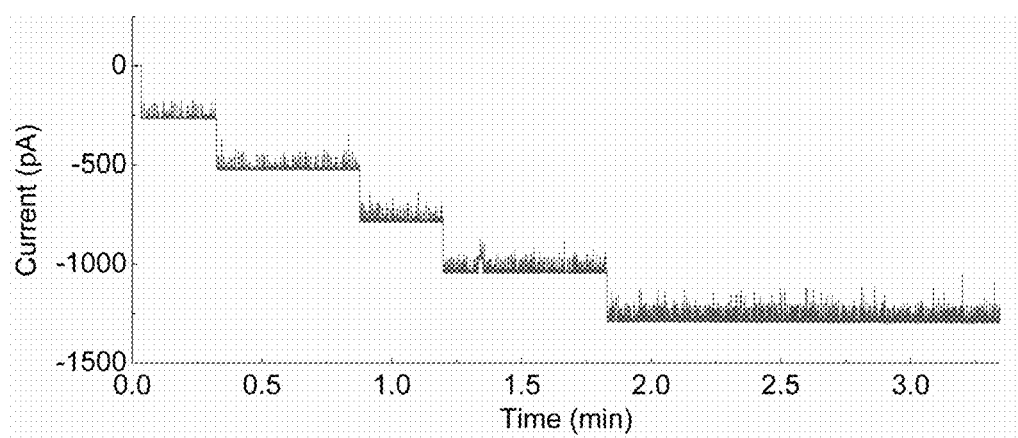
FIG. 9 shows a continuous current trace showing modified phi29 DNA-packaging motor protein connector insertions and DNA translocation under −75 mV. a, The case in which 4 µM of a 35-bp DNA was pre-mixed in buffer (Method 2 under "Double-stranded DNA translocation experiments" in Example 2); b-f, The case in which 4 µM of a 35-bp DNA was added after the insertion of connector into the bilayer lipid membrane (Method 1 under "Double-stranded DNA translocation experiments" in Example 2). Current traces continuously recording addition of modified connector and DNA. (Each trace was recorded in 50 second increments).
Figure 9B:
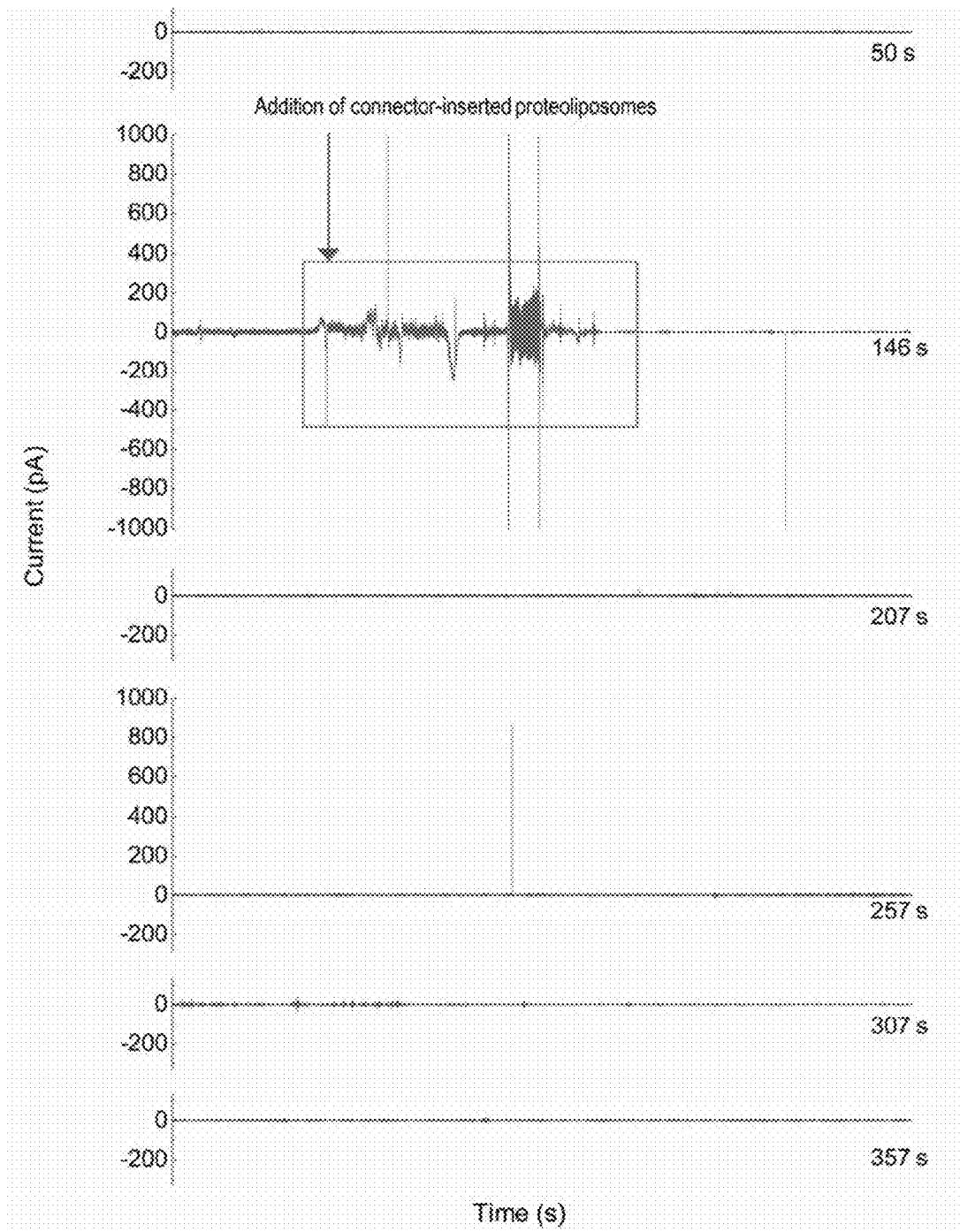
Figure 9C:
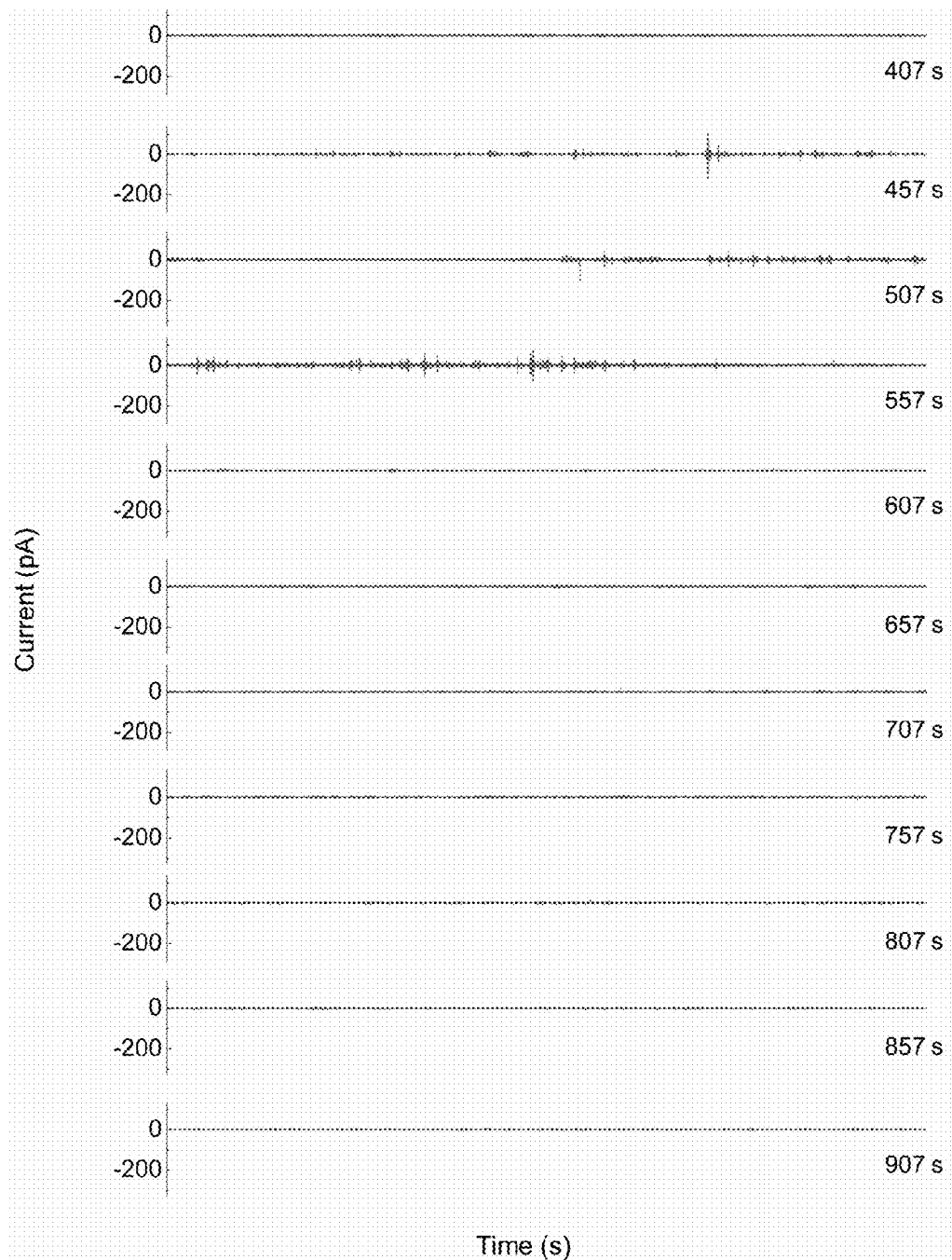
Figure 9D:
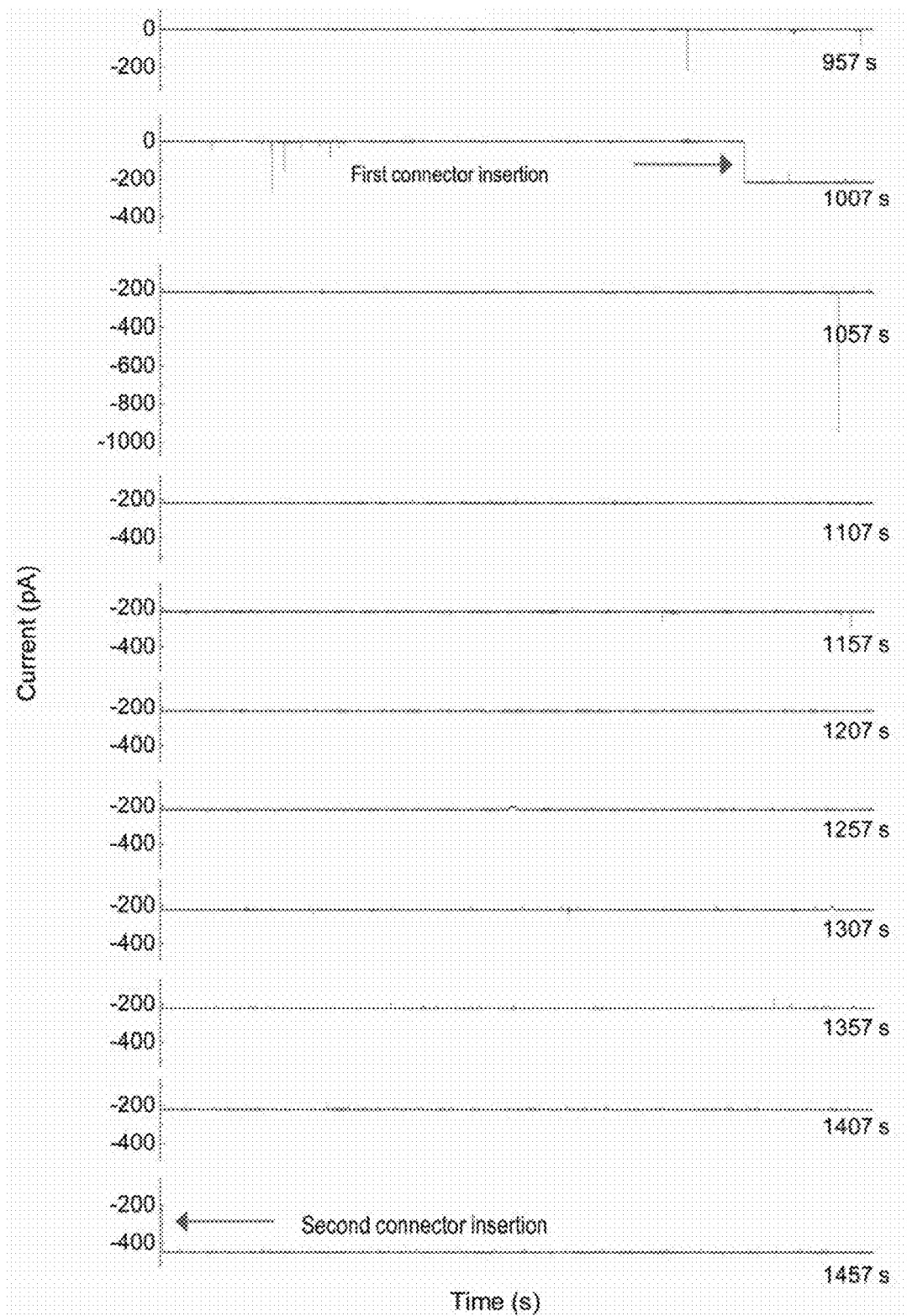
Figure 9E:
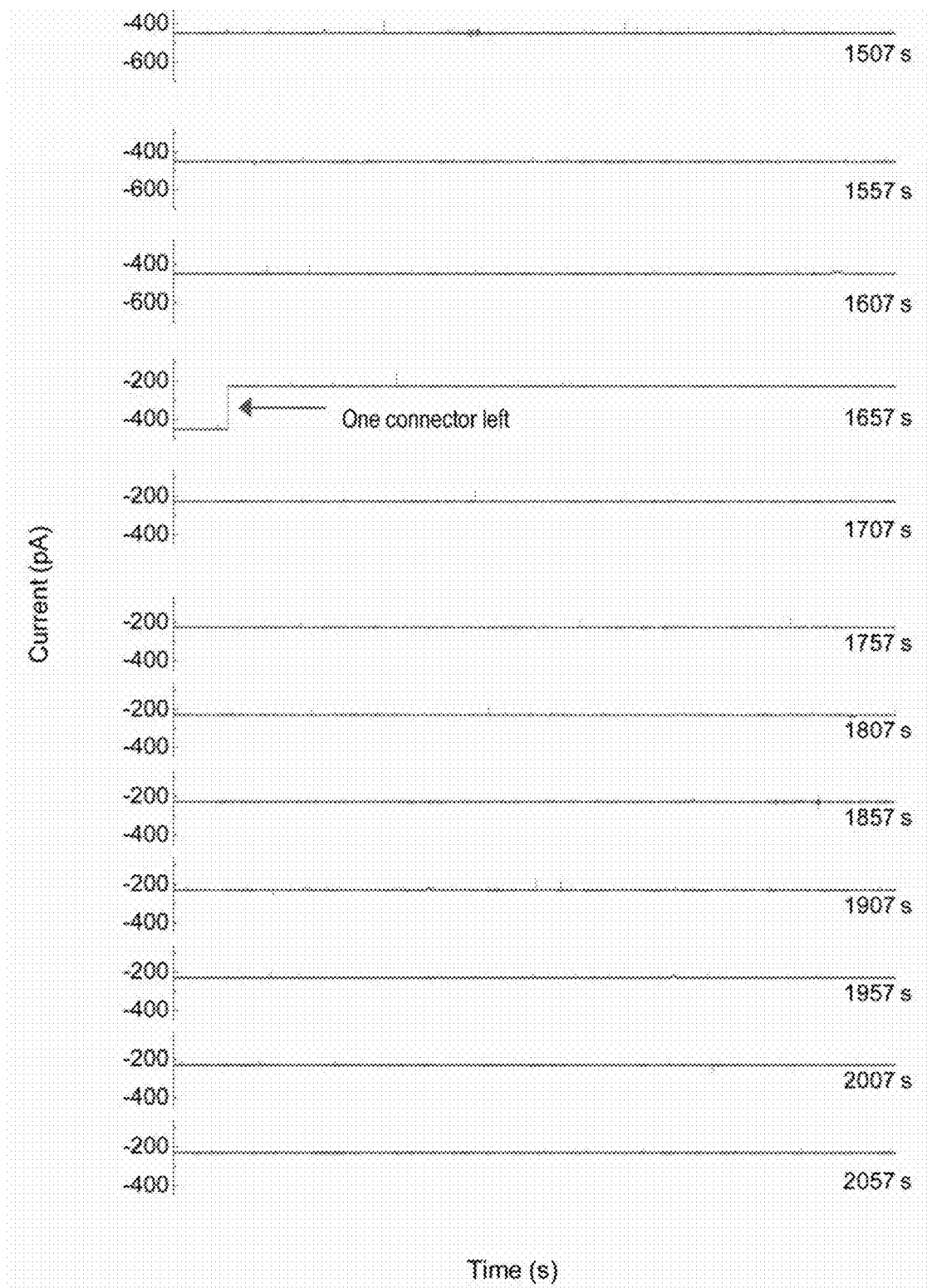
Figure 9F:
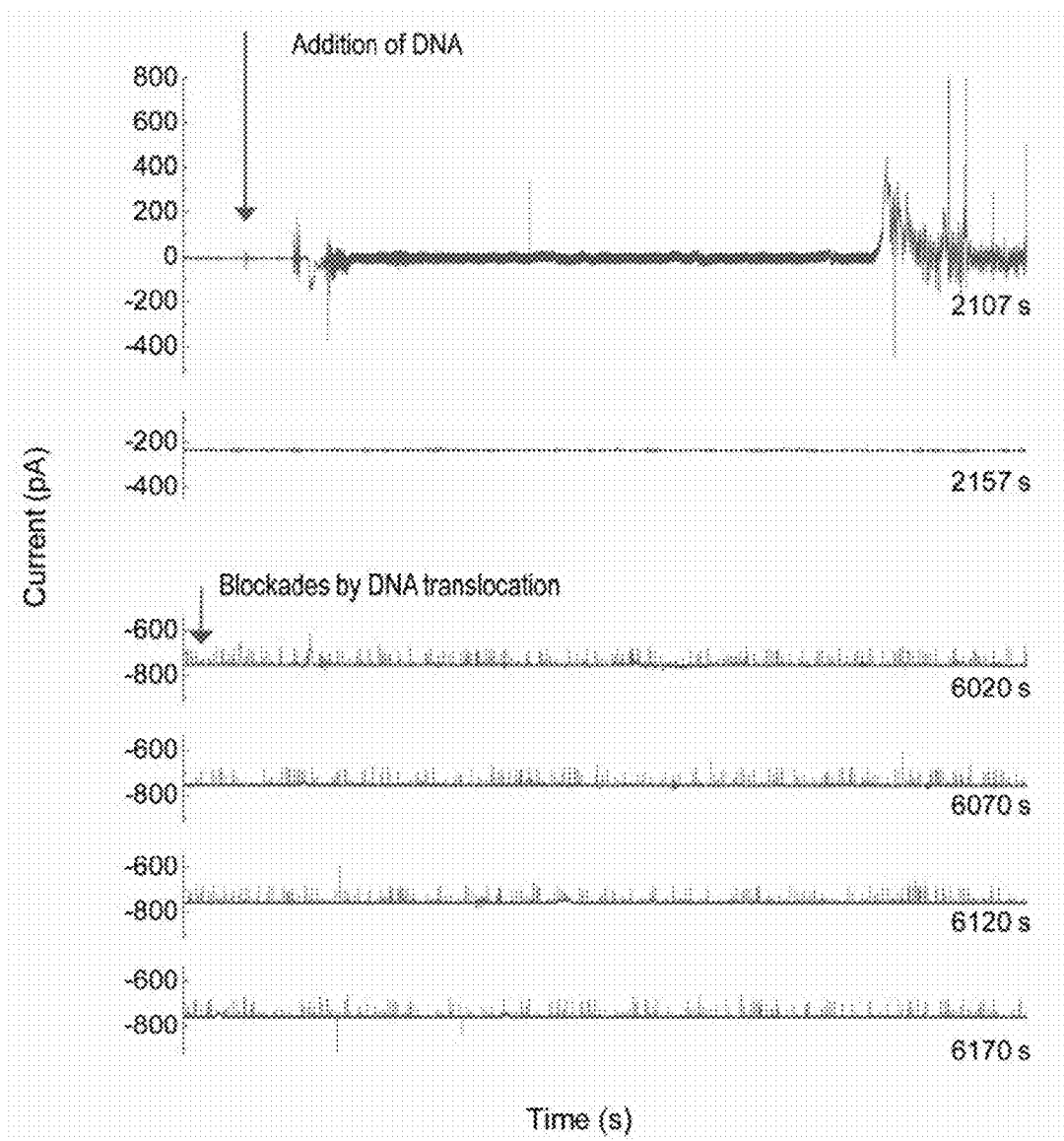

Occasionally, blockade events were observed in the range of 5-15% (FIG. 8C right) with a dwell time from several to hundreds of milliseconds. These events were attributed to non-specific blockades other than DNA translocation because they were found to occur in the absence of DNA (FIG. 9B). The non-specific blockade events could be due to interactions of viral DNA-packaging motor protein connector apertures (conductive channels) with lipid or lipid micelles because their occurrence was observed to increased after the addition of more liposomes to the chamber. The occurrence of the non-specific blockades could be minimized when the diluted connector reconstituted liposomes were used and/or when lower transmembrane voltage was applied (FIG. 8C left). Interestingly, simultaneous blockade events were occasionally detected (FIG. 8B, upper right, and FIG. 9). These events were recorded under multiple pore conditions. A continuous current trace recording events before and after addition of DNA was also shown (FIG. 9B). On one occasion, a burst of DNA blockades was observed after the insertion of a third viral DNA-packaging motor protein connector. In comparison, when DNA was premixed with buffer before connector insertion, the DNA blockades were observed immediately after the first insertion occurred (FIG. 9A). This result indicated a lack of a stirring facility in the DNA chamber leading to a delay in DNA translocation.

The blockade rates were affected by two factors: DNA concentration and transmembrane voltage. In the presence of 45 pM DNA under 3 viral DNA-packaging motor protein connector insertions, the blockade rate was approximately 0.8-1 blockades/s (FIG. 8B upper right). Under the same number of viral DNA-packaging motor protein connector insertions, when 4 μM of DNA was placed in the chamber, the blockade rate was approximately 5-5.8 blockades/s (FIG. 9A-B). For the linear Cx43 DNA, the blockade rate increased as the ramping voltage was applied (FIG. 6G).

To calculate the dwell time ($\tau_p$) for DNA translocation events, blockade episodes greater than 32% were grouped, since this percentage of blockade seemed consistent with the ratio of cross sectional area between dsDNA and the pore. A histogram of these events can be seen in FIG. 8D. It should also be noted that 6 (under −75 mV) and 20 (under −40 mV) individual outlying events scattered between 120 ms to 9800 ms were not included in the graph for clarity. The dwell time distribution under −40 mV appeared to be broader than that under −75 mV. The average dwell time for DNA blockades under the −75 mV and under −40 mV was 9.2 ms and 22.1 ms respectively (only the events less than 50 ms under −40 mV were used for the calculation). As a comparison, the distribution of dwell time for the 35-bp dsDNA were also included (FIG. 10). The average of the dwell times in this case was 0.53 ms. Therefore, it can be concluded that the dwell time of DNA translocation was affected by applied voltage and the size of DNA.

Figure 12A:
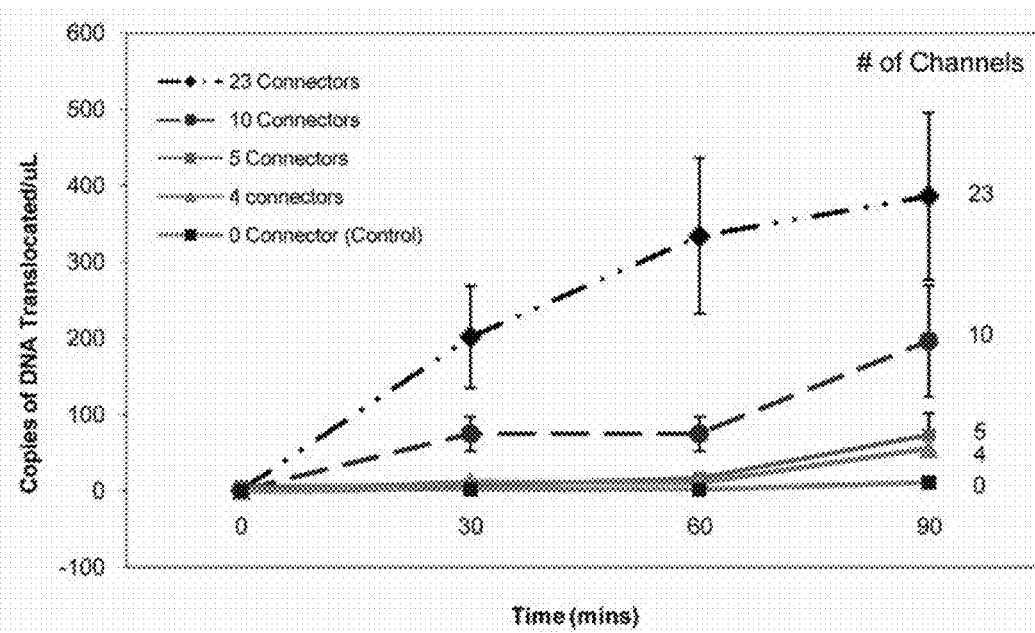
FIG. 12 shows Quantitative PCR (Q-PCR) analysis of DNA translocation under various conditions. a, Q-PCR analysis of DNA translocating through different numbers of membrane-incorporated, conductive channel-forming modified DNA-packaging motor protein connectors. The error bars represent the measurement errors for each sample under identical Q-PCR conditions. b, Q-PCR analysis of DNA molecules when leaking occurred. The error bars represent the standard deviations of the mean from three independent experiments.

To verify the passage of dsDNA through the apertures formed by the viral DNA-packaging motor protein connectors to create conductive channels, quantitative PCR (Q-PCR) was used to quantify the translocation of 141-bp DNA under a constant voltage. DNA was added to the trans-side and samples were taken from the cis-side for quantification at 30 minute intervals. For comparison, control experiments were performed in the absence of viral DNA-packaging motor protein connectors (FIG. 11). Experiments with connector insertions in bilayer lipid membranes (BLMs) showed an increase in the number of DNA molecules in the cis-chamber over time (N=9 experiments). In contrast, in the absence of connectors the number of DNA molecules in the cis-chamber remained undetectable over the 90-minute time course (N=4 experiments). Moreover, the DNA translocation rate was affected by the number of inserted viral DNA-packaging motor protein connectors (FIG. 12).

Figure 12B:
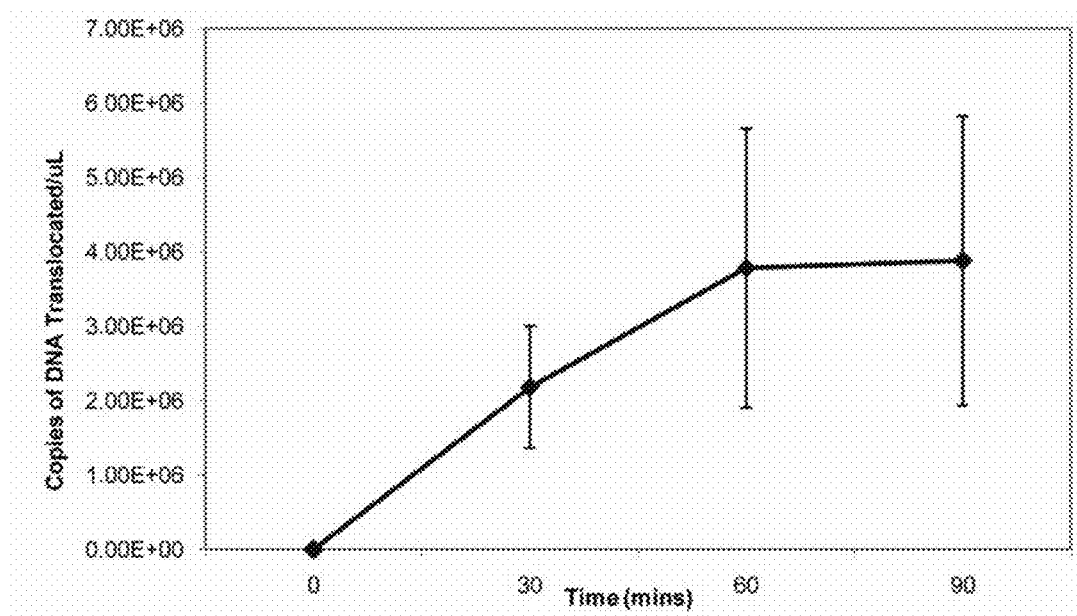

To verify that the increase of the DNA copy number in the cis-chamber was due to DNA translocation through the conductive channels formed by the apertures of the viral DNA-packaging motor protein connectors rather than membrane leakage, three additional experiments were carried out under the conditions of known leakage of BLM or partitions. When leaking occurred, the copy number of DNA per ul of solution in the cis-chamber was approximately $10^4$-$10^5$ fold higher than those experiments without leakage (FIG. 12B).

Example 3

Re-Engineering of dsDNA Viral DNA-Packaging Motor Protein Connectors for Nucleic Acid Translocation Double-stranded DNA viral DNA-packaging motor protein connectors' pore size and conductance are modulated through engineering to vary aperture dimensions, surface hydropathy profile, freedom of movement of flexibility domain and/or affinity/alignment domain interaction with membrane bilayers and nature of the particular affinity binding site, all as described above. The electrophysiological, chemical and mechanical properties of the modified connector as incorporated into a membrane layer to form a conductive channel are characterized under different conditions, such as ionic strength, pH, and temperature. The orientation of the connector channel for DNA directional transmembrane transportation is determined as described herein, and condensed dsDNA loading into giant liposomes is performed under applied transmembrane electrical potentials. Unidirectional transmembrane translocation of nucleic acids into liposomal lumens precedes delivery of genetic information to recipient cells in vitro and/or in vivo, and also precedes generation of liposomal or other membrane bounded bioreactors.

Example 4

Modified Membrane-Incorporated Viral DNA-Packaging Motor Protein Connector Conductive Channel as a Stochastic Sensing Machine for Combined Analyte Capture and Fingerprinting in Single Molecule Analysis Pairs of His tag/Anti-His tag antibody, Strep tag/Streptavidin, Biotin/Streptavidin, Strep tag/Anti-strep antibody, and His-tag/Nickel-NTA pairs are used as model systems to demonstrate the membrane-incorporated modified dsDNA viral DNA-packaging motor protein connector transmembrane aperture's utility as a conductive channel-based single molecule detector. The connector is modified by fusing at the N- and/or C-termini with an affinity/alignment domain that is a single chain antibody or with a peptide having desired affinity-binding specificity following identification in phage-display or with an RNA aptamer and is designed as described above to be capable of both analyte capture (i.e., detectable alteration of conductance upon specific analyte binding) and analyte fingerprinting (i.e., amplitude- and/or duration-dependent generation of a conductance profile of altered conductance over a plurality of timepoints in response to a test analyte and under defined conditions that is compared to a reference conductance profile for known analytes, to characterize the test analyte). The combination of analyte detection by capture and analyte characterization by fingerprinting provides sensitivity enhancement (i.e., ability to detect and/or characterize that is greater, in a statistically significant manner, than would be the ability if only capture functionality was present) for identification of molecules at very low concentration. Detection and characterization of analytes occurs at earlier stages of disease for diagnostic purposes, and sensitivity of environmental surveillance for analytes is enhanced.

Example 5

Sensing and Fingerprinting of Double-Stranded DNA

Various mutations are made in the polypeptide sequences that influence the dimensions, hydropathy, charge and conductivity properties, and solvent accessibility of the aperture domain (lumen) and/or the N- and/or C-termini, including modifications to provide different flexibility domains and/or affinity/alignment domains, of the DNA-packaging motor protein connector that is capable of forming a transmembrane conductive channel are made, to adjust the channel properties for enhancing sensitivity and resolution of analyte detection and characterization. Translocations of several types and shapes of nucleic acid polymers are characterized through conductance measurements including generation of conductance profiles such as profiles over a plurality of timepoints of the amplitude and duration of altered conductance. Detection of DNA mismatch mutations in cancer cells is tested by contacting cancer cell-derived DNA with the conductive channel-containing membrane. Procedures for reducing DNA translocation speed are developed by varying assay conditions (e.g., temperature, pH, ionic conditions, magnitude of applied electrical potential) and by varying modified DNA-packaging motor connector composition. The conductive channel is derivatized with channel-modifying chemicals in a controlled manner to slow the transmembrane passage (translocation) of dsDNA and conductance profiles are generated by which single nucleotides are recognized with high precision. The conductive channel-containing membrane is incorporated into a high throughput dsDNA sequencing apparatus.

Example 6

Ions as Analytes

Figure 13A:
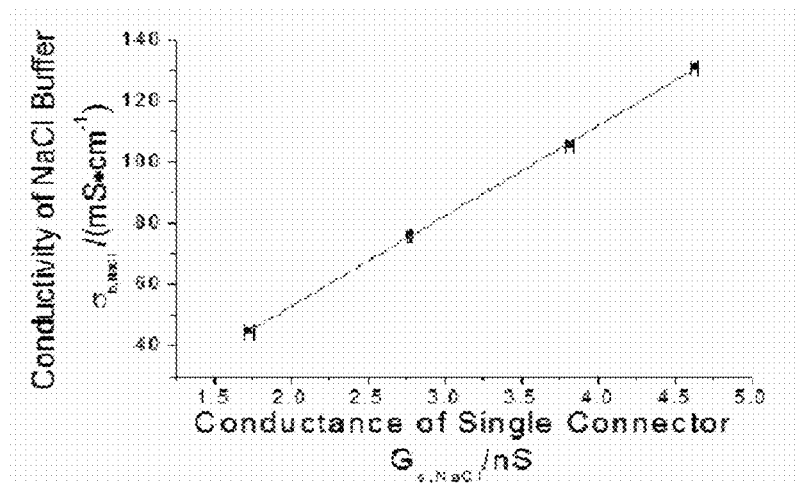
FIG. 13 shows FIG. 8. (A) Relationship of buffer conductance with connector channel conductance. (B) Relationship of connector channel conductance with number of inserted connectors in buffers containing different NaCl concentrations. (C) Comparison of conductance in buffers containing KCl and NaCl at 1 M.
Figure 13B:
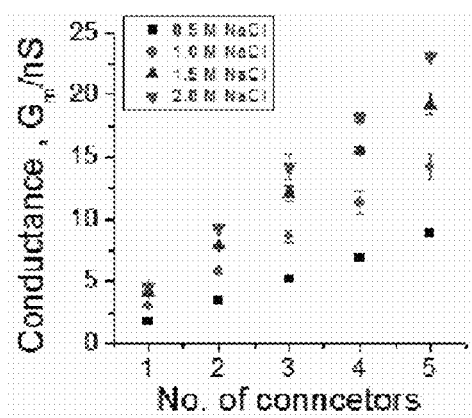
Figure 13C:
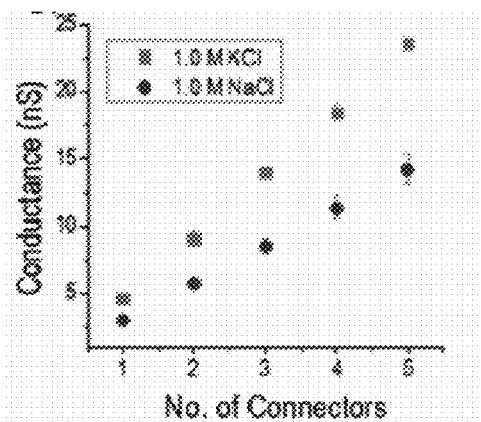

The conductance of a single modified viral DNA-packaging motor protein connector in a bilayer membrane (BLM) increased with the salt concentration in a strong linear relationship (FIG. 13). In addition, the conductance of the connector in BLM appeared to be ion dependent, with the conductance in KCl higher than that in NaCl, when the same salt concentration was used (FIG. 13B, C) Such properties of the connector channel in BLM make it possible to test the buffer concentrations and to differentiate ion species, as well as to tune the conductance.

Example 7

DNA as Analyte

Figure 14A:
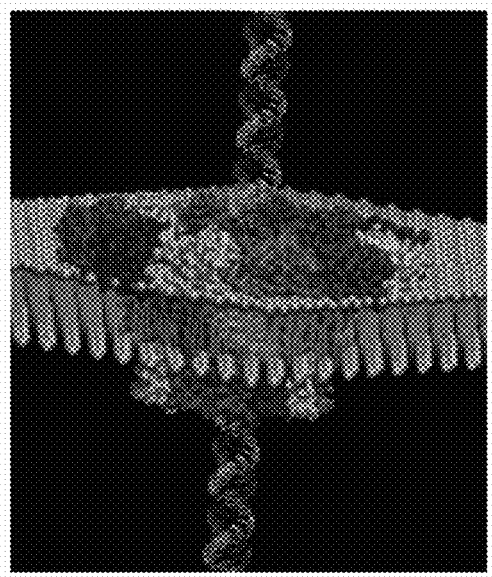
FIG. 14 shows (A) schematic of DNA translocating through the connector. (B) Histogram of current blockade induced by dsDNA. (C) Q-PCR analysis of the DNA translocated over time with varying number of channels.
Figure 14B:
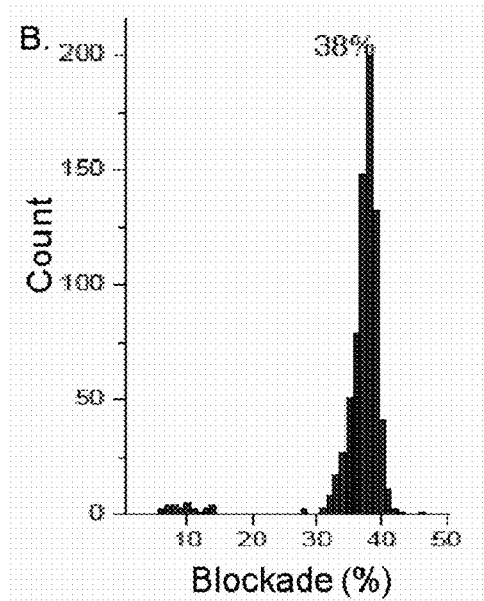
Figure 14C:
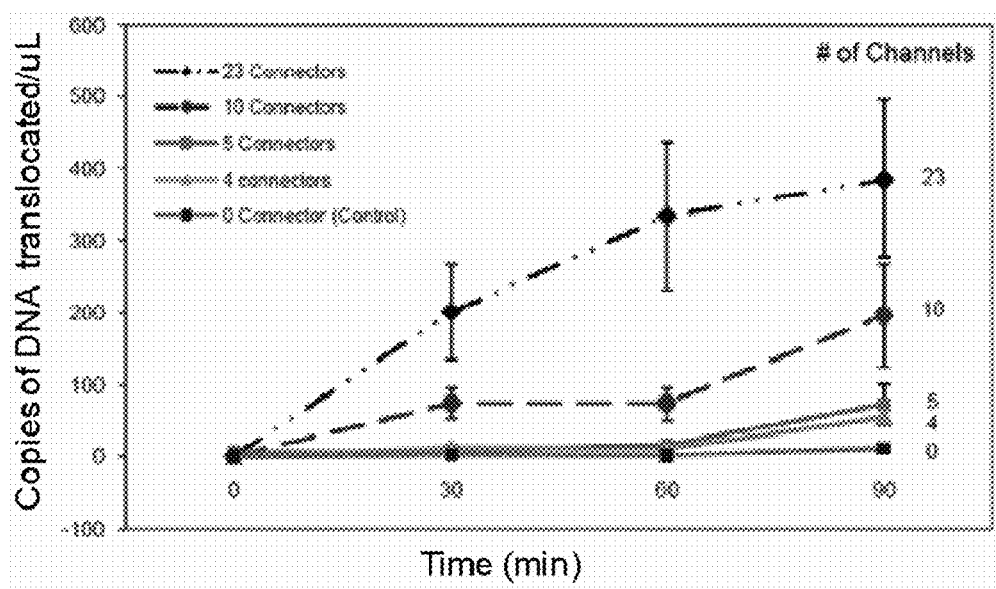

Linear and circular plasmid dsDNA (5.5 kb) were both used to examine translocation of dsDNA through the conductive channel formed by a membrane-incorporated modified viral DNA-packaging motor protein connector, as also described above in Examples 1 and 2. Linear DNA translocation induced numerous current blockades by about 30% (FIG. 8). When circular plasmid dsDNA was used, no translocation was observed (FIG. 8). However, after digestion by DNase I, both linear and circular plasmid DNA gave a burst of transient blockades (FIG. 8C, D). The results indicated that only linear dsDNA passed through the connector channels, while circular DNA did not. The DNA translocation was confirmed by Quantitative PCR of the DNA samples that passed through the pore using the SYBR Green kit (FIG. 14).

Figure 15A:
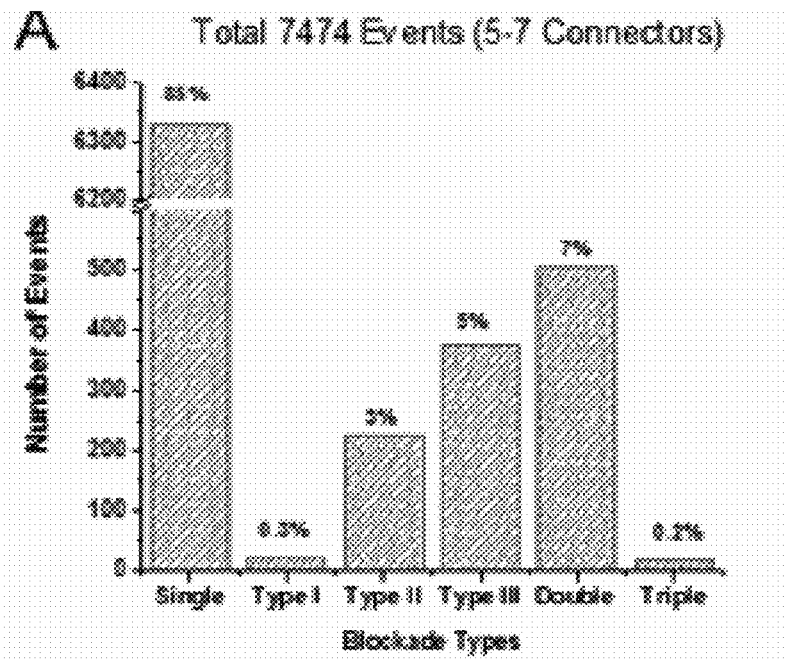
FIG. 15 shows translocation of folded DNA conformations. Histogram of current blockade of single events at discrete current levels with 5-7 modified phi29 gp10 DNA-packaging motor connector channels (A) and 12-14 channels (B). (C) Schematic illustration of folded DNA translocating through the modified connector channel. (D) Examples of recorded events with 5 kbp dsDNA at pH 8.
Figure 15B:
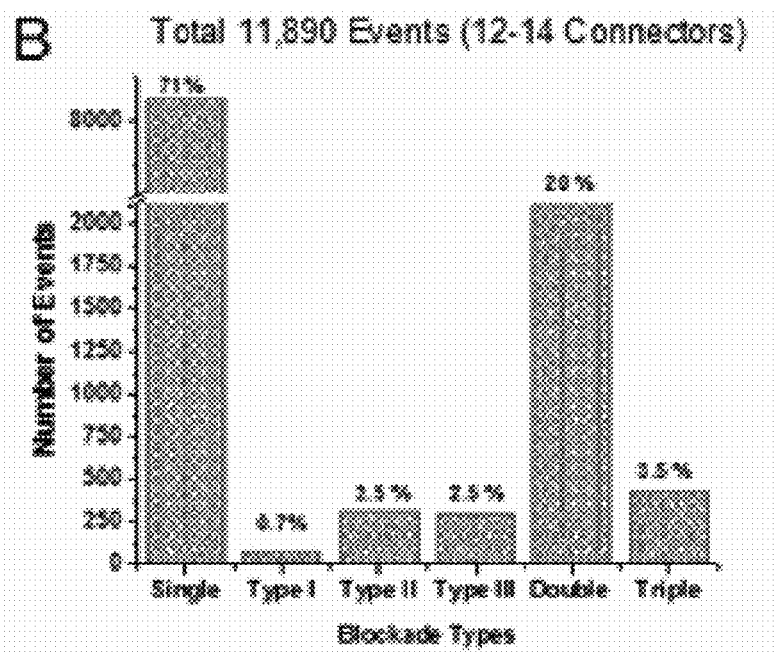
Figure 15C:
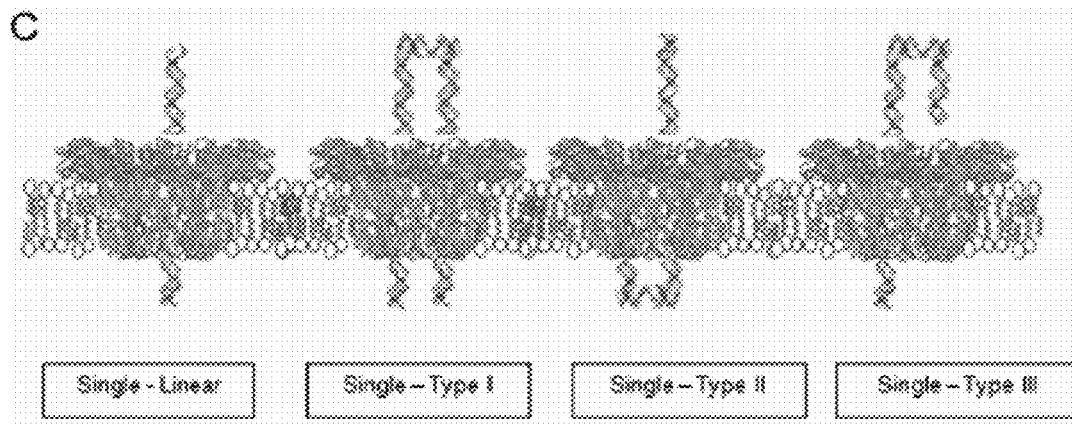
Figure 15D:
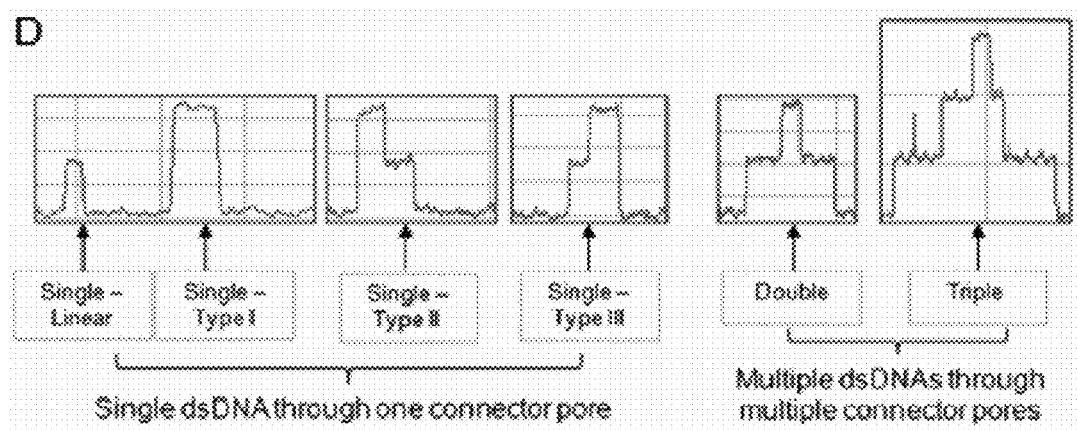
Figure 16A:
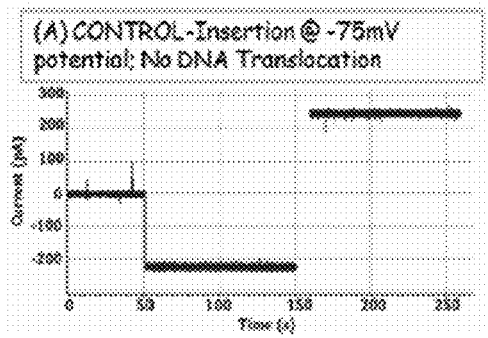
FIG. 16 shows one-way traffic of DNA translocation through modified phi29 gp10 DNA-packaging motor protein connector. (A) Control in the absence of DNA. (B) Connector insertion at positive potential (top) and DNA translocation at negative potential (bottom). (C) Connector insertion at negative potential (bottom) and DNA translocation at positive potential (top). (D) Connector insertion at negative potential (bottom) and DNA translocation at negative potential (bottom). (E-F) Current traces of bilayers containing a single connector under a ramping potential (2.2 mV/s) from −100 mV to +100 mV, demonstrating DNA translocation at (E) negative potentials only and (F) positive potentials only.
Figure 16B:
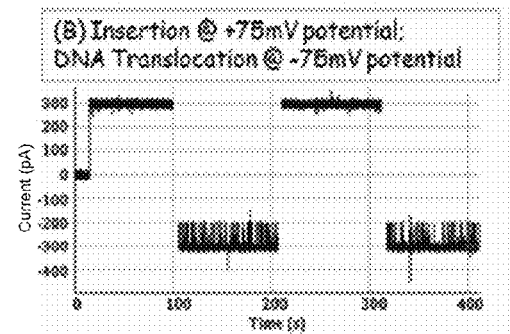
Figure 16C:
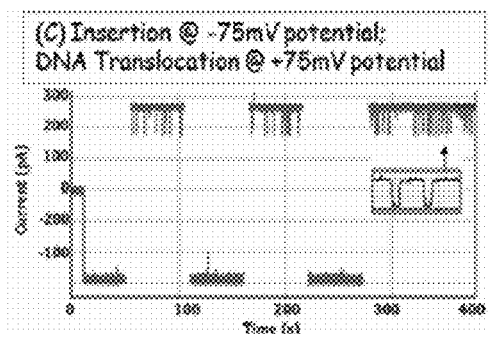
Figure 16D:
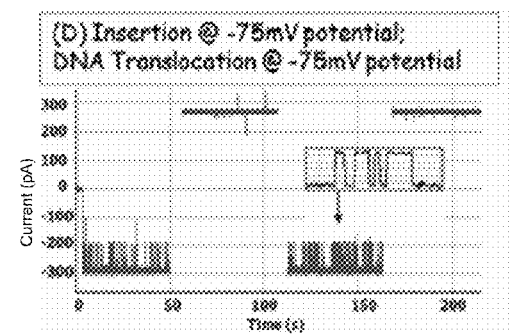
Figure 16E:
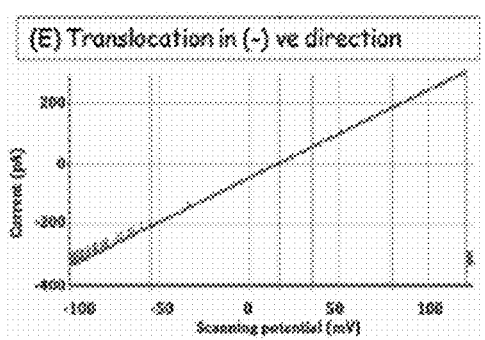
Figure 16F:
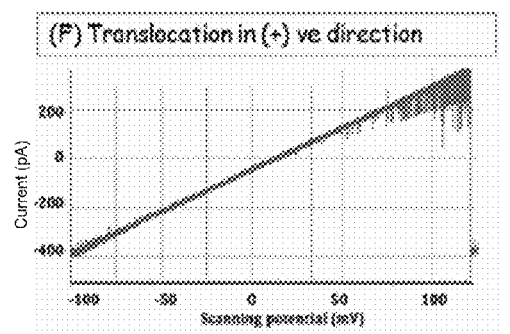
Figure 17A:
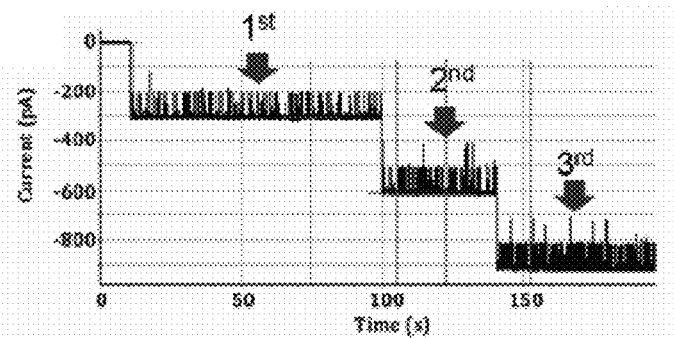
FIG. 17 shows DNA translocation under multiple modified phi29 gp10 connector insertion events. The "↓" denotes one orientation of connector insertion and the "↑" denotes opposite direction of connector insertion. (A) All three connectors were oriented in the same direction and DNA translocation rate increased with the number of connectors. (B) The first connector was oriented in the opposite direction and no translocation was observed. Subsequently, DNA translocation and an increase in rate were observed after second and third insertions respectively. (C) No translocation was observed following the first two connector insertions. After the next two insertions, both were actively translocating DNA. (D) Only the first connector translocated DNA, since the rate of DNA translocation remained unchanged when the $2^{nd}$ and $3^{rd}$ connectors were inserted.
Figure 17B:
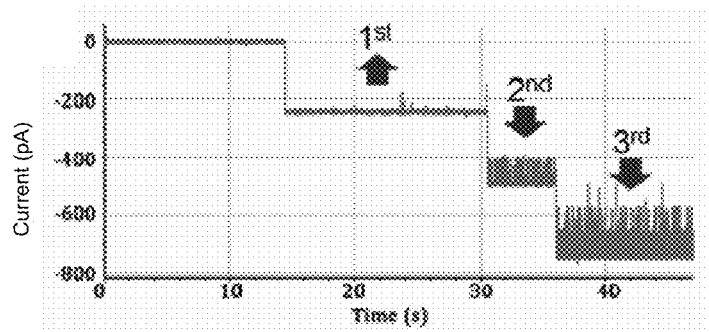
Figure 17C:
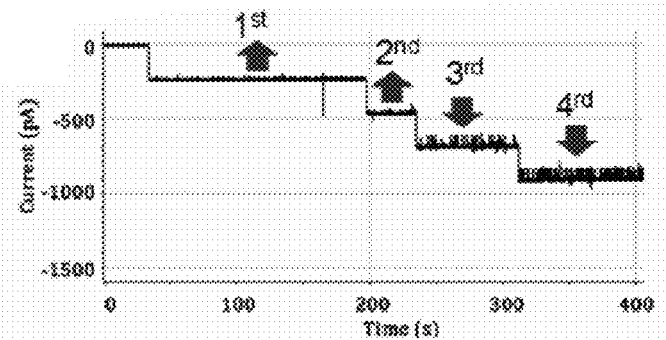
Figure 17D:
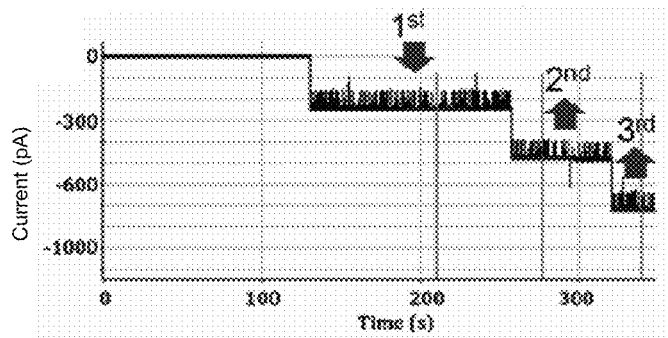

The conductive channel connector aperture in BLM differentiated the sizes of linear dsDNA based on their characteristic dwell times, and differentiated linear dsDNA from folded dsDNA. When a 5 kbp dsDNA translocated through the conductive channel under an applied potential, different types of current blockade events were observed (FIG. 15). The persistence length of dsDNA in the presence of 1M ionic strength is ~150 bp (Baumann et al., 1997 *Proc. Nat. Acad. Sci USA* 94:6185), and DNA translocation has been observed through synthetic nanopores (Storm et al., 2005 *Phys Rev E Stat Nonlin Soft Matt Phys* 71(5 Pt 1):51903; Chen et al., 2004 *Nano Lett.* 4:2293). Similar observations for the herein described modified phi29 DNA-packaging motor protein connector channel were demonstrated by discrete levels in current blockade arising from a single translocation event (Single linear events type I, II and III) (FIG. 15). The double (and triple) events were attributed to two (and three) DNA molecules translocating through two (and three) channels simultaneously (FIG. 15D). Similar events were observed using 500 bp dsDNA as the analyte.

One-way traffic (unidirectional) DNA translocation was observed through a modified phi29 DNA-packaging motor protein connector channel in a BLM. A single modified DNA-packaging motor protein connector was inserted in a BLM with DNA premixed in both the cis- and the trans-chambers. When the applied voltage was alternated between positive and negative potentials, DNA translocations were only observable in one direction (either positive only or negative only) as shown in FIG. 16. According to non-limiting theory it appeared that the DNA could only pass through the conductive channel aperture formed by the connector in one direction, an interpretation that was consistent with the results of dsDNA translocation experiments performed with multiple connector insertions (FIG. 17).

Figure 18A:
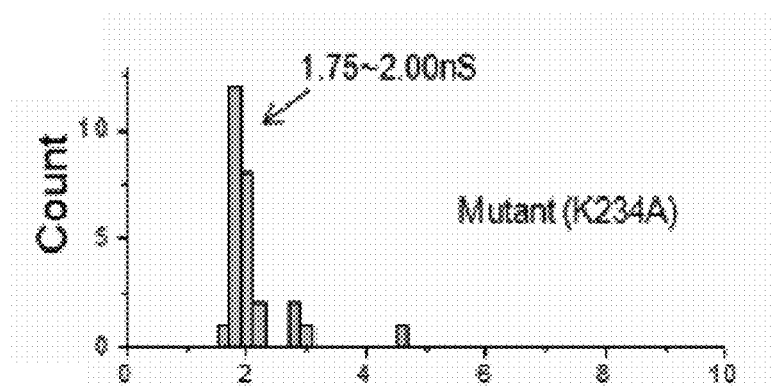
FIG. 18 shows (A) Histogram of conductance for mutant (K234A) modified phi29 gp10 DNA-packaging motor protein connector incorporated into a membrane layer. (B) Histogram of conductance for wild-type phi29 connector.
Figure 18B:
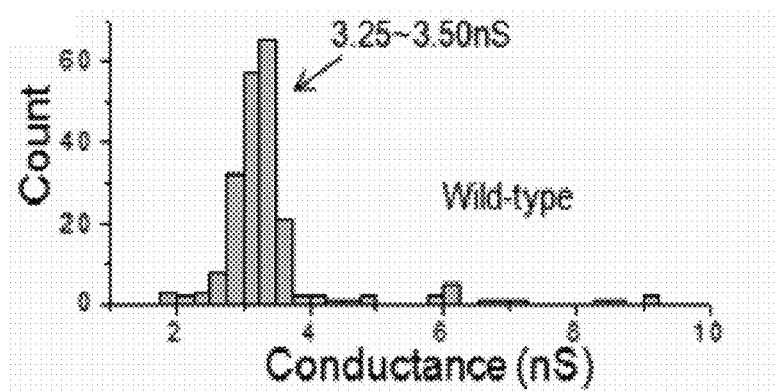

Further modifying the amino acid sequence of the modified phi29 DNA-packaging motor protein connector channel resulted in alterations of the channel conductance. When the lysine at position 234 inside the connector tunnel (aperture) was replaced by cysteine (K234C) [SEQ ID NO:42] or alanine (K234A) [SEQ ID NO:41], the current jump induced by a single modified connector inserted into the BLM was smaller than that of the wild-type connector (FIG. 18).

Example 8

Specifically Binding Polypeptide (Antibody) as Analyte

This example describes generation of a conductance profile "fingerprint" of specifically captured polypeptide analyte molecules (antibody) following their interaction with the affinity/alignment domain of a modified DNA-packaging motor protein connector as described herein.

Figure 19:
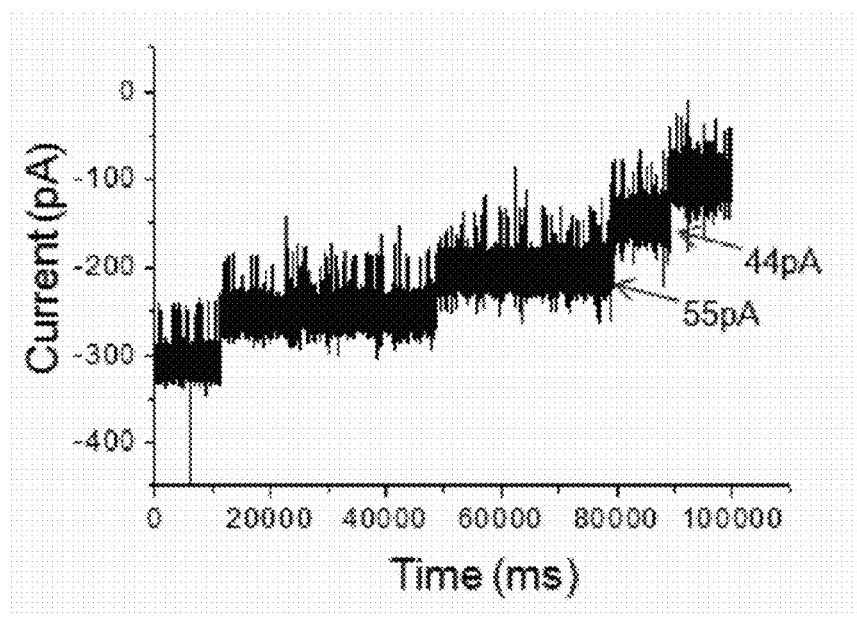
FIG. 19 shows that addition of anti-His tag antibody to one side of the chamber blocked, in a stepwise fashion, the conductive channel formed by the aperture of a modified phi29 gp10 DNA-packaging motor protein connector comprising SEQ ID NO:1 having a C-terminal hexahistidine [SEQ ID NO:25] affinity/alignment domain.

The phi29 DNA-packaging motor protein connector was re-engineered as described above with a His$_6$-tag as an affinity/alignment domain at its C-terminus. The re-engineered connector was inserted in a BLM and showed a typical current jump under an applied potential under assay conditions essentially as described above. When a specific anti-His-tag antibody was added in the sample chamber, a step-wise decrease in the current was observed, with each small step being about 20% of the total current jump for a single connector pore (FIG. 19). The step-wise decrease in current jump was due to the sequential binding of one antibody molecule to each of the twelve His-tags on the dodecameric connector, which sequential binding decreased the overall size of the aperture forming the conductive channel. This approach is contemplated for single molecule identification by the combination of (i) capturing analyte through this type of antibody-antigen specific binding interaction and (ii) "fingerprinting" the analyte by generating an analyte-characteristic conductance profile (e.g., a blockade pattern such as the one shown in FIG. 19).

Example 9

Fluorescence Resonance Energy Transfer (FRET) for DNA Sequencing

This example uses custom designed highly sensitive single molecule dual channel imaging system to detect dual labeled dsDNA system.

A customized highly sensitive imaging system in single fluorophore detection is established in our lab. The apparatus has synchronous optical and electrical design setup, using solid state channel and single protein channel. In this device, the silicon chip containing a SiN membrane is replaced by the BCH Chamber (Eastern Scientific LLC) containing the Teflon membrane. The refractive indices of the buffer used in the cis chamber, nw is about 1.33. Since the glass refractive index, ng is 1.5, a solution containing 7M CsCl and 10 mM Tris, pH of 8.5 with a index of nCs=1.41 is placed between the water buffer and the glass for total internal reflection.

To solve the problem for single pore sensing, which is the feasibility to control the number of connectors in the BLM, we had to quantify and monitor the number of connectors inserted in the BLM. To stop any further insertion of connectors into the membrane, an automated patch clamp was incorporated into our system.

This automated system has several advantages: (1) It is automated; (2) the cis- and trans-chambers are miniaturized with provisions for efficient solution exchange; (3) single liposomes containing single connector can be patched efficiently. This system was originally designed for the patching single cells. Preliminary data demonstrated the successful patch of liposome/connector complexes to form connector channel in the lipid membrane or cell membrane (data not shown).

In this system, buffer removal and sample exchange is monitored and controlled at will using the automated computer system. As soon as the desired number of connector insertion reaches the level in interest, immediate removal of the buffer and/or sample followed by thorough washing stops additional connector insertions. A single connector-reconstituted liposome is patched from the inside as a whole cell and is converted into a membrane by suction with automatic force control. A Pipette is moved between the monitor system and the imaging microfluidic chamber. A custom design pipette tip ensures the presence of a stable pore, and more importantly, the connector incorporation process does not depend on vesicle fusion. Hence, the membrane pore system is monitored and assembled under control with high success rates under a wide range of experimental conditions.

The Use of Fluorescence Resonance Energy Transfer (FRET) for Detection of DNA

For a given dye pair, the detectable FRET event ranges only from 1 to 10 nm. Using single-molecule FRET with objective type TIRF for detection will narrow the depth of focus and provide better spatial resolution in z-direction when a fluorescently labeled DNA chain is passing through the pore. The connector or the active motor embedded in the membrane will be labeled with donor fluorophores at the N- or C terminus of the connector as described previously. The possible donor/acceptor pairs are listed in Table 2.

TABLE 2

Proposed donor and acceptor for Detection via FRET

| Choice of Donor | Choice of Acceptor |
|---|---|
| QD525 | Cy3 ™ |
| Alexa Fluor ™ 488 | Alexa Fluor ™ 546 |
| | Tetramethylrhodamine |
| | TAMRA ™ |
| QD655 | Cy5.5 |
| | Alexa Fluor ™ 700 |
| | IRDye ® 700 |
| QD705 | Alexa Fluor ™ 750 |
| Alexa Fluor ™ 700 | Alexa Fluor ™ 790 |
| | Dy750 |

Quantum dots (QD) have been applied in single-molecule FRET. QDs as donors have the following advantages: 1) very bright and long-lasting without photobleaching; 2) narrow fluorescence emission spectra for reducing the possibility of cross-talk with acceptor emission; 3) broad excitation spectra, thus different QDs can be excited with same laser wavelength in UV or short visible spectra to avoid the use of multiple lasers in the experiment and eliminate cross excitation of acceptors; 4) various functionalized QDs and excitation filter sets are commercially available, providing versatilities in connector labeling.

Attaching FRET Donors to the Channel

Label the Connector with Donors:

Cysteine residue or a biotin group will be introduced to the connector for incorporating the donors at the N- or C-terminal ends of the 12 copies of the connector subunits. We have previously shown that some terminal modifications have little or no effect on channel formation or its ability to package dsDNA69, thus verifying its authenticity. As the connector is composed of 12 subunits of gp10 protein, there are a total of 12 re-engineered tags on each connector molecule. The QD525 and QD655 will be attached to the terminus of the same connector by mixing them at a 1:1 molar ratio during labeling via strep/biotin or SH-Maleimide interactions.

Label the DNA with Two Acceptors Corresponding to Two Donors

Figure 20:
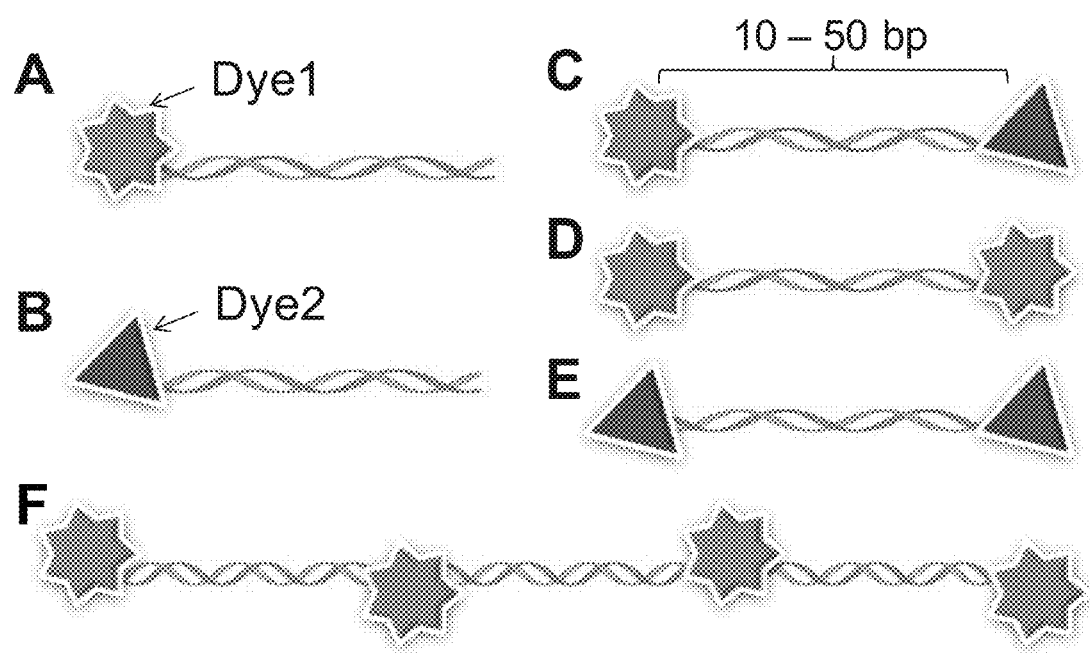
FIG. 20 shows schematic of construction of different short dsDNA chains w/ acceptor dyes.
Figure 21:
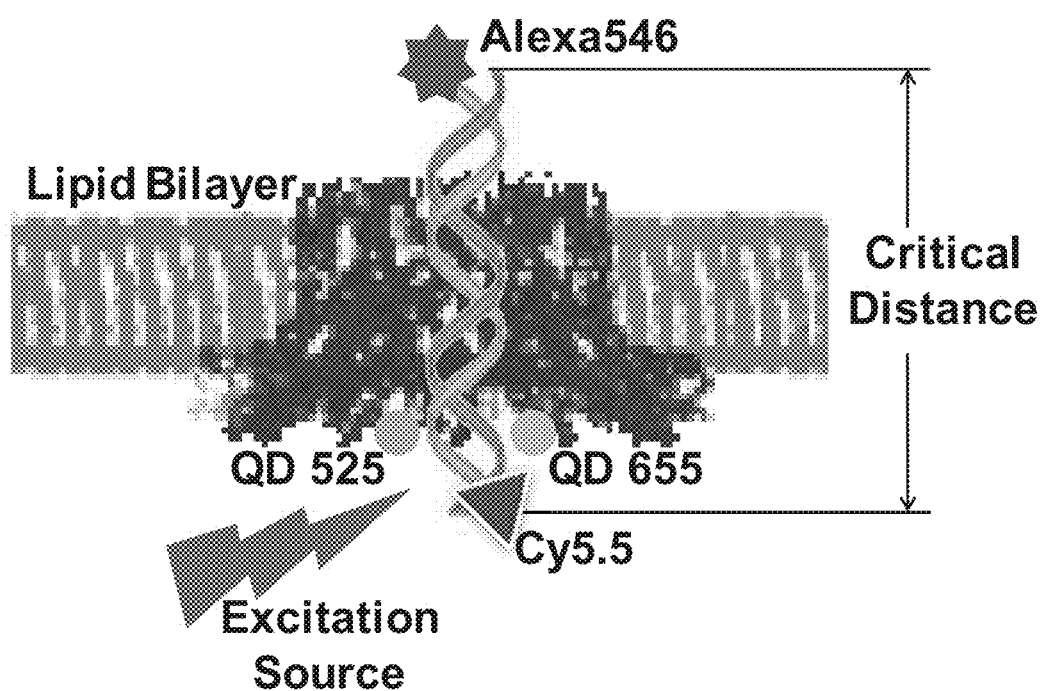
FIG. 21 shows schematic of the design for FRET detection of dual labeled short dsDNA chains.

The proof of concept for distinguishing two different nucleotides that pass through the connector pore is shown by detecting two different fluorescence signals. Short dsDNA chains is constructed using customized fluorescent DNA oligos with two dyes attached between 2 to 50 bp (FIG. 20). Acceptors to be excited by donors QD525 and QD655 are listed in Table 2. The design of labeling the DNA with acceptors as a proof of concept is shown in FIG. 20. Near UV Laser is used to excite the QDs, and FRET is detected synchronously with the electrical signals. Proper dichroic mirrors and band pass filters are used to exclude the signals from the donor emissions while transmitting the acceptor emissions with high efficiency. The distance for FRET is about 1-10 nm, corresponding to a range of 1-30 bp. The closer the dyes are, the stronger the FRET signal. The dual-labeled short dsDNA chains (FIG. 20C-E) is used to provide empirical information of how close between two dyes the system can discriminate (FIG. 21).

Figure 22:
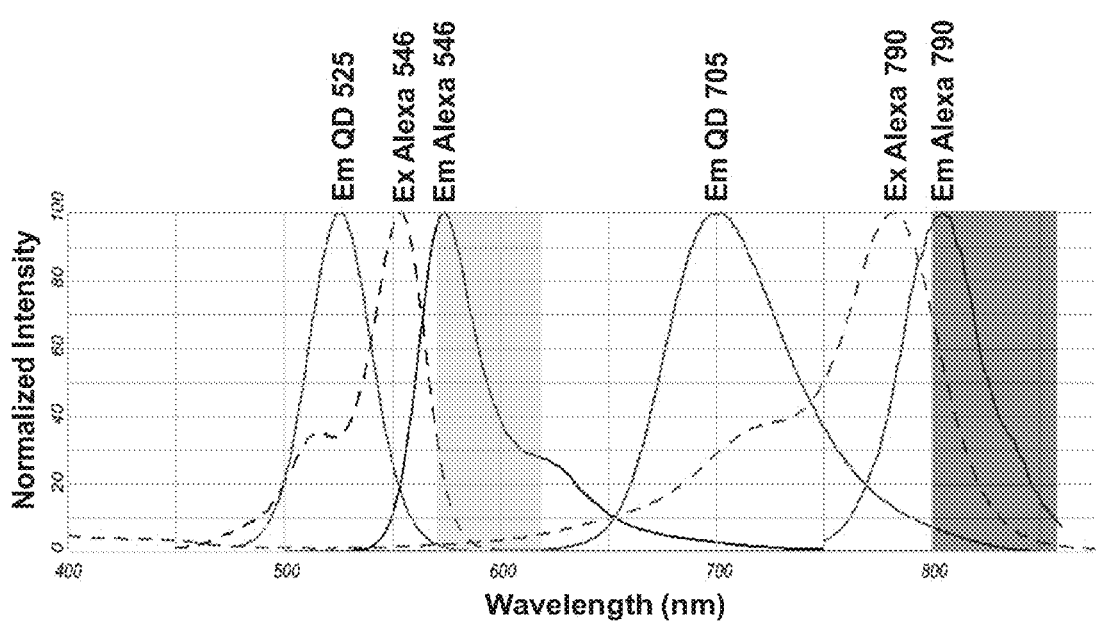
FIG. 22 shows comparison of the fluorescence spectra of selected donors (QD525, QD705) and acceptors (Alexa546, Alexa790). Yellow and gray blocks indicate the possible choices of band pass filters.

In the case emission spectrum of Alexa546 and the excitation spectrum of Cy5.5 slightly overlaps, very small energy transfer might occur if they are within close proximity in DNA. Under those conditions Alexa790 is used to replace Cy5.5 as the acceptor for donor QD705 (table 2). Alexa790 is an IR dye and will not have substantial overlap with the emission spectra of Alexa546 (FIG. 22).

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An artificial conductive channel-containing membrane complex, comprising:

(a) A membrane layer; and (b) an isolated viral DNA-packaging motor connector protein comprising a homododecamer of viral DNA-packaging motor connector protein polypeptide subunits, wherein said viral DNA-packaging motor connector protein is incorporated into the membrane layer to form an aperture through which conductance can occur when electrical potential, is applied across the membrane, wherein each of said viral DNA-packaging motor connector protein polypeptide subunits comprises:

said aperture domain having an amino terminus and a carboxyl terminus;

and either or both of terminus has
(i) at least one flexibility domain that comprises a polypeptide of 4, 5, 6, 7, 8, 9, 10, 11, 12, 13, 14, 15, 16, 17 or 18 contiguous uncharged amino acids and that is fused to at least one of the amino terminus and the carboxyl terminus, and
(ii) at least one affinity/alignment domain.

2. The conductive channel-containing membrane of claim 1 wherein each of said subunits comprises:
(a) an aperture domain that comprises an isolated viral connector protein polypeptide having an amino terminus and a carboxyl terminus; and
(b) either or both of terminus has
(i) at least one flexibility domain that comprises a polypeptide of 4, 5, 6, 7, 8, 9, 10, 11, 12, 13, 14, 15, 16, 17 or 18 contiguous uncharged amino acids and that is fused to at least one of the amino terminus and the carboxyl terminus of (a), and
(ii) at least one affinity/alignment domain.

3. The conductive channel-containing membrane of claim 1 wherein each of said subunits comprises
(a) an aperture domain that comprises an isolated viral connector protein polypeptide having an amino terminus and a carboxyl terminus; and
(b) either or both of terminus has
(i) at least one flexibility domain that comprises a polypeptide of 4, 5, 6, 7, 8, 9, 10, 11, 12, 13 or 14 contiguous uncharged amino acids and that is fused to at least one of the amino terminus and the carboxyl terminus of (a), and
(ii) at least one affinity/alignment domain that comprises a polypeptide of formula X1a-X1a-X2a-X1b-X1b-X1b-X3-X2b and that is fused to the flexibility domain, wherein each X1a is independently either any uncharged amino acid or no amino acid, each X1b is independently any uncharged amino acid, X2a is a positively charged amino acid selected from lysine, arginine and histidine, X3 is a negatively charged amino acid selected from glutamic acid and aspartic acid, and X2b is a positively charged amino acid selected from lysine, arginine and histidine.

4. The conductive channel-containing membrane of claim 1 wherein each of said subunits comprises
(a) an aperture domain that comprises an isolated viral connector protein polypeptide having an amino terminus and a carboxyl terminus; and
(b) either or both of terminus has
(i) at least one flexibility domain that comprises a polypeptide of sequence Gly-Gly-Gly-Gly-Gly-Gly as set forth in SEQ ID NO:23 and that is fused to the carboxy terminus of (a), and
(ii) at least one affinity/alignment domain that is fused to the flexibility domain.

5. The conductive channel-containing membrane of either claim 2 or claim 4 wherein the affinity/alignment domain comprises a polypeptide that is selected from the group consisting of
(i) a Strep-II tag as set forth in SEQ ID NO:22 [WSHPQR-FEK],
(ii) a polyhistidine polypeptide tag of 3, 4, 5, 6, 7, 8, 9, 10, 11 or 12 contiguous histidine residues,
(iii) a polyarginine polypeptide of 3, 4, 5, 6, 7, 8, 9, 10, 11 or 12 contiguous arginine residues,
(iv) an HIV Tat polypeptide of sequence YGRKKRRQRR [SEQ ID NO:39], and
(v) a peptide tag of sequence DRATPY [SEQ ID NO:40].

6. The conductive channel-containing membrane of claim 1 wherein each of said subunits is selected from the group consisting of:
(i) C-His6-gp10/K234A as set forth in SEQ ID NO:41;
(ii) C-His6-gp10/K234C as set forth in SEQ ID NO:42;
(iii) C-His6-gp10/C76S/C265S/K234C as set forth in SEQ ID NO:43;
(iv) Δ1-14/gp10-Strep-II as set forth in SEQ ID NO:44; and
(v) Gp10/Δ285-309-Strep-II as set forth I SEQ ID NO:45.

7. The conductive channel-containing membrane of claim 1 wherein the viral DNA packaging motor connector protein polypeptide subunits are selected from the group consisting of
(i) all or a transmembrane aperture-forming portion of bacteriophage phi29 DNA-packaging motor connector protein polypeptide having the amino acid sequence set forth in SEQ ID NO:1 [Ace. No. ACE96033];
(ii) all or a transmembrane aperture-forming portion of phage T4 DNA-packaging motor connector protein polypeptide having the amino acid sequence set forth in SEQ ID NO:7 [Ace. No. NP_049782];
(iii) all or a transmembrane aperture-forming portion of phage lambda DNA-packaging motor connector protein polypeptide having the amino acid sequence set forth in any one of SEQ ID NOS:8-11 [Ace. Nos. gi 549295, gi 6723246, gi 15837315, gi 16764273];
(iv) all or a transmembrane aperture forming portion of phage SPP1 DNA-packaging motor connector protein polypeptide having the amino acid sequence set forth in SEQ ID NO: 12 [Ace. No. P54309];
(v) all or a transmembrane aperture-forming portion of phage P22 DNA-packaging motor connector protein polypeptide having the amino acid sequence set forth in SEQ ID NO:13 [Ace. No. AAA72961];
(vi) all or a transmembrane aperture-forming portion of phage P2 DNA-packaging motor connector protein polypeptide having the amino acid sequence set forth in SEQ ID NO:14 [Ace. No. NP_046757];
(vii) all or a transmembrane aperture-forming portion of phage P3 DNA-packaging motor connector protein polypeptide;
(viii) all or a transmembrane aperture-forming portion of phage T3 DNA-packaging motor connector protein polypeptide having the amino acid sequence set forth in SEQ ID NO:15 [Ace. No. CAA35152];
(ix) all or a transmembrane aperture-forming portion of phage T5 DNA-packaging motor connector protein polypeptide having the amino acid sequence set forth in SEQ ID NOS: 16-19 (Accession numbers AAX12078, YP_006980; AAS77191; AAU05287); and
(x) all or a transmembrane aperture-forming portion of phage T7 DNA-packaging motor connector protein polypeptide having the amino acid sequence set forth in SEQ ID NO:20 [Ace. No. NP_041995].

8. The conductive channel-containing membrane of claim 1 wherein the viral DNA-packaging motor connector protein homododecamer polypeptide subunits comprises all or a transmembrane aperture-forming portion of a double-stranded DNA bacteriophage DNA-packaging motor connector protein.

9. The conductive channel-containing membrane of any one of claim 2, 3 or 4 wherein the viral connector protein polypeptide is selected from the group consisting of
(i) all or a transmembrane aperture-forming portion of bacteriophage phi29 DNA-packaging motor connector protein polypeptide having the amino acid sequence set forth in SEQ ID NO:1 [Acc. No. ACE96033];

(ii) all or a transmembrane aperture-forming portion of phage T4 DNA packaging motor connector protein polypeptide having the amino acid sequence set forth in SEQ ID NO:7 [Acc. No. NP_049782];

(iii) all or a transmembrane aperture-forming portion of phage lambda DNA-packaging motor connector protein polypeptide having the amino acid sequence set forth in any one of SEQ ID NOS:8-11 [Acc. Nos. gi 549295, gi 6723246, gi 15837315, gi 16764273];

(iv) all or a transmembrane aperture-forming portion of phage SPP1 DNA-packaging motor connector protein polypeptide having the amino acid sequence set forth in SEQ ID NO:12 [Acc. No. P54309];

(v) all or a transmembrane aperture-forming portion of phage P22 DNA-packaging motor connector protein polypeptide having the amino acid sequence set forth in SEQ ID NO:13 [Acc. No. AAA72961];

(vi) all or a transmembrane aperture-forming portion of phage P2 DNA-packaging motor connector protein polypeptide having the amino acid sequence set forth in SEQ ID NO:14 [Acc. No. NP_046757];

(vii) all or a transmembrane aperture-forming portion of phage P3 DNA-packaging motor connector protein polypeptide;

(viii) all or a transmembrane aperture-forming portion of phage T3 DNA-packaging motor connector protein polypeptide having the amino acid sequence set forth in SEQ ID NO:15 [Acc. No. CAA35152];

(ix) all or a transmembrane aperture-forming portion of phage T5 DNA-packaging motor connector protein polypeptide having the amino acid sequence set forth in SEQ ID NOS:16-19 (Accession numbers AAX12078, YP_006980; AAS77191; AAU05287); and (x) all or a transmembrane aperture-forming portion of phage T7 DNA-packaging motor connector protein polypeptide having the amino acid sequence set forth in SEQ ID NO:20 [Acc. No. NP_041995].

10. The conductive channel-containing membrane of claim 1 wherein the viral DNA-packaging motor connector protein comprises a detectable label.

11. The conductive channel-containing membrane of claim 10 wherein the detectable label is selected from the group consisting of a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label.

12. The conductive channel-containing membrane of claim 11 wherein the affinity label is selected from the group consisting of, avidin, streptavidin, biotin, an aptamer, an antibody, a lectin, an oligosaccharide, a nucleic acid, an enzyme, a metal ion-binding polypeptide, a Strep-11 tag as set forth in SEQ ID NO:22 [WSHPQRFEK], a polyhistidine polypeptide tag of 3, 4, 5, 6, 7, 8, 9, 10, 11 or 12 contiguous histidine residues, a Strep-I tag, a FLAG® peptide tag, a Myc peptide tag, glutathione-S-transferase, maltose binding protein, S. aureus protein A, protein G, HIV Tat polypeptide [SEQ ID NO:39], a peptide having the amino acid sequence DRATPY [SEQ ID NO:40], glutaredoxin-2, and a phage-displayed peptide that specifically binds an affinity ligand.

13. The conductive channel containing membrane of claim 12 wherein the antibody is selected from the group consisting of an intact immunoglobulin, a single-chain antibody, an scFv, a Fab and a (Fab)'2.

14. The conductive channel-containing membrane of claim 1 wherein the membrane layer comprises a lipid layer.

15. The conductive channel-containing membrane of claim 14 wherein the lipid layer comprises amphipathic lipids.

16. The conductive channel-containing membrane of claim 14 wherein the lipid layer is selected from the group consisting of a planar membrane layer and a liposome.

17. The conductive channel-containing membrane of claim 15 wherein the amphipathic lipids comprise phospholipids and the lipid layer comprises a lipid bilayer.

18. The conductive channel-containing membrane of claim 16 wherein the liposome is selected from the group consisting of a multilamellar liposome and a unilamellar liposome.

19. The conductive channel-containing membrane of claim 1 wherein the incorporated viral DNA-packaging motor connector protein is mobile in the membrane layer.

20. The conductive channel-containing membrane of claim 1 which is capable of translocating double-stranded DNA through the aperture when the electrical potential is applied.

21. The conductive channel-containing membrane of claim 1 in which conductance occurs without voltage gating when the electrical potential is applied.

22. A method of making a conductive channel-containing membrane, comprising:
(a) preparing dried amphipathic lipids on a solid substrate by contacting a first solution comprising amphipathic lipids and an organic solvent with the solid substrate and substantially removing the solvent; and
(b) resuspending the dried amphipathic lipids in a second solution that comprises an aqueous solvent, an osmotic agent and a plurality of isolated viral DNA-packaging motor connector protein submit polypeptides,
wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
wherein said plurality of isolated viral DNA packing motor connector protein subunit peptides are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when an electrical potential is applied across the membrane, and thereby making a conductive channel-containing membrane.

23. A method of making a conductive channel-containing membrane, comprising:
(a) substantially removing solvents from a mixture comprising amphipathic lipids and at least one organic solvent, to obtain dried amphipathic lipids; and
(b) resuspending the dried amphipathic lipids in a second solution that comprises an aqueous solvent, an osmotic agent and a plurality of isolated viral DNA-packaging motor connector protein subunit polypeptides,
wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
wherein said plurality of isolated viral DNA packing motor connector protein subunit peptides are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when an electrical potential is applied across the membrane, and thereby making a conductive channel-containing membrane.

24. The method of either claim 22 or claim 23 wherein the amphipathic lipids comprise phospholipids.

25. The method of claim 24 wherein the phospholipids comprise one or more phospholipids selected from the group consisting of phosphatidylcholine, phosphatidylethanolamine, phosphatidylserine, phosphatidylinositol, phosphatidylglycerol, cardiolipin, 1,2-diphytanoyl-snglycerol-3-phosphochloline, and 1,2-dioleoyl-sn-glycero-3-phosphocholine.

26. The method of claim 22 or claim 23 wherein the organic solvent comprises at least one solvent selected from the group consisting of chloroform, methanol, ethanol, n-propanol, isopropanol, n-butanol, isobutanol, pyridine, and diisopropyl ether.

27. The method of either claim 22 or claim 23 wherein the osmotic agent comprises at least one agent that is selected from the group consisting of sucrose, glycerol, mannitol and dextran.

28. The method of either claim 22 or claim 23 wherein the lipid bilayer is present in a liposome.

29. The method of claim 28 wherein the liposome is selected from the group consisting of a multilamellar liposome and a unilamellar liposome.

30. The method of either claim 22 or claim 23 wherein the incorporated viral DNA-packaging motor connector protein is mobile in the membrane layer.

31. The method of either claim 22 or claim 23 wherein the viral DNA-packaging motor connector protein is capable of translocating double stranded DNA through the aperture when electrical potential is applied to the membrane.

32. The method of either claim 22 or claim 23 wherein conductance occurs in the conductive channel-containing membrane without voltage gating when electrical potential is applied.

33. The method of claim 32 wherein the applied electrical potential is selected from the group consisting of (i) a potential that is between −100 mV and 100 mV, (ii) a potential that is between −400 mV and 400 mV, (iii) a potential that is between −300 mV and 300 mV, (iv) a potential that is between −200 mV and 200 mV, (v) a potential that is between −150 mV and 150 mV, (vi) a potential that is between −75 mV and 75 mV, and (vii) a potential that is between −50 mV and 50 mV.

34. A method of concentrating nucleic acid molecules on one side of a conductive channel-containing membrane, comprising:
(a) making a conductive channel-containing membrane by a method comprising:
(i) substantially removing solvent from a mixture comprising amphipathic lipids and at least one solvent, to obtain dried amphipathic lipids; and
(ii) resuspending the dried amphipathic lipids in a second solution that comprises an aqueous solvent, an osmotic agent and a plurality of isolated viral DNA-packaging motor connector protein subunit polypeptides,
wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
wherein said plurality of isolated viral DNA packing motor connector protein subunit peptides are capable of self-assembly into a homododecameric viral DNA-packaging motor connector protein, to obtain a membrane that comprises a lipid bilayer in which is incorporated the viral DNA-packaging motor connector protein under conditions and for a time sufficient for said connector protein to form an aperture through which conductance can occur when a form of energy, including an electrical potential or biological energy ATP is applied across the membrane, and thereby making a conductive channel-containing membrane; and
(b) contacting the conductive channel-containing membrane of (a) with one or a plurality of nucleic acid molecules and with a form of energy, including an electrical potential or biological energy ATP that is applied across the membrane, under conditions and for a time sufficient for electrophoretic translocation of the nucleic acid through the aperture of the connector protein, and thereby concentrating nucleic acid molecules on one side of the conductive channel-containing membrane.

35. The method of claim 34 wherein nucleic acid translocation causes accumulation of the nucleic acid on one side of the membrane and against a nucleic acid concentration gradient.

36. The method of claim 34 further produces a liposome comprises a conductive channel-containing membrane and nucleic acid molecules that are concentrated on one side of the membrane.

37. The liposome of claim 36 which is a nanoparticle.

38. The liposome of claim 36 which is a bioreactor.

39. The method in claim 36 is further used to introduce one or plurality of liposomes into a cell.

40. An isolated protein, comprising a homododecamer of viral DNA-packaging motor connector protein polypeptide subunits, wherein each of said subunits comprises a fusion protein which comprises:
(a) an aperture domain that comprises an isolated viral connector protein polypeptide having an amino terminus and a carboxyl terminus;
(b) at least one flexibility domain that comprises a polypeptide of 4, 5, 6, 7, 8, 9, 10, 11, 12, 13, 14, 15, 16, 17 or 18 contiguous uncharged amino acids and that is fused to at least one of the amino terminus and the carboxyl terminus of (a); and
(c) at least one affinity/alignment domain.

41. An isolated protein, comprising a homododecamer of viral DNA-packaging motor connector protein polypeptide subunits, wherein each of said subunits comprises a fusion protein which comprises:
(a) an aperture domain that comprises an isolated viral connector protein polypeptide having an amino terminus and a carboxyl terminus;
(b) at least one flexibility domain that comprises a polypeptide of 4, 5, 6, 7, 8, 9, 10, 11, 12, 13 or 14 contiguous uncharged amino acids and that is fused to at least one of the amino terminus and the carboxyl terminus of (a); and
(c) at least one affinity/alignment domain that comprises a polypeptide of formula X1a-X1a-X2a-X1b-X1b-X1b-X3-X2b and that is fused to the flexibility domain, wherein each X1a is independently either any uncharged amino acid or no amino acid, each X1b is independently any uncharged amino acid, X2a is a positively charged amino acid selected from lysine, arginine and histidine, X3 is a negatively charged amino acid selected from glutamic acid and aspartic acid, and X2b is a positively charged amino acid selected from lysine, arginine and histidine.

42. An isolated protein, comprising a homododecamer of viral DNA-packaging motor connector protein polypeptide subunits, wherein each of said subunits comprises a fusion protein which comprises:
   (a) an aperture domain that comprises an isolated viral connector protein polypeptide having an amino terminus and a carboxyl terminus;
   (b) at least one flexibility domain that comprises a polypeptide of sequence Gly-Gly-Gly-Gly-Gly-Gly as set forth in SEQ ID NO:23 and that is fused to the carboxyl terminus of (a); and
   (c) at least one affinity/alignment domain that is fused to the flexibility domain.

43. The isolated protein of either claim 40 or claim 42 wherein the affinity/alignment domain comprises a polypeptide that is selected from the group consisting of:
   (i) a Strep-11 tag as set forth in SEQ ID NO:22 [WSHPQR-FEK];
   (ii) a polyhistidine polypeptide tag of 3, 4, 5, 6, 7, 8, 9, 10, 11 or 12 contiguous histidine residues;
   (iii) a polyarginine polypeptide of 3, 4, 5, 6, 7, 8, 9, 10, 11 or 12 contiguous arginine residues;
   (iv) an HIV Tat polypeptide of sequence YGRKKRRQRRR [SEQ ID NO:39]; and
   (v) a peptide tag of sequence DRATPY [SEQ ID NO:40].

44. An isolated protein, comprising a homododecamer of viral DNA-packaging motor connector protein polypeptide subunits, wherein each of said subunits comprises a polypeptide that is selected from the group consisting of:
   (i) C-His6-gp10/K234A as set forth in SEQ ID NO:41;
   (ii) C-His6-gp10/K234C as set forth in SEQ ID NO:42;
   (iii) C-His6-gp10/C76S/C265S/K234C as set forth in SEQ ID NO:43;
   (iv) Δ1-14/10-Strep-II as set forth in SEQ ID NO:44; and
   (v) Gp10/Δ285-309-Strep-II as set forth I SEQ ID NO:45.

45. The isolated protein of claim 40 wherein the aperture domain comprises a polypeptide that is selected from the group consisting of
   (i) all or a transmembrane aperture-forming portion of bacteriophage phi29 DNA-packaging motor connector protein polypeptide having the amino acid sequence set forth in SEQ ID NO:1 [Acc. No. ACE96033];
   (ii) all or a transmembrane aperture-forming portion of phage T4 DNA-packaging motor connector protein polypeptide having the amino acid sequence set forth in SEQ ID NO:7 [Acc. No. NP_049782];
   (iii) all or a transmembrane aperture-forming portion of phage lambda DNA packaging motor connector protein polypeptide having the amino acid sequence set forth in any one of SEQ ID NOS:8-11 [Acc. Nos. gi 549295, gi 6723246, gi 15837315, gi 16764273];
   (iv) all or a transmembrane aperture-forming portion of phage SPP1 DNA-packaging motor connector protein polypeptide having the amino acid sequence set forth in SEQ ID NO: 12 [Acc. No. P54309];
   (v) all or a transmembrane aperture-forming portion of phage P22 DNA packaging motor connector protein polypeptide having the amino acid sequence set forth in SEQ ID NO:13 [Acc. No. AAA72961];
   (vi) all or a transmembrane aperture-forming portion of phage P2 DNA-packaging motor connector protein polypeptide having the amino acid sequence set forth in SEQ ID NO:14 [Acc. No. NP_046757];
   (vii) all or a transmembrane aperture-forming portion of phage P3 DNA-packaging motor connector protein polypeptide;
   (viii) all or a transmembrane aperture-forming portion of phage T3 DNA-packaging motor connector protein polypeptide having the amino acid sequence set forth in SEQ ID NO:15 [Acc. No. CAA35152];
   (ix) all or a transmembrane aperture-forming portion of phage T5 DNA packaging motor connector protein polypeptide having the amino acid sequence set forth in SEQ ID NOS: 16-19 (Accession numbers AAX12078, YP_006980; AAS77191; AAU05287); and
   (x) all or a transmembrane aperture-forming portion of phage T7 DNA-packaging motor connector protein polypeptide having the amino acid sequence set forth in SEQ ID NO:20 [Acc. No. NP_041995].

46. The isolated protein of claim 40 wherein the aperture domain comprises a polypeptide that comprises all or a transmembrane aperture-forming portion of a double-stranded DN bacteriophage DNA-packaging motor connector protein.

47. The isolated protein of either claim 41 or claim 42 wherein the aperture domain comprises a polypeptide that is selected from the group consisting of
   (i) all or a transmembrane aperture-forming portion of bacteriophage phi29 DNA-packaging motor connector protein polypeptide having the amino acid sequence set forth in SEQ ID NO:1 [Acc. No. ACE96033];
   (ii) all or a transmembrane aperture-forming portion of phage T4 DNA-packaging motor connector protein polypeptide having the amino acid sequence set forth in SEQ ID NO:7 [Acc. No. NP_049782];
   (iii) all or a transmembrane aperture-forming portion of phage lambda DNA packaging motor connector protein polypeptide having the amino acid sequence set forth in any one of SEQ ID NOS:8-11 [Acc. Nos. gi 549295, gi 6723246, gi 15837315, gi 16764273];
   (iv) all or a transmembrane aperture-forming portion of phage SPP1 DNA-packaging motor connector protein polypeptide having the amino acid sequence set forth in SEQ ID NO: 12 [Acc. No. P54309];
   (v) all or a transmembrane aperture-forming portion of phage P22 DNA packaging motor connector protein polypeptide having the amino acid sequence set forth in SEQ ID NO: 13 [Acc. No. AAA72961];
   (vi) all or a transmembrane aperture-forming portion of phage P2 DNA-packaging motor connector protein polypeptide having the amino acid sequence set forth in SEQ ID NO:14 [Acc. No. NP_046757],
   (vii) all or a transmembrane aperture-forming portion of phage P3 DNA-packaging motor connector protein polypeptide,
   (viii) all or a transmembrane aperture-forming portion of phage T3 DNA-packaging motor connector protein polypeptide having the amino acid sequence set forth in SEQ ID NO: 15 [Acc. No. CAA35152],
   (ix) all or a transmembrane aperture-forming portion of phage T5 DNA packaging motor connector protein polypeptide having the amino acid sequence set forth in SEQ ID NOS:16-19 (Accession numbers AAX12078, YP_006980; AAS77191; AAU05287), and
   (x) all or a transmembrane aperture-forming portion of phage T7 DNA-packaging motor connector protein polypeptide having the amino acid sequence set forth in SEQ ID NO:20 [Acc. No. NP_041995].

48. The conductive channel-containing membrane of claim 40 wherein the aperture domain comprises a polypeptide that comprises all or a transmembrane aperture-forming portion of a
bacteriophage phi29 DNA-packaging motor connector protein polypeptide having the amino acid sequence set forth in SEQ ID NO:1 [Acc. No. ACE96033].

49. The isolated protein of any one of claim 40 or 42 wherein the viral connector protein
polypeptide comprises all or a transmembrane aperture-forming portion of bacteriophage phi29 DNA-packaging motor connector protein polypeptide having the amino acid sequence set forth in SEQ ID NO:1 [Acc. No. ACE96033].

50. The isolated protein of any one of claims 40-42 which is capable of (i) self-assembly into a dodecameric viral connector protein, and (ii) packaging viral dsDNA following incorporation into a viral procapsid.

51. The isolated protein according to any one of claims 40-42 comprises at least one detectable label.

52. The isolated protein of claim 51 wherein the detectable label is selected from the group consisting of a colorimetric indicator, a GCMS tag compound, a fluorescent indicator, a luminescent indicator, a phosphorescent indicator, a radiometric indicator, a dye, an enzyme, a substrate of an enzyme, an energy transfer molecule, a quantum dot, a metal particle and an affinity label.

53. The isolated protein of claim 52 wherein the affinity label is selected from the group consisting of avidin, streptavidin, biotin, an aptamer, an antibody, a lectin, an oligosaccharide, a nucleic acid, an enzyme, a metal ion-binding polypeptide, a Strep-II tag as set forth in SEQ ID NO:22 [WSHPQRFEK], a polyhistidine polypeptide tag of 3, 4, 5, 6, 7, 8, 9, 10, 11 or 12 contiguous histidine residues, a Strep-I tag, a FLAG® peptide tag, a Myc peptide tag, glutathione-S-transferase, maltose binding protein, S. aureus protein A, protein G, an HIV Tat polypeptide of sequence YGRKKRRQRRR [SEQ ID NO:39], a peptide having the amino acid sequence DRATPY [SEQ ID NO:40], glutaredoxin-2, and a phage-displayed peptide that specifically binds an affinity ligand.

54. The isolated protein of claim 53 wherein the antibody is selected from the group consisting of an intact immunoglobulin, a single-chain antibody, an scFv, a Fab and a (Fab)'2.

55. A method for detecting presence of an analyte molecule, comprising:
(a) contacting a test solution containing the analyte molecule with a conductive channel containing membrane which comprises a membrane layer and incorporated therein one or a plurality of isolated viral DNA-packaging motor connector proteins
wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
wherein said plurality of isolated viral DNA packing motor connector protein subunit peptides are capable of forming an aperture through which conductance can occur when an electrical potential is applied across the membrane, and that each comprise a homododecamer of viral DNA-packaging motor connector protein polypeptide subunits, wherein each of said subunits comprises
(1) an aperture domain that comprises an isolated viral connector protein polypeptide having an amino terminus and a carboxy terminus; and
(2) either or both of
1. at least one flexibility domain; and
2. at least one affinity/alignment domain, under conditions and for a time sufficient
for specific binding of the analyte molecule to the affinity/alignment domain; and
(b) determining, at one or a plurality of time points prior to the step of contacting and at one or a plurality of time points after the step of contacting, a conductance signal that results from the applied electrical potential, wherein an alteration in the conductance signal after the step of contacting relative to the conductance signal prior to the step of contacting indicates binding of the analyte molecule to the connector protein, and therefrom detecting presence of the analyte molecule.

56. The method of claim 55 wherein the alteration in the conductance signal indicates binding of the analyte molecule to the affinity/alignment domain.

57. A method for identifying an analyte, comprising
(a) contacting a test solution containing the analyte molecule with a conductive channel-containing membrane which comprises a membrane layer and incorporated therein one or a plurality of isolated viral DNA-packaging motor connector proteins,
wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
wherein said plurality of isolated viral DNA packing motor connector protein subunit peptides are capable of forming an aperture through which conductance can occur when an electrical potential is applied across the membrane, and that each comprise a homododecamer of viral DNA-packaging motor connector protein polypeptide subunits, wherein each of said subunits comprises
(1) an aperture domain that comprises a isolated viral connector protein polypeptide having an amino terminus and a carboxy terminus; and
(2) either or both of (i) at least one flexibility domain and (ii) at least one affinity/alignment domain, under conditions and for a time sufficient for specific binding of the analyte molecule to the affinity/alignment domain;
(b) determining, at one or a plurality of time points prior to the step of contacting and at one or a plurality of time points after the step of contacting, a conductance signal that results from the applied electrical potential and therefrom generating a conductance signal profile, wherein an alteration in the conductance signal after the step of contacting relative to the conductance signal prior to the step of contacting indicates binding of the analyte molecule to the connector protein; and
(c) comparing the conductance signal profile from (b) to a reference conductance signal profile for the analyte, and therefrom identifying the analyte molecule.

58. The method of claim 55 wherein the alteration in the conductance signal indicates binding of the analyte molecule to the affinity/alignment domain.

59. The method of either claim 55 or claim 57 wherein the step of contacting is repeated one or a plurality of times.

60. The method of claim 57 wherein the step of comparing comprises one or more of
(i) comparing conductance signal amplitude from the conductance signal profile of (b) to conductance signal amplitude in the reference conductance signal profile for the analyte, and (ii) comparing conductance signal duration from the conductance signal profile of (b) to conductance signal duration in the reference conductance signal profile for the analyte.

61. The method of either claim 55 or claim 57 wherein the applied electrical potential results in ionic migration along an electrochemical gradient in the aperture domain.

62. The method of either claim 55 or claim 57 wherein the analyte comprises a nucleic acid molecule.

63. The method of claim 57 wherein the analyte comprises a nucleic acid molecule and the step of comparing comprises identifying at least one nucleotide that is present in the nucleic acid molecule.

64. The method of claim 63 which comprises determining a nucleic acid sequence of the nucleic acid molecule.

65. The method of claim 63 which comprises identifying a single nucleotide polymorphism in the nucleic acid molecule.

66. The method of either claim 55 or claim 57 wherein voltage gating is not present.

67. An optical channel membrane, comprising,
   (a) a membrane layer, and
   (b) an isolated viral DNA packaging motor connector protein, said viral DNA packaging motor connector protein, wherein said isolated viral DNA-packaging motor connector protein comprising a homododecamer of viral DNA packaging motor connector protein polypeptide subunits, wherein each said subunit is labeled with at least one donor fluorophore and is incorporated into the membrane layer to form an aperture through which fluorescence excitation is captured when an analyte labeled with at least one acceptor fluorophore passes through the membrane layer.

68. An optical and conductive channel membrane, comprising,
   (a) a membrane layer; and
   (b) an isolated viral DNA packaging motor connector protein, said viral DNA packaging motor connector protein, wherein said isolated viral DNA-packaging motor connector protein comprising a homododecamer of viral DNA packaging motor connector protein polypeptide subunits, wherein each said subunit is labeled with at least one donor fluorophore and is incorporated into the membrane layer to form a aperture, through which fluorescence detection is coupled with the current detection when
      (i) an analyte labeled with at least one acceptor fluorophore passes through the membrane; and
      (ii) an electrical potential is applied across the membrane.

69. The optical channel membrane in claim 67 or 68, wherein the connector protein is labeled by Quantum Dots (QDs), and the analyte is labeled by the corresponding acceptor that is to be excited by said QDs.

70. A method of making an optical channel membrane, comprising:
   (a) preparing dried amphipathic lipids on a solid substrate by contacting a first solution comprising amphipathic lipids and an organic solvent with the solid substrate and substantially removing the solvent;
   (b) resuspending the dried amphipathic lipids in a second solution that comprises an aqueous solvent, an osmotic agent and a plurality of isolated viral DNA-packaging motor connector protein subunit polypeptides,
   wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
   wherein said plurality of isolated viral DNA packing motor connector protein subunit peptides are capable of self-assembly into a homododecameric viral DNA-packaging motor connector protein, to obtain a membrane that comprises a lipid bilayer in which is incorporated the viral DNA-packaging motor connector protein; and
   (c) attaching FRET donors to either N or C terminus of the connector subunits under conditions and for a time sufficient for said connector protein to form an aperture through which fluorescence excitation occurs and is being captured when an analyte labeled with a corresponding acceptor passes through the membrane, thereby making an optical detection membrane.

71. A method of making an optical and conductive channel membrane, comprising:
   (a) preparing dried amphipathic lipids on a solid substrate by contacting a first solution comprising amphipathic lipids and an organic solvent with the solid substrate and substantially removing the solvent;
   (b) resuspending the dried amphipathic lipids in a second solution that comprises an aqueous solvent, an osmotic agent and a plurality of isolated viral DNA-packaging motor connector protein subunit polypeptides,
   wherein said plurality of isolated viral DNA-packaging motor connector protein subunit each comprises an aperture domain that having an amino terminus and a carboxyl terminus, and either or both of terminus has a flexibility domain that is fused to at least one of said terminus, and at least one affinity/alignment domain,
   wherein said plurality of isolated viral DNA packing motor connector protein subunit peptides are capable of self-assembly into a homododecameric viral DNA-packaging motor connector protein, to obtain a membrane that comprises a lipid bilayer in which is incorporated the viral DNA-packaging motor connector protein; and
   (c) attaching FRET donors to either N or C terminus of the connector subunits under conditions and for a time sufficient for said connector protein to form an aperture through which
   (i) fluorescence excitation occurs and is being captured when an analyte labeled with a corresponding acceptor passes through the membrane; and
   (ii) conductance occurs when an electrical potential is applied across the membrane, thereby making an optical and conductive channel containing membrane.

72. The conductive channel of claim 1, wherein said aperture size ranges at about 3.6 nm diameter and cross section area about 10.2 square nm.

* * * * *

SEQUENCE LISTING

<160> NUMBER OF SEQ ID NOS: 49

<210> SEQ ID NO 1
<211> LENGTH: 309
<212> TYPE: PRT
<213> ORGANISM: Bacillus phage phi29

<400> SEQUENCE: 1

Met Ala Arg Lys Arg Ser Asn Thr Tyr Arg Ser Ile Asn Glu Ile Gln
 1               5                  10                  15

Arg Gln Lys Arg Asn Arg Trp Phe Ile His Tyr Leu Asn Tyr Leu Gln
            20                  25                  30

-continued

```
Ser Leu Ala Tyr Gln Leu Phe Glu Trp Glu Asn Leu Pro Thr Ile
         35                  40                  45
Asn Pro Ser Phe Leu Glu Lys Ser Ile His Gln Phe Gly Tyr Val Gly
 50                  55                  60
Phe Tyr Lys Asp Pro Val Ile Ser Tyr Ile Ala Cys Asn Gly Ala Leu
 65                  70                  75                  80
Ser Gly Gln Arg Asp Val Tyr Asn Gln Ala Thr Val Phe Arg Ala Ala
                 85                  90                  95
Ser Pro Val Tyr Gln Lys Glu Phe Lys Leu Tyr Asn Tyr Arg Asp Met
                100                 105                 110
Lys Glu Glu Asp Met Gly Val Val Ile Tyr Asn Asn Asp Met Ala Phe
            115                 120                 125
Pro Thr Thr Pro Thr Leu Glu Leu Phe Ala Ala Glu Leu Ala Glu Leu
130                 135                 140
Lys Glu Ile Ile Ser Val Asn Gln Asn Ala Gln Lys Thr Pro Val Leu
145                 150                 155                 160
Ile Arg Ala Asn Asp Asn Asn Gln Leu Ser Leu Lys Gln Val Tyr Asn
                165                 170                 175
Gln Tyr Glu Gly Asn Ala Pro Val Ile Phe Ala His Glu Ala Leu Asp
            180                 185                 190
Ser Asp Ser Ile Glu Val Phe Lys Thr Asp Ala Pro Tyr Val Val Asp
        195                 200                 205
Lys Leu Asn Ala Gln Lys Asn Ala Val Trp Asn Glu Met Met Thr Phe
210                 215                 220
Leu Gly Ile Lys Asn Ala Asn Leu Glu Lys Lys Glu Arg Met Val Thr
225                 230                 235                 240
Asp Glu Val Ser Ser Asn Asp Glu Gln Ile Glu Ser Ser Gly Thr Val
                245                 250                 255
Phe Leu Lys Ser Arg Glu Glu Ala Cys Glu Lys Ile Asn Glu Leu Tyr
            260                 265                 270
Gly Leu Asn Val Lys Val Lys Phe Arg Tyr Asp Ile Val Glu Gln Met
        275                 280                 285
Arg Arg Glu Leu Gln Gln Ile Glu Asn Val Ser Arg Gly Thr Ser Asp
290                 295                 300
Gly Glu Thr Asn Glu
305

<210> SEQ ID NO 2
<211> LENGTH: 249
<212> TYPE: PRT
<213> ORGANISM: Staphylococcus aureus phage P68

<400> SEQUENCE: 2

Met Ile Leu Gly Tyr Val Asn Asn Thr Tyr Phe Asn Gln Ala Pro Asn
  1               5                  10                  15
Phe Ser Ser Asn Phe Asn Phe Gln Phe Gln Lys Arg Leu Thr Lys Glu
             20                  25                  30
Asp Ile Tyr Phe Ile Val Pro Asp Tyr Leu Ile Pro Asp Asp Cys Leu
         35                  40                  45
Gln Ile His Lys Leu Tyr Asp Asn Cys Met Ser Gly Asn Phe Val Val
 50                  55                  60
Met Gln Asn Lys Pro Ile Gln Tyr Asn Ser Asp Ile Glu Ile Ile Glu
 65                  70                  75                  80
His Tyr Thr Asp Glu Leu Ala Glu Val Ala Leu Ser Arg Phe Ser Leu
                 85                  90                  95
```

```
Ile Met Gln Ala Lys Phe Ser Lys Ile Phe Lys Ser Glu Ile Asn Asp
            100                 105                 110

Glu Ser Ile Asn Gln Leu Val Ser Glu Ile Tyr Asn Gly Ala Pro Phe
        115                 120                 125

Val Lys Met Ser Pro Met Phe Asn Ala Asp Asp Ile Ile Asp Leu
130                 135                 140

Thr Ser Asn Ser Val Ile Pro Ala Leu Thr Glu Met Lys Arg Glu Tyr
145                 150                 155                 160

Gln Asn Lys Ile Ser Glu Leu Ser Asn Tyr Leu Gly Ile Asn Ser Leu
                165                 170                 175

Ala Val Asp Lys Glu Ser Gly Val Ser Asp Glu Ala Lys Ser Asn
            180                 185                 190

Arg Gly Phe Thr Thr Ser Asn Ser Asn Ile Tyr Leu Lys Gly Arg Glu
        195                 200                 205

Pro Ile Thr Phe Leu Ser Lys Arg Tyr Gly Leu Asp Ile Lys Pro Tyr
        210                 215                 220

Tyr Asp Asp Glu Thr Thr Ser Lys Ile Ser Met Val Asp Thr Leu Phe
225                 230                 235                 240

Lys Asp Glu Ser Ser Asp Ile Asn Gly
                245
```

<210> SEQ ID NO 3
<211> LENGTH: 317
<212> TYPE: PRT
<213> ORGANISM: Streptococcus phage C1

<400> SEQUENCE: 3

```
Met Gln Ile Thr Ser Gly Ile Lys Pro Ser Glu Met Asn Tyr Lys Met
1               5                   10                  15

Ser Thr Phe Thr Asp Asp Ile Ala Glu Arg Val Lys Leu His Lys Gln
            20                  25                  30

Asn Tyr Phe Asn Ile Ile Tyr Ser Arg Tyr Val Glu Phe Leu Pro Leu
        35                  40                  45

Leu Ile Ser Tyr Glu Asn Tyr Asp Leu Asp Ser Leu Leu Ile Glu Ser
50                  55                  60

Tyr Leu Arg Ala Gly Tyr Gly Val Ala Ile Gly Glu Thr Lys Thr Gly
65                  70                  75                  80

Lys Ile Asp Val Leu Gly Tyr Cys Ser Val Asn Thr Asn Tyr Leu Gln
                85                  90                  95

Pro Ile Lys Glu Pro Leu Gln Gly Lys Asp Ile Thr Phe Ile His Asn
            100                 105                 110

Asn Ile Leu Pro Lys Gly Lys Tyr Lys Glu Leu Thr Arg Tyr Ser Asp
        115                 120                 125

Gly Asn Phe Val Val Leu Arg Asn Lys Arg Ala Ser Phe Leu Cys Asp
130                 135                 140

Tyr Asn Ile Ile Thr His Tyr Val Met Glu Met Ser Glu Ile Ala Asn
145                 150                 155                 160

Ser Arg Tyr Ser Ile Ser Ile Gln Ala Lys Val Asn Thr Phe Ile Arg
                165                 170                 175

Asn Glu Gly Gly Ser Lys Asp Gly Gln Val Met Ala Asn Asn Leu Phe
            180                 185                 190

Asn Gly Val Pro Tyr Thr Ala Thr Thr Pro Lys Phe Asp Pro Glu Glu
        195                 200                 205

His Ile Leu Thr Phe Asn Asn Ala Ser Ala Val Ser Phe Leu Pro Glu
        210                 215                 220
```

```
Leu Lys Arg Glu Gln Gln Asn Lys Ile Ser Glu Leu Asn Ala Met Leu
225                 230                 235                 240

Gly Leu Asn Thr Leu Gly Val Asp Lys Glu Ser Gly Val Ser Glu Ile
            245                 250                 255

Glu Ala Gln Ser Asn Thr Ala Phe Lys Lys Ala Asn Glu Asn Ile Tyr
        260                 265                 270

Leu Gly Ile Arg Asn Glu Ala Leu Asn Leu Ile Asn Asn Lys Tyr Gly
    275                 280                 285

Leu Asn Ile His Ala Glu Tyr Arg Asp Asn Met Val Ala Glu Leu Ser
290                 295                 300

Ser Ile Glu Lys Leu Gln Ile Val Ser Glu Val Ala Gln
305                 310                 315

<210> SEQ ID NO 4
<211> LENGTH: 327
<212> TYPE: PRT
<213> ORGANISM: Staphylococcus phage 66

<400> SEQUENCE: 4

Met Asn Asn Asp Lys Arg Gly Leu Asn Val Glu Leu Ser Lys Glu Ile
1               5                   10                  15

Ser Lys Arg Val Val Glu His Arg Asn Arg Phe Lys Arg Leu Met Phe
            20                  25                  30

Asn Arg Tyr Leu Glu Phe Leu Pro Leu Leu Ile Asn Tyr Thr Asn Arg
        35                  40                  45

Asp Thr Val Gly Ile Asp Phe Ile Gln Leu Glu Ser Ala Leu Arg Gln
    50                  55                  60

Asn Ile Asn Val Val Gly Glu Ala Arg Asn Lys Gln Ile Met Ile
65                  70                  75                  80

Leu Gly Tyr Val Asn Asn Thr Tyr Phe Asn Gln Ala Pro Asn Phe Ser
                85                  90                  95

Ser Asn Phe Asn Phe Gln Phe Gln Lys Arg Leu Thr Lys Glu Asp Ile
            100                 105                 110

Tyr Phe Ile Val Pro Asp Tyr Leu Ile Pro Asp Asp Cys Leu Gln Ile
        115                 120                 125

His Lys Leu Tyr Asp Asn Cys Met Ser Gly Asn Phe Val Val Met Gln
    130                 135                 140

Asn Lys Pro Ile Gln Tyr Asn Ser Asp Ile Glu Ile Glu His Tyr
145                 150                 155                 160

Thr Asp Glu Leu Ala Glu Val Ala Leu Ser Arg Phe Ser Leu Ile Met
                165                 170                 175

Gln Ala Lys Phe Ser Lys Ile Phe Lys Ser Glu Ile Asn Asp Glu Ser
            180                 185                 190

Ile Asn Gln Leu Val Ser Glu Ile Tyr Asn Gly Ala Pro Phe Val Lys
        195                 200                 205

Met Ser Pro Met Phe Asn Ala Asp Asp Ile Ile Asp Leu Thr Ser
    210                 215                 220

Asn Ser Val Ile Pro Ala Leu Thr Glu Met Lys Arg Glu Tyr Gln Asn
225                 230                 235                 240

Lys Ile Ser Glu Leu Ser Asn Tyr Leu Gly Ile Asn Ser Leu Ala Val
                245                 250                 255

Asp Lys Glu Ser Gly Val Ser Asp Glu Glu Ala Lys Ser Asn Arg Gly
            260                 265                 270

Phe Thr Thr Ser Asn Ser Asn Ile Tyr Leu Lys Gly Arg Glu Pro Ile
        275                 280                 285
```

```
Thr Phe Leu Ser Lys Arg Tyr Gly Leu Asp Ile Lys Pro Tyr Tyr Asp
    290                 295                 300

Asp Glu Thr Thr Ser Lys Ile Ser Met Val Asp Thr Leu Phe Lys Asp
305                 310                 315                 320

Glu Ser Ser Asp Ile Asn Gly
                325

<210> SEQ ID NO 5
<211> LENGTH: 249
<212> TYPE: PRT
<213> ORGANISM: Staphylococcus phage 44AHJD

<400> SEQUENCE: 5

Met Ile Leu Gly Tyr Val Asn Asn Thr Tyr Phe Asn Gln Ala Pro Asn
1               5                   10                  15

Phe Ser Ser Asn Phe Asn Phe Gln Phe Gln Lys Arg Leu Thr Lys Glu
            20                  25                  30

Asp Ile Tyr Phe Ile Val Pro Asp Tyr Leu Ile Pro Asp Asp Cys Leu
        35                  40                  45

Gln Ile His Lys Leu Tyr Asp Asn Cys Met Ser Gly Asn Phe Val Val
    50                  55                  60

Met Gln Asn Lys Pro Ile Gln Tyr Asn Ser Asp Ile Glu Ile Ile Glu
65                  70                  75                  80

His Tyr Thr Asp Glu Leu Ala Glu Val Ala Leu Ser Arg Phe Ser Leu
                85                  90                  95

Ile Met Gln Ala Lys Phe Ser Lys Ile Phe Lys Ser Glu Ile Asn Asp
            100                 105                 110

Glu Ser Ile Asn Gln Leu Val Ser Glu Ile Tyr Asn Gly Ala Pro Phe
        115                 120                 125

Val Lys Met Ser Pro Met Phe Asn Ala Asp Asp Ile Ile Asp Leu
    130                 135                 140

Thr Ser Asn Ser Val Ile Pro Ala Leu Thr Glu Met Lys Arg Glu Tyr
145                 150                 155                 160

Gln Asn Lys Ile Ser Glu Leu Ser Asn Tyr Leu Gly Ile Asn Ser Leu
                165                 170                 175

Ala Val Asp Lys Glu Ser Gly Val Ser Asp Glu Glu Ala Lys Ser Asn
            180                 185                 190

Arg Gly Phe Thr Thr Ser Asn Ser Asn Ile Tyr Leu Lys Gly Arg Glu
        195                 200                 205

Pro Ile Thr Phe Leu Ser Lys Arg Tyr Gly Leu Asp Ile Lys Pro Tyr
    210                 215                 220

Tyr Asp Asp Glu Thr Thr Ser Lys Ile Ser Met Val Asp Thr Leu Phe
225                 230                 235                 240

Lys Asp Glu Ser Ser Asp Ile Asn Gly
                245

<210> SEQ ID NO 6
<211> LENGTH: 249
<212> TYPE: PRT
<213> ORGANISM: Staphylococcus phage SAP-2

<400> SEQUENCE: 6

Met Ile Leu Gly Tyr Val Asn Asn Thr Tyr Phe Asn Gln Ala Pro Asn
1               5                   10                  15

Phe Ser Ser Asn Phe Asn Phe Gln Phe Gln Lys Arg Leu Thr Lys Glu
            20                  25                  30
```

```
Asp Ile Tyr Phe Ile Val Pro Asp Tyr Leu Ile Pro Asp Glu Cys Leu
            35                  40                  45

Gln Ile His Lys Leu Tyr Asp Asn Cys Met Ser Gly Asn Phe Val Val
 50                  55                  60

Met Gln Asn Lys Pro Ile Gln Tyr Asn Ser Asp Ile Glu Ile Ile Glu
65                  70                  75                  80

His Tyr Thr Asp Glu Leu Ala Glu Val Val Leu Ser Arg Phe Ser Leu
                85                  90                  95

Ile Met Gln Ala Lys Phe Ser Lys Val Phe Lys Ser Glu Ile Asn Asp
            100                 105                 110

Glu Ser Ile Asn Gln Leu Val Ser Glu Ile Tyr Asn Gly Ala Pro Phe
        115                 120                 125

Val Lys Met Ser Pro Met Phe Asn Ala Glu Asp Ile Ile Asp Leu
130                 135                 140

Thr Ser Asn Ser Val Ile Pro Ala Leu Thr Glu Met Lys Arg Glu Tyr
145                 150                 155                 160

Gln Asn Lys Ile Ser Glu Leu Ser Asn Tyr Leu Gly Ile Asn Ser Leu
                165                 170                 175

Ala Val Asp Lys Glu Ser Gly Val Ser Asp Glu Glu Ala Lys Ser Asn
            180                 185                 190

Arg Gly Phe Thr Thr Ser Asn Ser Asn Ile Tyr Leu Lys Gly Arg Glu
        195                 200                 205

Pro Ile Thr Phe Leu Ser Lys Arg Tyr Gly Leu Asp Ile Lys Pro Tyr
    210                 215                 220

Tyr Asp Asp Glu Thr Thr Ser Lys Ile Ser Met Val Asp Thr Leu Leu
225                 230                 235                 240

Lys Asp Glu Ser Ser Asp Leu Asn Gly
                245

<210> SEQ ID NO 7
<211> LENGTH: 524
<212> TYPE: PRT
<213> ORGANISM: Enterobacteria phage T4

<400> SEQUENCE: 7

Met Lys Phe Asn Val Leu Ser Leu Phe Ala Pro Trp Ala Lys Met Asp
 1               5                  10                  15

Glu Arg Asn Phe Lys Asp Gln Glu Lys Glu Asp Leu Val Ser Ile Thr
                20                  25                  30

Ala Pro Lys Leu Asp Asp Gly Ala Arg Glu Phe Glu Val Ser Ser Asn
            35                  40                  45

Glu Ala Ala Ser Pro Tyr Asn Ala Ala Phe Gln Thr Ile Phe Gly Ser
 50                  55                  60

Tyr Glu Pro Gly Met Lys Thr Thr Arg Glu Leu Ile Asp Thr Tyr Arg
65                  70                  75                  80

Asn Leu Met Asn Asn Tyr Glu Val Asp Asn Ala Val Ser Glu Ile Val
                85                  90                  95

Ser Asp Ala Ile Val Tyr Glu Asp Asp Thr Glu Val Val Ala Leu Asn
            100                 105                 110

Leu Asp Lys Ser Lys Phe Ser Pro Lys Ile Lys Asn Met Met Leu Asp
        115                 120                 125

Glu Phe Ser Asp Val Leu Asn His Leu Ser Phe Gln Arg Lys Gly Ser
130                 135                 140

Asp His Phe Arg Arg Trp Tyr Val Asp Ser Arg Ile Phe Phe His Lys
145                 150                 155                 160
```

```
Ile Ile Asp Pro Lys Arg Pro Lys Glu Gly Ile Lys Glu Leu Arg Arg
                165                 170                 175

Leu Asp Pro Arg Gln Val Gln Tyr Val Arg Glu Ile Ile Thr Glu Thr
            180                 185                 190

Glu Ala Gly Thr Lys Ile Val Lys Gly Tyr Lys Glu Tyr Phe Ile Tyr
        195                 200                 205

Asp Thr Ala His Glu Ser Tyr Ala Cys Asp Gly Arg Met Tyr Glu Ala
    210                 215                 220

Gly Thr Lys Ile Lys Ile Pro Lys Ala Ala Val Val Tyr Ala His Ser
225                 230                 235                 240

Gly Leu Val Asp Cys Cys Gly Lys Asn Ile Ile Gly Tyr Leu His Arg
                245                 250                 255

Ala Val Lys Pro Ala Asn Gln Leu Lys Leu Leu Glu Asp Ala Val Val
            260                 265                 270

Ile Tyr Arg Ile Thr Arg Ala Pro Asp Arg Arg Val Trp Tyr Val Asp
        275                 280                 285

Thr Gly Asn Met Pro Ala Arg Lys Ala Ala Glu His Met Gln His Val
    290                 295                 300

Met Asn Thr Met Lys Asn Arg Val Val Tyr Asp Ala Ser Thr Gly Lys
305                 310                 315                 320

Ile Lys Asn Gln Gln His Asn Met Ser Met Thr Glu Asp Tyr Trp Leu
                325                 330                 335

Gln Arg Arg Asp Gly Lys Ala Val Thr Glu Val Asp Thr Leu Pro Gly
            340                 345                 350

Ala Asp Asn Thr Gly Asn Met Glu Asp Ile Arg Trp Phe Arg Gln Ala
        355                 360                 365

Leu Tyr Met Ala Leu Arg Val Pro Leu Ser Arg Ile Pro Gln Asp Gln
    370                 375                 380

Gln Gly Gly Val Met Phe Asp Ser Gly Thr Ser Ile Thr Arg Asp Glu
385                 390                 395                 400

Leu Thr Phe Ala Lys Phe Ile Arg Glu Leu Gln His Lys Phe Glu Glu
                405                 410                 415

Val Phe Leu Asp Pro Leu Lys Thr Asn Leu Leu Lys Gly Ile Ile
            420                 425                 430

Thr Glu Asp Glu Trp Asn Asp Glu Ile Asn Ile Lys Ile Glu Phe
        435                 440                 445

His Arg Asp Ser Tyr Phe Ala Glu Leu Lys Glu Ala Glu Ile Leu Glu
    450                 455                 460

Arg Arg Ile Asn Met Leu Thr Met Ala Glu Pro Phe Ile Gly Lys Tyr
465                 470                 475                 480

Ile Ser His Arg Thr Ala Met Lys Asp Ile Leu Gln Met Thr Asp Glu
                485                 490                 495

Glu Ile Glu Gln Glu Ala Lys Gln Ile Glu Glu Ser Lys Glu Ala
            500                 505                 510

Arg Phe Gln Asp Pro Asp Gln Glu Asp Phe
            515                 520

<210> SEQ ID NO 8
<211> LENGTH: 530
<212> TYPE: PRT
<213> ORGANISM: Enterobacteria phage P21
```

-continued

<400> SEQUENCE: 8

Met Lys Arg Thr Pro Val Leu Ile Asp Val Asn Gly Val Pro Leu Arg
1               5                   10                  15

Glu Ser Leu Ser Tyr Asn Gly Gly Ala Gly Phe Gly Gly Gln Met
            20                  25                  30

Ala Glu Trp Leu Pro Pro Ala Gln Ser Ala Asp Ala Ala Leu Leu Pro
        35                  40                  45

Ala Leu Arg Leu Gly Asn Ala Arg Ala Asp Asp Leu Val Arg Asn Asn
    50                  55                  60

Gly Ile Ala Ala Asn Ala Val Ala Leu His Lys Asp His Ile Val Gly
65                  70                  75                  80

His Met Phe Leu Ile Ser Tyr Arg Pro Asn Trp Arg Trp Leu Gly Met
                85                  90                  95

Arg Glu Thr Ala Ala Lys Ser Phe Val Asp Glu Val Glu Ala Ala Trp
            100                 105                 110

Ser Glu Tyr Ala Glu Gly Met Phe Gly Glu Ile Asp Val Glu Gly Lys
        115                 120                 125

Arg Thr Phe Thr Glu Phe Ile Arg Glu Gly Val Gly Val His Ala Phe
    130                 135                 140

Asn Gly Glu Ile Phe Val Gln Pro Val Trp Asp Thr Glu Thr Thr Gln
145                 150                 155                 160

Leu Phe Arg Thr Arg Phe Lys Ala Val Ser Pro Lys Arg Val Asp Thr
                165                 170                 175

Pro Gly His Gly Met Gly Asn Arg Phe Leu Arg Ala Gly Val Glu Val
            180                 185                 190

Asp Arg Tyr Gly Arg Ala Val Ala Tyr His Ile Cys Glu Asp Asp Phe
        195                 200                 205

Pro Phe Ser Gly Ser Gly Arg Trp Glu Arg Ile Pro Arg Glu Leu Pro
    210                 215                 220

Thr Gly Arg Pro Ala Met Leu His Ile Phe Glu Pro Val Glu Asp Gly
225                 230                 235                 240

Gln Thr Arg Gly Ala Asn Gln Phe Tyr Ser Val Met Glu Arg Leu Lys
                245                 250                 255

Met Leu Asp Ser Leu Gln Ala Thr Gln Leu Gln Ser Ala Ile Val Lys
            260                 265                 270

Ala Met Tyr Ala Ala Thr Ile Glu Ser Glu Leu Asp Thr Glu Lys Ala
        275                 280                 285

Phe Glu Tyr Ile Ala Gly Ala Pro Gln Glu Gln Lys Asp Asn Pro Leu
    290                 295                 300

Ile Asn Ile Leu Glu Lys Phe Ser Ser Trp Tyr Asp Thr Asn Asn Val
305                 310                 315                 320

Thr Leu Gly Gly Val Lys Ile Pro His Leu Phe Pro Gly Asp Asp Leu
                325                 330                 335

Lys Leu Gln Thr Ala Gln Asp Ser Asp Asn Gly Phe Ser Ala Leu Glu
            340                 345                 350

Gln Ala Leu Leu Arg Tyr Ile Ala Ala Gly Leu Gly Val Ser Tyr Glu
        355                 360                 365

Gln Leu Ser Arg Asp Tyr Ser Lys Val Ser Tyr Ser Ser Ala Arg Ala
    370                 375                 380

Ser Ala Asn Glu Ser Trp Arg Tyr Phe Met Gly Arg Arg Lys Phe Ile
385                 390                 395                 400

Ala Ala Arg Leu Ala Thr Gln Met Phe Ser Cys Trp Leu Glu Glu Ala
                405                 410                 415

```
Leu Leu Arg Gly Ile Ile Arg Pro Arg Ala Arg Phe Asp Phe Tyr
                420                 425                 430

Gln Ala Arg Ser Ala Trp Ser Arg Ala Glu Trp Ile Gly Ala Gly Arg
            435                 440                 445

Met Ala Ile Asp Gly Leu Lys Glu Val Gln Glu Ser Val Met Arg Ile
    450                 455                 460

Glu Ala Gly Leu Ser Thr Tyr Glu Lys Gly Leu Ala Leu Met Gly Glu
465                 470                 475                 480

Asp Tyr Gln Asp Ile Phe Arg Gln Val Arg Glu Ser Ala Glu Arg
                485                 490                 495

Gln Lys Ala Gly Leu Ser Arg Pro Val Trp Ile Glu Gln Ala Tyr Gln
            500                 505                 510

Gln Gln Ile Ala Glu Ser Arg Arg Pro Glu Glu Thr Thr Pro Arg
            515                 520                 525

Glu Thr
    530

<210> SEQ ID NO 9
<211> LENGTH: 472
<212> TYPE: PRT
<213> ORGANISM: Wolbachia phage WO

<400> SEQUENCE: 9

Met Leu Leu Lys Ser Phe Lys Gln Leu Phe Ser Lys Pro Lys Ile Lys
1               5                   10                  15

Ser Ser Ala Trp Asp Ala Ala Gly Ser Gly Arg Arg Phe Phe His Phe
            20                  25                  30

Gln Pro Glu Leu Gly Ser Ile Asn Asn Leu Leu Ser Gln Ser Leu Glu
        35                  40                  45

Thr Leu Arg Ser Arg Ser Arg Asp Met Val Arg Lys Asn Pro Tyr Ala
    50                  55                  60

Ala Asn Ile Ile Asp Thr Ile Val Ser Asn Ser Ile Gly Thr Gly Ile
65                  70                  75                  80

Lys Pro Gln Ser Lys Ala Arg Asp Gly Glu Phe Arg Lys Lys Val Gln
                85                  90                  95

Glu Leu Trp Leu Lys Trp Thr Asp Glu Ala Asp Ser Cys Gly Ile Ser
            100                 105                 110

Asp Phe Tyr Gly Leu Gln Ala Leu Val Cys Arg Ser Met Ile Glu Gly
        115                 120                 125

Gly Glu Cys Phe Val Arg Leu Arg Thr Arg Lys Leu Glu Asp Arg Phe
    130                 135                 140

Ser Val Pro Leu Gln Leu Gln Val Leu Glu Ser Glu His Leu Asp Asn
145                 150                 155                 160

Lys Thr Asn Gln Thr Leu Gly Asn Gly Asn Val Ile Arg Asn Gly Ile
                165                 170                 175

Glu Phe Asn Arg Leu Gly Gln Arg Glu Ala Tyr Tyr Leu Phe Arg Glu
            180                 185                 190

His Pro Gly Glu Gly Ser Phe Gly Glu Ser Val Arg Val Pro Ala Asn
        195                 200                 205

Asp Val Leu His Ile Tyr Lys Pro Leu Arg Pro Gly Gln Ile Arg Gly
    210                 215                 220

Glu Pro Trp Leu Ser Ser Ile Leu Leu Lys Leu Tyr Glu Leu Asp Gln
225                 230                 235                 240

Tyr Asp Asp Ala Glu Leu Val Arg Lys Lys Thr Ala Ala Met Phe Ala
                245                 250                 255
```

```
Gly Phe Ile Thr Arg Leu Asp Pro Glu Ala Asn Ile Met Gly Glu Gly
            260                 265                 270

Glu Ala Ser Glu Gln Gly Val Ala Leu Ser Gly Leu Glu Pro Gly Thr
        275                 280                 285

Met Gln Leu Leu Asp Pro Gly Glu Asp Ile Lys Phe Ser Glu Pro Ser
    290                 295                 300

Asp Val Gly Gly Ser Tyr Glu Ala Phe Ile Arg Gln Gln Leu Arg Ala
305                 310                 315                 320

Ile Ala Ile Gly Thr Gly Ile Thr Tyr Glu Gln Leu Thr Gly Asp Leu
                325                 330                 335

Thr Gly Val Asn Tyr Ser Ser Ile Arg Ala Gly Leu Ile Glu Phe Arg
            340                 345                 350

Arg Arg Cys Ala Met Leu Gln His Asn Ile Met Val Phe Gln Phe Cys
        355                 360                 365

Arg Pro Val Trp Ser Arg Trp Leu Glu Leu Ala Val Leu Cys Gly Glu
    370                 375                 380

Leu Ser Ile Asp Glu Lys Val Val Lys Ala Ala Lys Glu Glu Val Lys
385                 390                 395                 400

Trp Ile Pro Gln Gly Phe Asp Trp Val Asp Pro Leu Lys Asp Gln Gln
                405                 410                 415

Ala Gln Gln Met Ala Val Arg Asn Gly Phe Lys Ser Arg Ser Glu Val
            420                 425                 430

Val Ser Glu Met Gly Tyr Asp Val Glu Glu Ile Asp Gln Glu Ile Ala
        435                 440                 445

Glu Asp Gln Lys Arg Ala Asn Ser Leu Asn Leu Ile Phe Asp Ser Asp
450                 455                 460

Val Gly Gly Asn Asn Val Ser Lys
465                 470

<210> SEQ ID NO 10
<211> LENGTH: 532
<212> TYPE: PRT
<213> ORGANISM: Xylella fastidiosa 9a5c

<400> SEQUENCE: 10

Met Asn Leu Trp Thr Trp Trp Thr Gln Arg Thr Ala His Pro Asp His
1               5                   10                  15

Pro Thr Pro Asp Thr Ala Thr Pro Gln Pro Asn His Pro Pro Arg Arg
            20                  25                  30

Trp Tyr Gln Arg Leu Leu Pro Leu Gly Gly Met Phe Lys Ala Gly Gln
        35                  40                  45

Val Asp Ala Asn Asp Leu Trp Ser Ser Ile Pro Val Ser Pro Asp Glu
50                  55                  60

Tyr Ile Thr Gln Arg Leu Pro Ile Leu Val Ala Arg Met Arg Glu Gln
65                  70                  75                  80

Trp Ser Asn Asn Asp His Val Lys Arg Tyr Ile Asp Leu Cys Arg Arg
                85                  90                  95

Asn Ile Val Gly Pro Arg Gly Ile Val Met Gln Ala Gln Ser Arg Lys
            100                 105                 110

Ser Arg Ser Gly Ala Leu Asp Thr Thr Ile Asn Asp Ala Ile Glu Thr
        115                 120                 125

Trp Trp Gln Asp Trp Gly Arg Lys Gly His Cys Asp Val Thr Gly Lys
    130                 135                 140

Leu Ser Trp Arg Glu Ile Gln Thr Leu Cys Val Glu Thr Cys Ala Arg
145                 150                 155                 160
```

-continued

```
Asp Gly Glu Cys Ile Ala Arg Lys Ile Tyr Gly Thr His Ala Gly Pro
            165                 170                 175
His Gly Phe Cys Leu Gln Leu Ile Asp Pro Leu Arg Leu Pro Val Arg
        180                 185                 190
Tyr Gln Met Leu Lys Thr Asp Gln Thr Gly Gly Phe Val Arg Gln Gly
            195                 200                 205
Ile Glu Phe Asn Arg Phe Gly Lys Pro Leu Ala Tyr His Phe Ser Ser
        210                 215                 220
Ile Asp Glu Arg Asp Thr Tyr Tyr Ser Ile Asn Gly Arg Gly Tyr
225                 230                 235                 240
Val Arg Val Pro Ala Glu Val Ile His Ile Phe Lys Pro Val Met
                245                 250                 255
Val Gly Gln Arg Arg Gly Leu Pro Trp Ala Ala Thr Ser Leu Leu Arg
        260                 265                 270
Leu His His Leu Gln Gly Phe Glu Ala Ala Val Gln Asn Ala Arg
            275                 280                 285
Ala Ala Ala Ser Lys Met Gly Phe Ile Lys Tyr Gln Glu Gly Phe Gly
        290                 295                 300
Ala Arg Ala Asp Glu His Glu Asn Val Ala Gln Thr Ile Gln Met Asn
305                 310                 315                 320
Ala Gly Pro Leu Ser Phe His Glu Leu Pro Ala Gly Gly Asp Ile Gln
                325                 330                 335
Asp Trp Asn Pro Gln Tyr Pro Ser Gly Glu Phe Gly Leu Phe Thr Lys
            340                 345                 350
Ala Ala Lys Gln Ser Leu Ala Ala Gly Met Asp Val Ser Tyr His Ala
        355                 360                 365
Leu Ser Gly Asp Leu Ala Asp Val Asn Tyr Ser Ser Ile Arg Gln Gly
            370                 375                 380
Thr Leu Asp Glu Arg Glu Arg Trp Lys Glu Asp Gln Gln Phe Phe Ile
385                 390                 395                 400
Glu Ser Leu His Thr Pro Val Phe Glu Ala Ala Leu Lys Val Ala Leu
                405                 410                 415
Leu Ser Gly Gln Ile Arg Val His Gly Lys Pro Leu Pro Ala Glu His
            420                 425                 430
Tyr Asp Arg Tyr Arg Arg Val Ser Trp Gln Gly Arg Trp Ala Trp
        435                 440                 445
Val Asp Pro Arg Ala Asp Val Glu Ser Ala Leu Thr Cys Ile Arg Gly
        450                 455                 460
Gly Leu Thr Ser Thr Ser Gln Val Ile Leu Glu Gln Gly Arg Asp Pro
465                 470                 475                 480
Gln Asp Val Phe Arg Glu Ile Ala Gln Asp Leu Lys Glu Met Gln Ala
                485                 490                 495
Ser Gly Ile Pro Asn Asp Tyr Leu Lys Tyr Leu Leu Tyr Gly Ala Asp
            500                 505                 510
Leu Thr Val Ala Asn Ala Thr Pro Thr Glu Lys Glu Pro Thr Pro His
        515                 520                 525
Glu His Ser His
    530
```

<210> SEQ ID NO 11
<211> LENGTH: 511
<212> TYPE: PRT
<213> ORGANISM: Salmonella phage Fels-1

<400> SEQUENCE: 11

```
Met Asn Phe Leu Asp Lys Ala Ile Gly Ala Leu Ala Pro Gly Trp Gly
  1               5                  10                  15
Ala Ser Arg Leu Arg Ser Arg Met Ala Ile Arg Ala Tyr Glu Ala Ile
             20                  25                  30
Thr Pro Thr Arg Thr His Arg Val Lys Arg Glu Asn Arg Ser Gly Asp
         35                  40                  45
Gln Leu Ile Gln Leu Ala Gly Lys Ser Leu Arg Glu Gln Ala Arg Trp
     50                  55                  60
Phe Asp Asn Asn His Asp Leu Val Ile Gly Ala Leu Asp Lys Met Glu
 65                  70                  75                  80
Glu Arg Ile Ile Gly Ala Lys Gly Ile Ile Val Glu Pro Gln Pro Leu
                 85                  90                  95
Thr Gly Thr Gly Thr Leu Asn Ser Val Leu Ala Glu Lys Ile Arg Arg
            100                 105                 110
Cys Trp Ala Glu Trp Ser Val Ser Pro Glu Val Thr Gly Gln Tyr Thr
        115                 120                 125
Arg Pro Val Leu Glu Arg Leu Met Leu Arg Thr Trp Leu Arg Asp Gly
    130                 135                 140
Glu Val Phe Thr Gln Val Leu Thr Gly Lys Ile Ser Gly Leu Ser Pro
145                 150                 155                 160
Val Ala Gly Val Pro Phe Trp Leu Glu Ala Leu Glu Pro Asp Tyr Ile
                165                 170                 175
Pro Leu Glu Arg Thr Asp Asn Asn Ser Asn Leu Val Gln Gly Ile Tyr
            180                 185                 190
Phe Asn Glu Trp Arg Arg Pro Val Lys Tyr Leu Val Cys Gln Ser Trp
        195                 200                 205
Pro Gly Ala Gly Ala Ala Val Ala Val Lys Glu Val Thr Ala Glu
    210                 215                 220
Asn Met Leu His Leu Arg Phe Thr Arg Arg Leu Asn Gln Ala Arg Gly
225                 230                 235                 240
Ala Ser Leu Leu Ala Pro Val Ile Ile Arg Leu Met Asp Leu Lys Glu
                245                 250                 255
Tyr Glu Asp Ser Glu Arg Ile Ala Ala Arg Ile Ala Ala Ser Leu Gly
            260                 265                 270
Met Phe Ile Lys Lys Gln Asp Val Gly Thr Asp Gly Tyr Val Ala Pro
        275                 280                 285
Glu Lys Arg Lys Glu Thr Gln Ile Gln Pro Gly Met Leu Phe Asp Gly
    290                 295                 300
Leu Asn Pro Gly Glu Asp Ile Gly Met Ile Lys Ser Asp Arg Pro Asn
305                 310                 315                 320
Ala Gly Leu Glu Ser Phe Arg Met Gly Gln Leu Arg Ala Val Ala Ala
                325                 330                 335
Gly Leu Arg Gly Ser Phe Ser Ser Ile Ala Arg Asn Tyr Asp Gly Thr
            340                 345                 350
Tyr Ser Ala Gln Arg Gln Glu Leu Val Glu Ala Gln Glu Gly Tyr Ser
        355                 360                 365
Ile Leu Gln Asp Ser Phe Ile Ala Ala Phe Thr Arg Pro Leu Tyr Arg
    370                 375                 380
Arg Trp Leu Ala Ala Ala Val Ala Ser Gly Ala Ile Glu Val Pro Ala
385                 390                 395                 400
Gly Thr Asp Met Ser Ser Leu Phe Asn Ala Val Tyr Ser Gly Pro Val
                405                 410                 415
```

Met Pro Trp Ile Asp Pro Leu Lys Glu Ala Asn Ala Trp Arg Val Leu
            420             425                 430

Ile Arg Gly Gly Ala Ala Thr Glu Gly Asp Trp Val Arg Ala Arg Gly
        435                 440                 445

Gly Ala Pro Ala Asp Val Lys Arg Arg Arg Lys Ala Glu Thr Asp Glu
    450                 455                 460

Asn Arg Lys Leu Gly Leu Val Phe Asp Thr Asp Pro Ala His Glu Thr
465                 470                 475                 480

Gly Glu Gln Ser Asp Val Lys Glu Glu Lys Lys Asp Pro Glu Lys Ser
                485                 490                 495

Thr Gln Gly Asp Gly Ser Arg Ala Arg Glu Glu Arg Lys Arg Arg
            500                 505                 510

<210> SEQ ID NO 12
<211> LENGTH: 503
<212> TYPE: PRT
<213> ORGANISM: Bacillus phage SPP1

<400> SEQUENCE: 12

Met Ala Asp Ile Tyr Pro Leu Gly Lys Thr His Thr Glu Glu Leu Asn
1               5                   10                  15

Glu Ile Ile Val Glu Ser Ala Lys Glu Ile Ala Glu Pro Asp Thr Thr
            20                  25                  30

Met Ile Gln Lys Leu Ile Asp Glu His Asn Pro Glu Pro Leu Leu Lys
        35                  40                  45

Gly Val Arg Tyr Tyr Met Cys Glu Asn Asp Ile Glu Lys Lys Arg Arg
    50                  55                  60

Thr Tyr Tyr Asp Ala Ala Gly Gln Gln Leu Val Asp Asp Thr Lys Thr
65                  70                  75                  80

Asn Asn Arg Thr Ser His Ala Trp His Lys Leu Phe Val Asp Gln Lys
                85                  90                  95

Thr Gln Tyr Leu Val Gly Glu Pro Val Thr Phe Thr Ser Asp Asn Lys
            100                 105                 110

Thr Leu Leu Glu Tyr Val Asn Glu Leu Ala Asp Asp Phe Asp Asp
        115                 120                 125

Ile Leu Asn Glu Thr Val Lys Asn Met Ser Asn Lys Gly Ile Glu Tyr
    130                 135                 140

Trp His Pro Phe Val Asp Glu Glu Gly Glu Phe Asp Tyr Val Ile Phe
145                 150                 155                 160

Pro Ala Glu Glu Met Ile Val Val Tyr Lys Asp Asn Thr Arg Arg Asp
                165                 170                 175

Ile Leu Phe Ala Leu Arg Tyr Tyr Ser Tyr Lys Gly Ile Met Gly Glu
            180                 185                 190

Glu Thr Gln Lys Ala Glu Leu Tyr Thr Asp Thr His Val Tyr Tyr Tyr
        195                 200                 205

Glu Lys Ile Asp Gly Val Tyr Gln Met Asp Tyr Ser Tyr Gly Glu Asn
    210                 215                 220

Asn Pro Arg Pro His Met Thr Lys Gly Gly Gln Ala Ile Gly Trp Gly
225                 230                 235                 240

Arg Val Pro Ile Ile Pro Phe Lys Asn Asn Glu Glu Met Val Ser Asp
                245                 250                 255

Leu Lys Phe Tyr Lys Asp Leu Ile Asp Asn Tyr Asp Ser Ile Thr Ser
            260                 265                 270

Ser Thr Met Asp Ser Phe Ser Asp Phe Gln Gln Ile Val Tyr Val Leu
        275                 280                 285

```
Lys Asn Tyr Asp Gly Glu Asn Pro Lys Glu Phe Thr Ala Asn Leu Arg
    290                 295                 300

Tyr His Ser Val Ile Lys Val Ser Gly Asp Gly Val Asp Thr Leu
305                 310                 315                 320

Arg Ala Glu Ile Pro Val Asp Ser Ala Ala Lys Glu Leu Glu Arg Ile
                    325                 330                 335

Gln Asp Glu Leu Tyr Lys Ser Ala Gln Ala Val Asp Asn Ser Pro Glu
                340                 345                 350

Thr Ile Gly Gly Gly Ala Thr Gly Pro Ala Leu Glu Asn Leu Tyr Ala
            355                 360                 365

Leu Leu Asp Leu Lys Ala Asn Met Ala Glu Arg Lys Ile Arg Ala Gly
370                 375                 380

Leu Arg Leu Phe Phe Trp Phe Phe Ala Glu Tyr Leu Arg Asn Thr Gly
385                 390                 395                 400

Lys Gly Asp Phe Asn Pro Asp Lys Glu Leu Thr Met Thr Phe Thr Arg
                    405                 410                 415

Thr Arg Ile Gln Asn Asp Ser Glu Ile Val Gln Ser Leu Val Gln Gly
                420                 425                 430

Val Thr Gly Gly Ile Met Ser Lys Glu Thr Ala Val Ala Arg Asn Pro
            435                 440                 445

Phe Val Gln Asp Pro Glu Glu Glu Leu Ala Arg Ile Glu Glu Glu Met
450                 455                 460

Asn Gln Tyr Ala Glu Met Gln Gly Asn Leu Leu Asp Asp Glu Gly Gly
465                 470                 475                 480

Asp Asp Asp Leu Glu Glu Asp Pro Asn Ala Gly Ala Ala Glu Ser
                    485                 490                 495

Gly Gly Ala Gly Gln Val Ser
            500
```

<210> SEQ ID NO 13
<211> LENGTH: 725
<212> TYPE: PRT
<213> ORGANISM: Enterobacteria phage P22

<400> SEQUENCE: 13

```
Met Ala Asp Asn Glu Asn Arg Leu Glu Ser Ile Leu Ser Arg Phe Asp
1               5                   10                  15

Ala Asp Trp Thr Ala Ser Asp Glu Ala Arg Arg Glu Ala Lys Asn Asp
                20                  25                  30

Leu Phe Phe Ser Arg Val Ser Gln Trp Asp Asp Trp Leu Ser Gln Tyr
            35                  40                  45

Thr Thr Leu Gln Tyr Arg Gly Gln Phe Asp Val Val Arg Pro Val Val
50                  55                  60

Arg Lys Leu Val Ser Glu Met Arg Gln Asn Pro Ile Asp Val Leu Tyr
65                  70                  75                  80

Arg Pro Lys Asp Gly Ala Arg Pro Asp Ala Ala Asp Val Leu Met Gly
                    85                  90                  95

Met Tyr Arg Thr Asp Met Arg His Asn Thr Ala Lys Ile Ala Val Asn
                100                 105                 110

Ile Ala Val Arg Glu Gln Ile Glu Ala Gly Val Gly Ala Trp Arg Leu
            115                 120                 125

Val Thr Asp Tyr Glu Asp Gln Ser Pro Thr Ser Asn Asn Gln Val Ile
130                 135                 140

Arg Arg Glu Pro Ile His Ser Ala Cys Ser His Val Ile Trp Asp Ser
145                 150                 155                 160
```

-continued

```
Asn Ser Lys Leu Met Asp Lys Ser Asp Ala Arg His Cys Thr Val Ile
            165                 170                 175
His Ser Met Ser Gln Asn Gly Trp Glu Asp Phe Ala Glu Lys Tyr Asp
        180                 185                 190
Leu Asp Ala Asp Asp Ile Pro Ser Phe Gln Asn Pro Asn Asp Trp Val
            195                 200                 205
Phe Pro Trp Leu Thr Gln Asp Thr Ile Gln Ile Ala Glu Phe Tyr Glu
210                 215                 220
Val Val Glu Lys Lys Glu Thr Ala Phe Ile Tyr Gln Asp Pro Val Thr
225                 230                 235                 240
Gly Glu Pro Val Ser Tyr Phe Lys Arg Asp Ile Lys Asp Val Ile Asp
            245                 250                 255
Asp Leu Ala Asp Ser Gly Phe Ile Lys Ile Ala Glu Arg Gln Ile Lys
        260                 265                 270
Arg Arg Arg Val Tyr Lys Ser Ile Ile Thr Cys Thr Ala Val Leu Lys
            275                 280                 285
Asp Lys Gln Leu Ile Ala Gly Glu His Ile Pro Ile Val Pro Val Phe
        290                 295                 300
Gly Glu Trp Gly Phe Val Glu Asp Lys Glu Val Tyr Glu Gly Val Val
305                 310                 315                 320
Arg Leu Thr Lys Asp Gly Gln Arg Leu Arg Asn Met Ile Met Ser Phe
            325                 330                 335
Asn Ala Asp Ile Val Ala Arg Thr Pro Lys Lys Pro Phe Phe Trp
            340                 345                 350
Pro Glu Gln Ile Ala Gly Phe Glu His Met Tyr Asp Gly Asn Asp Asp
        355                 360                 365
Tyr Pro Tyr Tyr Leu Leu Asn Arg Thr Asp Glu Asn Ser Gly Asp Leu
        370                 375                 380
Pro Thr Gln Pro Leu Ala Tyr Tyr Glu Asn Pro Glu Val Pro Gln Ala
385                 390                 395                 400
Asn Ala Tyr Met Leu Glu Ala Ala Thr Ser Ala Val Lys Glu Val Ala
            405                 410                 415
Thr Leu Gly Val Asp Thr Glu Ala Val Asn Gly Gly Gln Val Ala Phe
            420                 425                 430
Asp Thr Val Asn Gln Leu Asn Met Arg Ala Asp Leu Glu Thr Tyr Val
        435                 440                 445
Phe Gln Asp Asn Leu Ala Thr Ala Met Arg Arg Asp Gly Glu Ile Tyr
    450                 455                 460
Gln Ser Ile Val Asn Asp Ile Tyr Asp Val Pro Arg Asn Val Thr Ile
465                 470                 475                 480
Thr Leu Glu Asp Gly Ser Glu Lys Asp Val Gln Leu Met Ala Glu Val
            485                 490                 495
Val Asp Leu Ala Thr Gly Glu Lys Gln Val Leu Asn Asp Ile Arg Gly
            500                 505                 510
Arg Tyr Glu Cys Tyr Thr Asp Val Gly Pro Ser Phe Gln Ser Met Lys
        515                 520                 525
Gln Gln Asn Arg Ala Glu Ile Leu Glu Leu Leu Gly Lys Thr Pro Gln
        530                 535                 540
Gly Thr Pro Glu Tyr Gln Leu Leu Leu Gln Tyr Phe Thr Leu Leu
545                 550                 555                 560
Asp Gly Lys Gly Val Glu Met Met Arg Asp Tyr Ala Asn Lys Gln Leu
            565                 570                 575
```

Ile Gln Met Gly Val Lys Lys Pro Glu Thr Pro Glu Gln Gln Trp
                580             585             590

Leu Val Glu Ala Gln Gln Ala Lys Gln Gly Gln Gln Asp Pro Ala Met
            595             600             605

Val Gln Ala Gln Gly Val Leu Leu Gln Gly Gln Ala Glu Leu Ala Lys
610             615             620

Ala Gln Asn Gln Thr Leu Ser Leu Gln Ile Asp Ala Ala Lys Val Glu
625             630             635             640

Ala Gln Asn Gln Leu Asn Ala Ala Arg Ile Ala Glu Ile Phe Asn Asn
            645             650             655

Met Asp Leu Ser Lys Gln Ser Glu Phe Arg Glu Phe Leu Lys Thr Val
            660             665             670

Ala Ser Phe Gln Gln Asp Arg Ser Glu Asp Ala Arg Ala Asn Ala Glu
            675             680             685

Leu Leu Leu Lys Gly Asp Glu Gln Thr His Lys Gln Arg Met Asp Ile
            690             695             700

Ala Asn Ile Leu Gln Ser Gln Arg Gln Asn Gln Pro Ser Gly Ser Val
705             710             715             720

Ala Glu Thr Pro Gln
                725

<210> SEQ ID NO 14
<211> LENGTH: 344
<212> TYPE: PRT
<213> ORGANISM: Enterobacteria phage P2

<400> SEQUENCE: 14

Met Ser Lys Lys Lys Gly Lys Thr Pro Gln Pro Ala Ala Lys Thr Met
1               5               10              15

Thr Ala Ser Gly Pro Lys Met Glu Ala Phe Thr Phe Gly Glu Pro Val
            20              25              30

Pro Val Leu Asp Arg Arg Asp Ile Leu Asp Tyr Val Glu Cys Ile Ser
            35              40              45

Asn Gly Arg Trp Tyr Glu Pro Pro Val Ser Phe Thr Gly Leu Ala Lys
50              55              60

Ser Leu Arg Ala Ala Val His His Ser Ser Pro Ile Tyr Val Lys Arg
65              70              75              80

Asn Ile Leu Ala Ser Thr Phe Ile Pro His Pro Trp Leu Ser Gln Gln
            85              90              95

Asp Phe Ser Arg Phe Val Leu Asp Phe Leu Val Phe Gly Asn Ala Phe
            100             105             110

Leu Glu Lys Arg Tyr Ser Thr Thr Gly Lys Val Ile Arg Leu Glu Thr
            115             120             125

Ser Pro Ala Lys Tyr Thr Arg Arg Gly Val Glu Asp Val Tyr Trp
            130             135             140

Trp Val Pro Ser Phe Asn Glu Pro Thr Ala Phe Ala Pro Gly Ser Val
145             150             155             160

Phe His Leu Leu Glu Pro Asp Ile Asn Gln Glu Leu Tyr Gly Leu Pro
            165             170             175

Glu Tyr Leu Ser Ala Leu Asn Ser Ala Trp Leu Asn Glu Ser Ala Thr
            180             185             190

Leu Phe Arg Arg Lys Tyr Tyr Glu Asn Gly Ala His Ala Gly Tyr Ile
            195             200             205

Met Tyr Val Thr Asp Ala Val Gln Asp Arg Asn Asp Ile Glu Met Leu
210             215             220

```
Arg Glu Asn Met Val Lys Ser Lys Gly Arg Asn Phe Lys Asn Leu
225                 230                 235                 240

Phe Leu Tyr Ala Pro Gln Gly Lys Ala Asp Gly Ile Lys Ile Ile Pro
                245                 250                 255

Leu Ser Glu Val Ala Thr Lys Asp Asp Phe Phe Asn Ile Lys Lys Ala
            260                 265                 270

Ser Ala Ala Asp Leu Leu Asp Ala His Arg Ile Pro Phe Gln Leu Met
        275                 280                 285

Gly Gly Lys Pro Glu Asn Val Gly Ser Leu Gly Asp Ile Glu Lys Val
    290                 295                 300

Ala Lys Val Phe Val Arg Asn Glu Leu Ile Pro Leu Gln Asp Arg Ile
305                 310                 315                 320

Arg Glu Ile Asn Gly Trp Leu Gly Gln Glu Val Ile Arg Phe Lys Asn
                325                 330                 335

Tyr Ser Leu Asp Thr Asp Asn Asp
            340
```

```
<210> SEQ ID NO 15
<211> LENGTH: 535
<212> TYPE: PRT
<213> ORGANISM: Enterobacteria phage T3

<400> SEQUENCE: 15

Met Ala Asp Ser Lys Arg Thr Gly Leu Gly Glu Asp Gly Ala Lys Ala
1               5                   10                  15

Thr Tyr Asp Arg Leu Thr Asn Asp Arg Arg Ala Tyr Glu Thr Arg Ala
            20                  25                  30

Glu Asn Cys Ala Gln Tyr Thr Ile Pro Ser Leu Phe Pro Lys Glu Ser
        35                  40                  45

Asp Asn Glu Ser Thr Asp Tyr Thr Thr Pro Trp Gln Ala Val Gly Ala
    50                  55                  60

Arg Gly Leu Asn Asn Leu Ala Ser Lys Leu Met Leu Ala Leu Phe Pro
65                  70                  75                  80

Met Gln Ser Trp Met Lys Leu Thr Ile Ser Glu Tyr Glu Ala Lys Gln
                85                  90                  95

Leu Val Gly Asp Pro Asp Gly Leu Ala Lys Val Asp Glu Gly Leu Ser
            100                 105                 110

Met Val Glu Arg Ile Ile Met Asn Tyr Ile Glu Ser Asn Ser Tyr Arg
        115                 120                 125

Val Thr Leu Phe Glu Cys Leu Lys Gln Leu Ile Val Ala Gly Asn Ala
    130                 135                 140

Leu Leu Tyr Leu Pro Glu Pro Glu Gly Ser Tyr Asn Pro Met Lys Leu
145                 150                 155                 160

Tyr Arg Leu Ser Ser Tyr Val Val Gln Arg Asp Ala Tyr Gly Asn Val
                165                 170                 175

Leu Gln Ile Val Thr Arg Asp Gln Ile Ala Phe Gly Ala Leu Pro Glu
            180                 185                 190

Asp Val Arg Ser Ala Val Glu Lys Ser Gly Gly Glu Lys Lys Met Asp
        195                 200                 205

Glu Met Val Asp Val Tyr Thr His Val Tyr Leu Asp Glu Glu Ser Gly
    210                 215                 220

Asp Tyr Leu Lys Tyr Glu Glu Val Asp Val Glu Ile Asp Gly Ser
225                 230                 235                 240

Asp Ala Thr Tyr Pro Thr Asp Ala Met Pro Tyr Ile Pro Val Arg Met
                245                 250                 255
```

Val Arg Ile Asp Gly Glu Ser Tyr Gly Arg Ser Tyr Cys Glu Tyr
            260                 265                 270

Leu Gly Asp Leu Arg Ser Leu Glu Asn Leu Gln Glu Ala Ile Val Lys
        275                 280                 285

Met Ser Met Ile Ser Ala Lys Val Ile Gly Leu Val Asn Pro Ala Gly
    290                 295                 300

Ile Thr Gln Pro Arg Arg Leu Thr Lys Ala Gln Thr Gly Asp Phe Val
305                 310                 315                 320

Pro Gly Arg Arg Glu Asp Ile Asp Phe Leu Gln Leu Glu Lys Gln Ala
            325                 330                 335

Asp Phe Thr Val Ala Lys Ala Val Ser Asp Gln Ile Glu Ala Arg Leu
        340                 345                 350

Ser Tyr Ala Phe Met Leu Asn Ser Ala Val Gln Arg Thr Gly Glu Arg
    355                 360                 365

Val Thr Ala Glu Glu Ile Arg Tyr Val Ala Ser Glu Leu Glu Asp Thr
370                 375                 380

Leu Gly Gly Val Tyr Ser Ile Leu Ser Gln Glu Leu Gln Leu Pro Leu
385                 390                 395                 400

Val Arg Val Leu Leu Lys Gln Leu Gln Ala Thr Ser Gln Ile Pro Glu
            405                 410                 415

Leu Pro Lys Glu Ala Val Glu Pro Thr Ile Ser Thr Gly Leu Glu Ala
        420                 425                 430

Ile Gly Arg Gly Gln Asp Leu Asp Lys Leu Glu Arg Cys Ile Ser Ala
    435                 440                 445

Trp Ala Ala Leu Ala Pro Met Gln Gly Asp Pro Asp Ile Asn Leu Ala
450                 455                 460

Val Ile Lys Leu Arg Ile Ala Asn Ala Ile Gly Ile Asp Thr Ser Gly
465                 470                 475                 480

Ile Leu Leu Thr Asp Glu Gln Lys Gln Ala Leu Met Met Gln Asp Ala
            485                 490                 495

Ala Gln Thr Gly Val Glu Asn Ala Ala Ala Gly Gly Ala Gly Val
        500                 505                 510

Gly Ala Leu Ala Thr Ser Ser Pro Glu Ala Met Gln Gly Ala Ala Ala
    515                 520                 525

Lys Ala Gly Leu Asn Ala Thr
530                 535

<210> SEQ ID NO 16
<211> LENGTH: 403
<212> TYPE: PRT
<213> ORGANISM: Enterobacteria phage T5

<400> SEQUENCE: 16

Met Gly Phe Lys Ser Trp Ile Thr Glu Lys Leu Asn Pro Gly Gln Arg
  1               5                  10                  15

Ile Ile Arg Asp Met Glu Pro Val Ser His Arg Thr Asn Arg Lys Pro
            20                  25                  30

Phe Thr Thr Gly Gln Ala Tyr Ser Lys Ile Glu Ile Leu Asn Arg Thr
        35                  40                  45

Ala Asn Met Val Ile Asp Ser Ala Ala Glu Cys Ser Tyr Thr Val Gly
    50                  55                  60

Asp Lys Tyr Asn Ile Val Thr Tyr Ala Asn Gly Val Lys Thr Lys Thr
65                  70                  75                  80

Leu Asp Thr Leu Leu Asn Val Arg Pro Asn Pro Phe Met Asp Ile Ser
            85                  90                  95

```
Thr Phe Arg Arg Leu Val Val Thr Asp Leu Leu Phe Glu Gly Cys Ala
                100                 105                 110

Tyr Ile Tyr Trp Asp Gly Thr Ser Leu Tyr His Val Pro Ala Ala Leu
            115                 120                 125

Met Gln Val Glu Ala Asp Ala Asn Lys Phe Ile Lys Lys Phe Ile Phe
130                 135                 140

Asn Asn Gln Ile Asn Tyr Arg Val Asp Glu Ile Ile Phe Ile Lys Asp
145                 150                 155                 160

Asn Ser Tyr Val Cys Gly Thr Asn Ser Gln Ile Ser Gly Gln Ser Arg
                165                 170                 175

Val Ala Thr Val Ile Asp Ser Leu Glu Lys Arg Ser Lys Met Leu Asn
            180                 185                 190

Phe Lys Glu Lys Phe Leu Asp Asn Gly Thr Val Ile Gly Leu Ile Leu
        195                 200                 205

Glu Thr Asp Glu Ile Leu Asn Lys Lys Leu Arg Glu Arg Lys Gln Glu
210                 215                 220

Glu Leu Gln Leu Asp Tyr Asn Pro Ser Thr Gly Gln Ser Ser Val Leu
225                 230                 235                 240

Ile Leu Asp Gly Gly Met Lys Ala Lys Pro Tyr Ser Gln Ile Ser Ser
                245                 250                 255

Phe Lys Asp Leu Asp Phe Lys Glu Asp Ile Glu Gly Phe Asn Lys Ser
            260                 265                 270

Ile Cys Leu Ala Phe Gly Val Pro Gln Val Leu Leu Asp Gly Gly Asn
        275                 280                 285

Asn Ala Asn Ile Arg Pro Asn Ile Glu Leu Phe Tyr Tyr Met Thr Ile
290                 295                 300

Ile Pro Met Leu Asn Lys Leu Thr Ser Ser Leu Thr Phe Phe Phe Gly
305                 310                 315                 320

Tyr Lys Ile Thr Pro Asn Thr Lys Glu Val Ala Ala Leu Thr Pro Asp
                325                 330                 335

Lys Glu Ala Glu Ala Lys His Leu Thr Ser Leu Val Asn Asn Gly Ile
            340                 345                 350

Ile Thr Gly Asn Glu Ala Arg Ser Glu Leu Asn Leu Glu Pro Leu Asp
        355                 360                 365

Asp Glu Gln Met Asn Lys Ile Arg Ile Pro Ala Asn Val Ala Gly Ser
370                 375                 380

Ala Thr Gly Val Ser Gly Gln Glu Gly Gly Arg Pro Lys Gly Ser Thr
385                 390                 395                 400

Glu Gly Asp

<210> SEQ ID NO 17
<211> LENGTH: 403
<212> TYPE: PRT
<213> ORGANISM: Enterobacteria phage T5

<400> SEQUENCE: 17

Met Gly Phe Lys Ser Trp Ile Thr Glu Lys Leu Asn Pro Gly Gln Arg
1               5                   10                  15

Ile Ile Arg Asp Met Glu Pro Val Ser His Arg Thr Asn Arg Lys Pro
                20                  25                  30

Phe Thr Thr Gly Gln Ala Tyr Ser Lys Ile Glu Ile Leu Asn Arg Thr
            35                  40                  45

Ala Asn Met Val Ile Asp Ser Ala Ala Glu Cys Ser Tyr Thr Val Gly
50                  55                  60
```

Asp Lys Tyr Asn Ile Val Thr Tyr Ala Asn Gly Val Lys Thr Lys Thr
 65                  70                  75                  80

Leu Asp Thr Leu Leu Asn Val Arg Pro Asn Pro Phe Met Asp Ile Ser
                 85                  90                  95

Thr Phe Arg Arg Leu Val Val Thr Asp Leu Leu Phe Glu Gly Cys Ala
            100                 105                 110

Tyr Ile Tyr Trp Asp Gly Thr Ser Leu Tyr His Val Pro Ala Ala Leu
        115                 120                 125

Met Gln Val Glu Ala Asp Ala Asn Lys Phe Ile Lys Lys Phe Ile Phe
    130                 135                 140

Asn Asn Gln Ile Asn Tyr Arg Val Asp Glu Ile Ile Phe Ile Lys Asp
145                 150                 155                 160

Asn Ser Tyr Val Cys Gly Thr Asn Ser Gln Ile Ser Gly Gln Ser Arg
                165                 170                 175

Val Ala Thr Val Ile Asp Ser Leu Glu Lys Arg Ser Lys Met Leu Asn
            180                 185                 190

Phe Lys Glu Lys Phe Leu Asp Asn Gly Thr Val Ile Gly Leu Ile Leu
        195                 200                 205

Glu Thr Asp Glu Ile Leu Asn Lys Lys Leu Arg Glu Arg Lys Gln Glu
    210                 215                 220

Glu Leu Gln Leu Asp Tyr Asn Pro Ser Thr Gly Gln Ser Ser Val Leu
225                 230                 235                 240

Ile Leu Asp Gly Gly Met Lys Ala Lys Pro Tyr Ser Gln Ile Ser Ser
                245                 250                 255

Phe Lys Asp Leu Asp Phe Lys Glu Asp Ile Glu Gly Phe Asn Lys Ser
            260                 265                 270

Ile Cys Leu Ala Phe Gly Val Pro Gln Val Leu Leu Asp Gly Gly Asn
        275                 280                 285

Asn Ala Asn Ile Arg Pro Asn Ile Glu Leu Phe Tyr Tyr Met Thr Ile
    290                 295                 300

Ile Pro Met Leu Asn Lys Leu Thr Ser Ser Leu Thr Phe Phe Phe Gly
305                 310                 315                 320

Tyr Lys Ile Thr Pro Asn Thr Lys Glu Val Ala Ala Leu Thr Pro Asp
                325                 330                 335

Lys Glu Ala Glu Ala Lys His Leu Thr Ser Leu Val Asn Asn Gly Ile
            340                 345                 350

Ile Thr Gly Asn Glu Ala Arg Ser Glu Leu Asn Leu Gly Pro Leu Asp
        355                 360                 365

Asp Glu Gln Met Asn Lys Ile Arg Ile Pro Ala Asn Val Ala Gly Ser
    370                 375                 380

Ala Thr Gly Val Ser Gly Gln Glu Gly Gly Arg Pro Lys Gly Ser Thr
385                 390                 395                 400

Glu Gly Asp

<210> SEQ ID NO 18
<211> LENGTH: 403
<212> TYPE: PRT
<213> ORGANISM: Enterobacteria phage T5

<400> SEQUENCE: 18

Met Gly Phe Lys Ser Trp Ile Thr Glu Lys Leu Asn Pro Gly Gln Arg
 1               5                  10                  15

Ile Ile Arg Asp Met Glu Pro Val Ser His Arg Thr Asn Arg Lys Pro
                20                  25                  30

Phe Thr Thr Gly Gln Ala Tyr Ser Lys Ile Glu Ile Leu Asn Arg Thr
            35                  40                  45

Ala Asn Met Val Ile Asp Ser Ala Ala Glu Cys Ser Tyr Thr Val Gly
 50                  55                  60

Asp Lys Tyr Asn Ile Val Thr Tyr Ala Asn Gly Val Lys Thr Lys Thr
 65                  70                  75                  80

Leu Asp Thr Leu Leu Asn Val Arg Pro Asn Pro Phe Met Asp Ile Ser
                 85                  90                  95

Thr Phe Arg Arg Leu Val Val Thr Asp Leu Leu Phe Glu Gly Cys Ala
            100                 105                 110

Tyr Ile Tyr Trp Asp Gly Thr Ser Leu Tyr His Val Pro Ala Ala Leu
            115                 120                 125

Met Gln Val Glu Ala Asp Ala Asn Lys Phe Ile Lys Lys Phe Ile Phe
            130                 135                 140

Asn Asn Gln Ile Asn Tyr Arg Val Asp Glu Ile Ile Phe Ile Lys Asp
145                 150                 155                 160

Asn Ser Tyr Val Cys Gly Thr Asn Ser Gln Ile Ser Gly Gln Ser Arg
                165                 170                 175

Val Ala Thr Val Ile Asp Ser Leu Glu Lys Arg Ser Lys Met Leu Asn
            180                 185                 190

Phe Lys Glu Lys Phe Leu Asp Asn Gly Thr Val Ile Gly Leu Ile Leu
            195                 200                 205

Glu Thr Asp Glu Ile Leu Asn Lys Lys Leu Arg Glu Arg Lys Gln Glu
            210                 215                 220

Glu Leu Gln Leu Asp Tyr Asn Pro Ser Thr Gly Gln Ser Ser Val Leu
225                 230                 235                 240

Ile Leu Asp Gly Gly Met Lys Ala Lys Pro Tyr Ser Gln Ile Ser Ser
            245                 250                 255

Phe Lys Asp Leu Asp Phe Lys Glu Asp Ile Glu Gly Phe Asn Lys Ser
            260                 265                 270

Ile Cys Leu Ala Phe Gly Val Pro Gln Val Leu Leu Asp Gly Gly Asn
            275                 280                 285

Asn Ala Asn Ile Arg Pro Asn Ile Glu Leu Phe Tyr Tyr Met Thr Ile
            290                 295                 300

Ile Pro Met Leu Asn Lys Leu Thr Ser Ser Leu Thr Phe Phe Phe Gly
305                 310                 315                 320

Tyr Lys Ile Thr Pro Asn Thr Lys Glu Val Ala Ala Leu Thr Pro Asp
            325                 330                 335

Lys Glu Ala Glu Ala Lys His Leu Thr Ser Leu Val Asn Asn Gly Ile
            340                 345                 350

Ile Thr Gly Asn Glu Ala Arg Ser Glu Leu Asn Leu Glu Pro Leu Asp
            355                 360                 365

Asp Glu Gln Met Asn Lys Ile Arg Ile Pro Ala Asn Val Ala Gly Ser
            370                 375                 380

Ala Thr Gly Val Ser Gly Gln Glu Gly Gly Arg Pro Lys Gly Ser Thr
385                 390                 395                 400

Glu Gly Asp

<210> SEQ ID NO 19
<211> LENGTH: 403
<212> TYPE: PRT
<213> ORGANISM: Enterobacteria phage T5

<400> SEQUENCE: 19

```
Met Gly Phe Lys Ser Trp Ile Thr Glu Lys Leu Asn Pro Gly Gln Arg
  1               5                  10                  15

Ile Ile Arg Asp Met Glu Pro Val Ser His Arg Thr Asn Arg Lys Pro
             20                  25                  30

Phe Thr Thr Gly Gln Ala Tyr Ser Lys Ile Glu Ile Leu Asn Arg Thr
         35                  40                  45

Ala Asn Met Val Ile Asp Ser Ala Ala Glu Cys Ser Tyr Thr Val Gly
     50                  55                  60

Asp Lys Tyr Asn Ile Val Thr Tyr Ala Asn Gly Val Lys Thr Lys Thr
 65                  70                  75                  80

Leu Asp Thr Leu Leu Asn Val Arg Pro Asn Pro Phe Met Asp Ile Ser
                 85                  90                  95

Thr Phe Arg Arg Leu Val Val Thr Asp Leu Leu Phe Glu Gly Cys Ala
            100                 105                 110

Tyr Ile Tyr Trp Asp Gly Thr Ser Leu Tyr His Val Pro Ala Ala Leu
        115                 120                 125

Met Gln Val Glu Ala Asp Ala Asn Lys Phe Ile Lys Lys Phe Ile Phe
    130                 135                 140

Asn Asn Gln Ile Asn Tyr Arg Val Asp Glu Ile Ile Phe Ile Lys Asp
145                 150                 155                 160

Asn Ser Tyr Val Cys Gly Thr Asn Ser Gln Ile Ser Gly Gln Ser Arg
                165                 170                 175

Val Ala Thr Val Ile Asp Ser Leu Glu Lys Arg Ser Lys Met Leu Asn
            180                 185                 190

Phe Lys Glu Lys Phe Leu Asp Asn Gly Thr Val Ile Gly Leu Ile Leu
        195                 200                 205

Glu Thr Asp Glu Ile Leu Asn Lys Lys Leu Arg Glu Arg Lys Gln Glu
    210                 215                 220

Glu Leu Gln Leu Asp Tyr Asn Pro Ser Thr Gly Gln Ser Ser Val Leu
225                 230                 235                 240

Ile Leu Asp Gly Gly Met Lys Ala Lys Pro Tyr Ser Gln Ile Ser Ser
                245                 250                 255

Phe Lys Asp Leu Asp Phe Lys Glu Asp Ile Glu Gly Phe Asn Lys Ser
            260                 265                 270

Ile Cys Leu Ala Phe Gly Val Pro Gln Val Leu Leu Asp Gly Gly Asn
        275                 280                 285

Asn Ala Asn Ile Arg Pro Asn Ile Glu Leu Phe Tyr Tyr Met Thr Ile
    290                 295                 300

Ile Pro Met Leu Asn Lys Leu Thr Ser Ser Leu Thr Phe Phe Phe Gly
305                 310                 315                 320

Tyr Lys Ile Thr Pro Asn Thr Lys Glu Val Ala Ala Leu Thr Pro Asp
                325                 330                 335

Lys Glu Ala Glu Ala Lys His Leu Thr Ser Leu Val Asn Asn Gly Ile
            340                 345                 350

Ile Thr Gly Asn Glu Ala Arg Ser Glu Leu Asn Leu Glu Pro Leu Asp
        355                 360                 365

Asp Glu Gln Met Asn Lys Ile Arg Ile Pro Ala Asn Val Ala Gly Ser
    370                 375                 380

Ala Thr Gly Val Ser Gly Gln Glu Gly Gly Arg Pro Lys Gly Ser Thr
385                 390                 395                 400

Glu Gly Asp
```

<210> SEQ ID NO 20
<211> LENGTH: 536
<212> TYPE: PRT
<213> ORGANISM: Enterobacteria phage T7

<400> SEQUENCE: 20

```
Met Ala Glu Lys Arg Thr Gly Leu Ala Glu Asp Gly Ala Lys Ser Val
 1               5                  10                  15

Tyr Glu Arg Leu Lys Asn Asp Arg Ala Pro Tyr Glu Thr Arg Ala Gln
                20                  25                  30

Asn Cys Ala Gln Tyr Thr Ile Pro Ser Leu Phe Pro Lys Asp Ser Asp
            35                  40                  45

Asn Ala Ser Thr Asp Tyr Gln Thr Pro Trp Gln Ala Val Gly Ala Arg
50                  55                  60

Gly Leu Asn Asn Leu Ala Ser Lys Leu Met Leu Ala Leu Phe Pro Met
65                  70                  75                  80

Gln Thr Trp Met Arg Leu Thr Ile Ser Glu Tyr Glu Ala Lys Gln Leu
                85                  90                  95

Leu Ser Asp Pro Asp Gly Leu Ala Lys Val Asp Glu Gly Leu Ser Met
            100                 105                 110

Val Glu Arg Ile Ile Met Asn Tyr Ile Glu Ser Asn Ser Tyr Arg Val
        115                 120                 125

Thr Leu Phe Glu Ala Leu Lys Gln Leu Val Val Ala Gly Asn Val Leu
130                 135                 140

Leu Tyr Leu Pro Glu Pro Glu Gly Ser Asn Tyr Asn Pro Met Lys Leu
145                 150                 155                 160

Tyr Arg Leu Ser Ser Tyr Val Val Gln Arg Asp Ala Phe Gly Asn Val
                165                 170                 175

Leu Gln Met Val Thr Arg Asp Gln Ile Ala Phe Gly Ala Leu Pro Glu
            180                 185                 190

Asp Ile Arg Lys Ala Val Glu Gly Gln Gly Gly Glu Lys Lys Ala Asp
        195                 200                 205

Glu Thr Ile Asp Val Tyr Thr His Ile Tyr Leu Asp Glu Asp Ser Gly
210                 215                 220

Glu Tyr Leu Arg Tyr Glu Glu Val Glu Gly Met Glu Val Gln Gly Ser
225                 230                 235                 240

Asp Gly Thr Tyr Pro Lys Glu Ala Cys Pro Tyr Ile Pro Ile Arg Met
                245                 250                 255

Val Arg Leu Asp Gly Glu Ser Tyr Gly Arg Ser Tyr Ile Glu Glu Tyr
            260                 265                 270

Leu Gly Asp Leu Arg Ser Leu Glu Asn Leu Gln Glu Ala Ile Val Lys
        275                 280                 285

Met Ser Met Ile Ser Ser Lys Val Ile Gly Leu Val Asn Pro Ala Gly
290                 295                 300

Ile Thr Gln Pro Arg Arg Leu Thr Lys Ala Gln Thr Gly Asp Phe Val
305                 310                 315                 320

Thr Gly Arg Pro Glu Asp Ile Ser Phe Leu Gln Leu Glu Lys Gln Ala
                325                 330                 335

Asp Phe Thr Val Ala Lys Ala Val Ser Asp Ala Ile Glu Ala Arg Leu
            340                 345                 350

Ser Phe Ala Phe Met Leu Asn Ser Ala Val Gln Arg Thr Gly Glu Arg
        355                 360                 365

Val Thr Ala Glu Glu Ile Arg Tyr Val Ala Ser Glu Leu Glu Asp Thr
370                 375                 380
```

-continued

```
Leu Gly Gly Val Tyr Ser Ile Leu Ser Gln Glu Leu Gln Leu Pro Leu
385                 390                 395                 400

Val Arg Val Leu Leu Lys Gln Leu Gln Ala Thr Gln Gln Ile Pro Glu
                405                 410                 415

Leu Pro Lys Glu Ala Val Glu Pro Thr Ile Ser Thr Gly Leu Glu Ala
            420                 425                 430

Ile Gly Arg Gly Gln Asp Leu Asp Lys Leu Glu Arg Cys Val Thr Ala
        435                 440                 445

Trp Ala Leu Ala Pro Met Arg Asp Asp Pro Asp Ile Asn Leu Ala
    450                 455                 460

Met Ile Lys Leu Arg Ile Ala Asn Ala Ile Gly Ile Asp Thr Ser Gly
465                 470                 475                 480

Ile Leu Leu Thr Glu Glu Lys Gln Gln Lys Met Ala Gln Gln Ser
                485                 490                 495

Met Gln Met Gly Met Asp Asn Gly Ala Ala Ala Leu Ala Gln Gly Met
                500                 505                 510

Ala Ala Gln Ala Thr Ala Ser Pro Glu Ala Met Ala Ala Ala Ala Asp
            515                 520                 525

Ser Val Gly Leu Gln Pro Gly Ile
            530                 535

<210> SEQ ID NO 21
<211> LENGTH: 14
<212> TYPE: PRT
<213> ORGANISM: Artificial Sequence
<220> FEATURE:
<223> OTHER INFORMATION: Peptide sequence used in fusion construct

<400> SEQUENCE: 21

Gly Gly Gly Gly Gly Gly Trp Ser His Pro Gln Phe Glu Lys
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Peptide sequence used in fusion construct

<400> SEQUENCE: 22

Trp Ser His Pro Gln Phe Glu Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Peptide sequence used in fusion construct

<400> SEQUENCE: 23

Gly Gly Gly Gly Gly Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Peptide sequence used in fusion construct
```

```
<400> SEQUENCE: 24

Leu Glu His His His His His His
1               5

<210> SEQ ID NO 25
<211> LENGTH: 6
<212> TYPE: PRT
<213> ORGANISM: Artificial Sequence
<220> FEATURE:
<223> OTHER INFORMATION: Peptide sequence used in fusion construct

<400> SEQUENCE: 25

His His His His His His
1               5

<210> SEQ ID NO 26
<211> LENGTH: 14
<212> TYPE: PRT
<213> ORGANISM: Artificial Sequence
<220> FEATURE:
<223> OTHER INFORMATION: Peptide sequence used in fusion construct

<400> SEQUENCE: 26

Asp Tyr Asp Ile Pro Thr Thr Glu Asn Leu Tyr Phe Gln Gly
1               5                   10

<210> SEQ ID NO 27
<211> LENGTH: 40
<212> TYPE: PRT
<213> ORGANISM: Artificial Sequence
<220> FEATURE:
<223> OTHER INFORMATION: Peptide sequence used in fusion construct

<400> SEQUENCE: 27

Trp Ser His Pro Gln Phe Glu Lys Gly Gly Gly Gly Gly Gly Gly
1               5                   10                  15

Gly Gly Ala Met His His His His His His Asp Tyr Asp Ile Pro Thr
            20                  25                  30

Thr Glu Asn Leu Tyr Phe Gln Gly
        35                  40

<210> SEQ ID NO 28
<211> LENGTH: 18
<212> TYPE: PRT
<213> ORGANISM: Artificial Sequence
<220> FEATURE:
<223> OTHER INFORMATION: Peptide sequence used in fusion construct

<400> SEQUENCE: 28

Trp Ser His Pro Gln Phe Glu Lys Gly Gly Gly Gly Gly Gly Gly
1               5                   10                  15

Gly Gly

<210> SEQ ID NO 29
<211> LENGTH: 20
<212> TYPE: PRT
<213> ORGANISM: Artificial Sequence
<220> FEATURE:
<223> OTHER INFORMATION: Peptide sequence used in fusion construct
```

```
<400> SEQUENCE: 29

His His His His His Asp Tyr Asp Ile Pro Thr Thr Glu Asn Leu
1               5                   10                  15

Tyr Phe Gln Gly
            20

<210> SEQ ID NO 30
<211> LENGTH: 22
<212> TYPE: PRT
<213> ORGANISM: Artificial Sequence
<220> FEATURE:
<223> OTHER INFORMATION: Peptide sequence used in fusion construct

<400> SEQUENCE: 30

Trp Ser His Pro Gln Phe Glu Lys Asp Tyr Asp Ile Pro Thr Thr Glu
1               5                   10                  15

Asn Leu Tyr Phe Gln Gly
            20

<210> SEQ ID NO 31
<211> LENGTH: 323
<212> TYPE: PRT
<213> ORGANISM: Artificial Sequence
<220> FEATURE:
<223> OTHER INFORMATION: gp10-CStrep fusion protein

<400> SEQUENCE: 31

Met Ala Arg Lys Arg Ser Asn Thr Tyr Arg Ser Ile Asn Glu Ile Gln
1               5                   10                  15

Arg Gln Lys Arg Asn Arg Trp Phe Ile His Tyr Leu Asn Tyr Leu Gln
            20                  25                  30

Ser Leu Ala Tyr Gln Leu Phe Glu Trp Glu Asn Leu Pro Pro Thr Ile
        35                  40                  45

Asn Pro Ser Phe Leu Glu Lys Ser Ile His Gln Phe Gly Tyr Val Gly
    50                  55                  60

Phe Tyr Lys Asp Pro Val Ile Ser Tyr Ile Ala Cys Asn Gly Ala Leu
65                  70                  75                  80

Ser Gly Gln Arg Asp Val Tyr Asn Gln Ala Thr Val Phe Arg Ala Ala
                85                  90                  95

Ser Pro Val Tyr Gln Lys Glu Phe Lys Leu Tyr Asn Tyr Arg Asp Met
            100                 105                 110

Lys Glu Glu Asp Met Gly Val Val Ile Tyr Asn Asn Asp Met Ala Phe
        115                 120                 125

Pro Thr Thr Pro Thr Leu Glu Leu Phe Ala Ala Glu Leu Ala Glu Leu
    130                 135                 140

Lys Glu Ile Ile Ser Val Asn Gln Asn Ala Gln Lys Thr Pro Val Leu
145                 150                 155                 160

Ile Arg Ala Asn Asp Asn Asn Gln Leu Ser Leu Lys Gln Val Tyr Asn
                165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
        195                 200                 205

Lys Leu Asn Ala Gln Lys Asn Ala Val Trp Asn Glu Met Met Thr Phe
    210                 215                 220

Leu Gly Ile Lys Asn Ala Asn Leu Glu Lys Lys Glu Arg Met Val Thr
225                 230                 235                 240
```

Asp Glu Val Ser Ser Asn Asp Glu Gln Ile Glu Ser Gly Thr Val
                    245                 250                 255

Phe Leu Lys Ser Arg Glu Glu Ala Cys Glu Lys Ile Asn Glu Leu Tyr
            260                 265                 270

Gly Leu Asn Val Lys Val Lys Phe Arg Tyr Asp Ile Val Glu Gln Met
        275                 280                 285

Arg Arg Glu Leu Gln Gln Ile Glu Asn Val Ser Arg Gly Thr Ser Asp
    290                 295                 300

Gly Glu Thr Asn Glu Gly Gly Gly Gly Gly Trp Ser His Pro Gln
305                 310                 315                 320

Phe Glu Lys

<210> SEQ ID NO 32
<211> LENGTH: 349
<212> TYPE: PRT
<213> ORGANISM: Artificial Sequence
<220> FEATURE:
<223> OTHER INFORMATION: gp10-NStrephis fusion protein

<400> SEQUENCE: 32

Met Trp Ser His Pro Gln Phe Glu Lys Gly Gly Gly Gly Gly Gly Gly
 1               5                  10                  15

Gly Gly Gly Ala Met His His His His His His Asp Tyr Asp Ile Pro
            20                  25                  30

Thr Thr Glu Asn Leu Tyr Phe Gln Gly Ala Arg Lys Arg Ser Asn Thr
        35                  40                  45

Tyr Arg Ser Ile Asn Glu Ile Gln Arg Gln Lys Arg Asn Arg Trp Phe
    50                  55                  60

Ile His Tyr Leu Asn Tyr Leu Gln Ser Leu Ala Tyr Gln Leu Phe Glu
65                  70                  75                  80

Trp Glu Asn Leu Pro Pro Thr Ile Asn Pro Ser Phe Leu Glu Lys Ser
                85                  90                  95

Ile His Gln Phe Gly Tyr Val Gly Phe Tyr Lys Asp Pro Val Ile Ser
            100                 105                 110

Tyr Ile Ala Cys Asn Gly Ala Leu Ser Gly Gln Arg Asp Val Tyr Asn
        115                 120                 125

Gln Ala Thr Val Phe Arg Ala Ala Ser Pro Val Tyr Gln Lys Glu Phe
    130                 135                 140

Lys Leu Tyr Asn Tyr Arg Asp Met Lys Glu Glu Asp Met Gly Val Val
145                 150                 155                 160

Ile Tyr Asn Asn Asp Met Ala Phe Pro Thr Thr Pro Thr Leu Glu Leu
                165                 170                 175

Phe Ala Ala Glu Leu Ala Glu Leu Lys Glu Ile Ile Ser Val Asn Gln
            180                 185                 190

Asn Ala Gln Lys Thr Pro Val Leu Ile Arg Ala Asn Asp Asn Gln
        195                 200                 205

Leu Ser Leu Lys Gln Val Tyr Asn Gln Tyr Glu Gly Asn Ala Pro Val
    210                 215                 220

Ile Phe Ala His Glu Ala Leu Asp Ser Asp Ser Ile Glu Val Phe Lys
225                 230                 235                 240

Thr Asp Ala Pro Tyr Val Val Asp Lys Leu Asn Ala Gln Lys Asn Ala
                245                 250                 255

Val Trp Asn Glu Met Met Thr Phe Leu Gly Ile Lys Asn Ala Asn Leu
            260                 265                 270

```
Glu Lys Lys Glu Arg Met Val Thr Asp Glu Val Ser Ser Asn Asp Glu
            275                 280                 285

Gln Ile Glu Ser Ser Gly Thr Val Phe Leu Lys Ser Arg Glu Glu Ala
        290                 295                 300

Cys Glu Lys Ile Asn Glu Leu Tyr Gly Leu Asn Val Lys Val Lys Phe
305                 310                 315                 320

Arg Tyr Asp Ile Val Glu Gln Met Arg Arg Glu Leu Gln Gln Ile Glu
                325                 330                 335

Asn Val Ser Arg Gly Thr Ser Asp Gly Glu Thr Asn Glu
            340                 345
```

<210> SEQ ID NO 33
<211> LENGTH: 331
<212> TYPE: PRT
<213> ORGANISM: Artificial Sequence
<220> FEATURE:
<223> OTHER INFORMATION: gp10-NStrep fusion protein

<400> SEQUENCE: 33

```
Met Trp Ser His Pro Gln Phe Glu Lys Asp Tyr Asp Ile Pro Thr Thr
1               5                   10                  15

Glu Asn Leu Tyr Phe Gln Gly Ala Arg Lys Arg Ser Asn Thr Tyr Arg
            20                  25                  30

Ser Ile Asn Glu Ile Gln Arg Gln Lys Arg Asn Arg Trp Phe Ile His
        35                  40                  45

Tyr Leu Asn Tyr Leu Gln Ser Leu Ala Tyr Gln Leu Phe Glu Trp Glu
    50                  55                  60

Asn Leu Pro Pro Thr Ile Asn Pro Ser Phe Leu Glu Lys Ser Ile His
65                  70                  75                  80

Gln Phe Gly Tyr Val Gly Phe Tyr Lys Asp Pro Val Ile Ser Tyr Ile
                85                  90                  95

Ala Cys Asn Gly Ala Leu Ser Gly Gln Arg Asp Val Tyr Asn Gln Ala
            100                 105                 110

Thr Val Phe Arg Ala Ala Ser Pro Val Tyr Gln Lys Glu Phe Lys Leu
        115                 120                 125

Tyr Asn Tyr Arg Asp Met Lys Glu Glu Asp Met Gly Val Val Ile Tyr
    130                 135                 140

Asn Asn Asp Met Ala Phe Pro Thr Thr Pro Thr Leu Glu Leu Phe Ala
145                 150                 155                 160

Ala Glu Leu Ala Glu Leu Lys Glu Ile Ile Ser Val Asn Gln Asn Ala
                165                 170                 175

Gln Lys Thr Pro Val Leu Ile Arg Ala Asn Asp Asn Gln Leu Ser
            180                 185                 190

Leu Lys Gln Val Tyr Asn Gln Tyr Glu Gly Asn Ala Pro Val Ile Phe
        195                 200                 205

Ala His Glu Ala Leu Asp Ser Asp Ser Ile Glu Val Phe Lys Thr Asp
    210                 215                 220

Ala Pro Tyr Val Val Asp Lys Leu Asn Ala Gln Lys Asn Ala Val Trp
225                 230                 235                 240

Asn Glu Met Met Thr Phe Leu Gly Ile Lys Asn Ala Asn Leu Glu Lys
                245                 250                 255

Lys Glu Arg Met Val Thr Asp Glu Val Ser Ser Asn Asp Glu Gln Ile
            260                 265                 270

Glu Ser Ser Gly Thr Val Phe Leu Lys Ser Arg Glu Glu Ala Cys Glu
        275                 280                 285
```

```
Lys Ile Asn Glu Leu Tyr Gly Leu Asn Val Lys Val Lys Phe Arg Tyr
    290                 295                 300

Asp Ile Val Glu Gln Met Arg Arg Glu Leu Gln Gln Ile Glu Asn Val
305                 310                 315                 320

Ser Arg Gly Thr Ser Asp Gly Glu Thr Asn Glu
                325                 330

<210> SEQ ID NO 34
<211> LENGTH: 344
<212> TYPE: PRT
<213> ORGANISM: Artificial Sequence
<220> FEATURE:
<223> OTHER INFORMATION: gp10-Nhis/CStrep fusion protein

<400> SEQUENCE: 34

Met His His His His His His Asp Tyr Asp Ile Pro Thr Thr Glu Asn
1               5                   10                  15

Leu Tyr Phe Gln Gly Met Ala Arg Lys Arg Ser Asn Thr Tyr Arg Ser
                20                  25                  30

Ile Asn Glu Ile Gln Arg Gln Lys Arg Asn Arg Trp Phe Ile His Tyr
            35                  40                  45

Leu Asn Tyr Leu Gln Ser Leu Ala Tyr Gln Leu Phe Glu Trp Glu Asn
    50                  55                  60

Leu Pro Pro Thr Ile Asn Pro Ser Phe Leu Glu Lys Ser Ile His Gln
65                  70                  75                  80

Phe Gly Tyr Val Gly Phe Tyr Lys Asp Pro Val Ile Ser Tyr Ile Ala
                85                  90                  95

Cys Asn Gly Ala Leu Ser Gly Gln Arg Asp Val Tyr Asn Gln Ala Thr
            100                 105                 110

Val Phe Arg Ala Ala Ser Pro Val Tyr Gln Lys Glu Phe Lys Leu Tyr
        115                 120                 125

Asn Tyr Arg Asp Met Lys Glu Glu Asp Met Gly Val Val Ile Tyr Asn
    130                 135                 140

Asn Asp Met Ala Phe Pro Thr Thr Pro Thr Leu Glu Leu Phe Ala Ala
145                 150                 155                 160

Glu Leu Ala Glu Leu Lys Glu Ile Ile Ser Val Asn Gln Asn Ala Gln
                165                 170                 175

Lys Thr Pro Val Leu Ile Arg Ala Asn Asp Asn Gln Leu Ser Leu
            180                 185                 190

Lys Gln Val Tyr Asn Gln Tyr Glu Gly Asn Ala Pro Val Ile Phe Ala
        195                 200                 205

His Glu Ala Leu Asp Ser Asp Ser Ile Glu Val Phe Lys Thr Asp Ala
    210                 215                 220

Pro Tyr Val Val Asp Lys Leu Asn Ala Gln Lys Asn Ala Val Trp Asn
225                 230                 235                 240

Glu Met Met Thr Phe Leu Gly Ile Lys Asn Ala Asn Leu Glu Lys Lys
                245                 250                 255

Glu Arg Met Val Thr Asp Glu Val Ser Ser Asn Asp Glu Gln Ile Glu
            260                 265                 270

Ser Ser Gly Thr Val Phe Leu Lys Ser Arg Glu Glu Ala Cys Glu Lys
        275                 280                 285

Ile Asn Glu Leu Tyr Gly Leu Asn Val Lys Val Lys Phe Arg Tyr Asp
    290                 295                 300

Ile Val Glu Gln Met Arg Arg Glu Leu Gln Gln Ile Glu Asn Val Ser
305                 310                 315                 320
```

Arg Gly Thr Ser Asp Gly Glu Thr Asn Glu Gly Gly Gly Gly
             325                 330                 335

Trp Ser His Pro Gln Phe Glu Lys
             340

<210> SEQ ID NO 35
<211> LENGTH: 329
<212> TYPE: PRT
<213> ORGANISM: Artificial Sequence
<220> FEATURE:
<223> OTHER INFORMATION: gp10-Nhis fusion protein

<400> SEQUENCE: 35

Met His His His His His Asp Tyr Asp Ile Pro Thr Thr Glu Asn
  1               5                  10                  15

Leu Tyr Phe Gln Gly Ala Arg Lys Arg Ser Asn Thr Tyr Arg Ser Ile
             20                  25                  30

Asn Glu Ile Gln Arg Gln Lys Arg Asn Arg Trp Phe Ile His Tyr Leu
         35                  40                  45

Asn Tyr Leu Gln Ser Leu Ala Tyr Gln Leu Phe Glu Trp Glu Asn Leu
     50                  55                  60

Pro Pro Thr Ile Asn Pro Ser Phe Leu Glu Lys Ser Ile His Gln Phe
65                  70                  75                  80

Gly Tyr Val Gly Phe Tyr Lys Asp Pro Val Ile Ser Tyr Ile Ala Cys
                 85                  90                  95

Asn Gly Ala Leu Ser Gly Gln Arg Asp Val Tyr Asn Gln Ala Thr Val
            100                 105                 110

Phe Arg Ala Ala Ser Pro Val Tyr Gln Lys Glu Phe Lys Leu Tyr Asn
            115                 120                 125

Tyr Arg Asp Met Lys Glu Glu Asp Met Gly Val Val Ile Tyr Asn Asn
130                 135                 140

Asp Met Ala Phe Pro Thr Thr Pro Thr Leu Glu Leu Phe Ala Ala Glu
145                 150                 155                 160

Leu Ala Glu Leu Lys Glu Ile Ile Ser Val Asn Gln Asn Ala Gln Lys
                165                 170                 175

Thr Pro Val Leu Ile Arg Ala Asn Asp Asn Gln Leu Ser Leu Lys
            180                 185                 190

Gln Val Tyr Asn Gln Tyr Glu Gly Asn Ala Pro Val Ile Phe Ala His
            195                 200                 205

Glu Ala Leu Asp Ser Asp Ser Ile Glu Val Phe Lys Thr Asp Ala Pro
210                 215                 220

Tyr Val Val Asp Lys Leu Asn Ala Gln Lys Asn Ala Val Trp Asn Glu
225                 230                 235                 240

Met Met Thr Phe Leu Gly Ile Lys Asn Ala Asn Leu Glu Lys Lys Glu
                245                 250                 255

Arg Met Val Thr Asp Glu Val Ser Ser Asn Asp Glu Gln Ile Glu Ser
            260                 265                 270

Ser Gly Thr Val Phe Leu Lys Ser Arg Glu Glu Ala Cys Glu Lys Ile
            275                 280                 285

Asn Glu Leu Tyr Gly Leu Asn Val Lys Val Lys Phe Arg Tyr Asp Ile
        290                 295                 300

Val Glu Gln Met Arg Arg Glu Leu Gln Gln Ile Glu Asn Val Ser Arg
305                 310                 315                 320

Gly Thr Ser Asp Gly Glu Thr Asn Glu
            325

```
<210> SEQ ID NO 36
<211> LENGTH: 33
<212> TYPE: DNA
<213> ORGANISM: Artificial Sequence
<220> FEATURE:
<223> OTHER INFORMATION: Primer

<400> SEQUENCE: 36
cgcagctggc atatggcacg taaacgcagt aac                                    33

<210> SEQ ID NO 37
<211> LENGTH: 46
<212> TYPE: DNA
<213> ORGANISM: Artificial Sequence
<220> FEATURE:
<223> OTHER INFORMATION: Primer

<400> SEQUENCE: 37
ggatgactcc aacctcctcc accacctccc tcatttgttt caccgt                      46

<210> SEQ ID NO 38
<211> LENGTH: 46
<212> TYPE: DNA
<213> ORGANISM: Artificial Sequence
<220> FEATURE:
<223> OTHER INFORMATION: Primer

<400> SEQUENCE: 38
ataatgttct cgagctactt ttcgaactgc ggatgactcc aacctc                      46

<210> SEQ ID NO 39
<211> LENGTH: 11
<212> TYPE: PRT
<213> ORGANISM: Artificial Sequence
<220> FEATURE:
<223> OTHER INFORMATION: Peptide sequence used in fusion constructs

<400> SEQUENCE: 39

Tyr Gly Arg Lys Lys Arg Arg Gln Arg Arg
 1               5                  10

<210> SEQ ID NO 40
<211> LENGTH: 6
<212> TYPE: PRT
<213> ORGANISM: Artificial Sequence
<220> FEATURE:
<223> OTHER INFORMATION: Peptide sequence used in fusion constructs

<400> SEQUENCE: 40

Asp Arg Ala Thr Pro Tyr
 1               5

<210> SEQ ID NO 41
<211> LENGTH: 315
<212> TYPE: PRT
<213> ORGANISM: Artificial Sequence
<220> FEATURE:
<223> OTHER INFORMATION: C-His6-gp10/K234A fusion protein

<400> SEQUENCE: 41

Met Ala Arg Lys Arg Ser Asn Thr Tyr Arg Ser Ile Asn Glu Ile Gln
 1               5                  10                  15

Arg Gln Lys Arg Asn Arg Trp Phe Ile His Tyr Leu Asn Tyr Leu Gln
            20                  25                  30

Ser Leu Ala Tyr Gln Leu Phe Glu Trp Glu Asn Leu Pro Pro Thr Ile
        35                  40                  45
```

```
Asn Pro Ser Phe Leu Glu Lys Ser Ile His Gln Phe Gly Tyr Val Gly
        50                  55                  60

Phe Tyr Lys Asp Pro Val Ile Ser Tyr Ile Ala Cys Asn Gly Ala Leu
 65                  70                  75                  80

Ser Gly Gln Arg Asp Val Tyr Asn Gln Ala Thr Val Phe Arg Ala Ala
                85                  90                  95

Ser Pro Val Tyr Gln Lys Glu Phe Lys Leu Tyr Asn Tyr Arg Asp Met
            100                 105                 110

Lys Glu Glu Asp Met Gly Val Val Ile Tyr Asn Asn Asp Met Ala Phe
        115                 120                 125

Pro Thr Thr Pro Thr Leu Glu Leu Phe Ala Ala Glu Leu Ala Glu Leu
130                 135                 140

Lys Glu Ile Ile Ser Val Asn Gln Asn Ala Gln Lys Thr Pro Val Leu
145                 150                 155                 160

Ile Arg Ala Asn Asp Asn Asn Gln Leu Ser Leu Lys Gln Val Tyr Asn
                165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
        195                 200                 205

Lys Leu Asn Ala Gln Lys Asn Ala Val Trp Asn Glu Met Met Thr Phe
210                 215                 220

Leu Gly Ile Lys Asn Ala Asn Leu Glu Ala Lys Glu Arg Met Val Thr
225                 230                 235                 240

Asp Glu Val Ser Ser Asn Asp Glu Gln Ile Glu Ser Ser Gly Thr Val
                245                 250                 255

Phe Leu Lys Ser Arg Glu Glu Ala Cys Glu Lys Ile Asn Glu Leu Tyr
            260                 265                 270

Gly Leu Asn Val Lys Val Lys Phe Arg Tyr Asp Ile Val Glu Gln Met
        275                 280                 285

Arg Arg Glu Leu Gln Gln Ile Glu Asn Val Ser Arg Gly Thr Ser Asp
290                 295                 300

Gly Glu Thr Asn Glu His His His His His His
305                 310                 315

<210> SEQ ID NO 42
<211> LENGTH: 315
<212> TYPE: PRT
<213> ORGANISM: Artificial Sequence
<220> FEATURE:
<223> OTHER INFORMATION: C-His6-gp10/K234C fusion protein

<400> SEQUENCE: 42

Met Ala Arg Lys Arg Ser Asn Thr Tyr Arg Ser Ile Asn Glu Ile Gln
 1               5                  10                  15

Arg Gln Lys Arg Asn Arg Trp Phe Ile His Tyr Leu Asn Tyr Leu Gln
                20                  25                  30

Ser Leu Ala Tyr Gln Leu Phe Glu Trp Glu Asn Leu Pro Pro Thr Ile
            35                  40                  45

Asn Pro Ser Phe Leu Glu Lys Ser Ile His Gln Phe Gly Tyr Val Gly
        50                  55                  60

Phe Tyr Lys Asp Pro Val Ile Ser Tyr Ile Ala Cys Asn Gly Ala Leu
 65                  70                  75                  80

Ser Gly Gln Arg Asp Val Tyr Asn Gln Ala Thr Val Phe Arg Ala Ala
                85                  90                  95
```

```
Ser Pro Val Tyr Gln Lys Glu Phe Lys Leu Tyr Asn Tyr Arg Asp Met
            100                 105                 110

Lys Glu Glu Asp Met Gly Val Val Ile Tyr Asn Asn Asp Met Ala Phe
            115                 120                 125

Pro Thr Thr Pro Thr Leu Glu Leu Phe Ala Ala Glu Leu Ala Glu Leu
            130                 135                 140

Lys Glu Ile Ile Ser Val Asn Gln Asn Ala Gln Lys Thr Pro Val Leu
145                 150                 155                 160

Ile Arg Ala Asn Asp Asn Asn Gln Leu Ser Leu Lys Gln Val Tyr Asn
                165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
            195                 200                 205

Lys Leu Asn Ala Gln Lys Asn Ala Val Trp Asn Glu Met Met Thr Phe
210                 215                 220

Leu Gly Ile Lys Asn Ala Asn Leu Glu Cys Lys Glu Arg Met Val Thr
225                 230                 235                 240

Asp Glu Val Ser Ser Asn Asp Glu Gln Ile Glu Ser Ser Gly Thr Val
                245                 250                 255

Phe Leu Lys Ser Arg Glu Glu Ala Cys Glu Lys Ile Asn Glu Leu Tyr
            260                 265                 270

Gly Leu Asn Val Lys Val Lys Phe Arg Tyr Asp Ile Val Glu Gln Met
            275                 280                 285

Arg Arg Glu Leu Gln Gln Ile Glu Asn Val Ser Arg Gly Thr Ser Asp
290                 295                 300

Gly Glu Thr Asn Glu His His His His His His
305                 310                 315

<210> SEQ ID NO 43
<211> LENGTH: 315
<212> TYPE: PRT
<213> ORGANISM: Artificial Sequence
<220> FEATURE:
<223> OTHER INFORMATION: C-His6-gp10/C76S/C265S/K234C fusion protein

<400> SEQUENCE: 43

Met Ala Arg Lys Arg Ser Asn Thr Tyr Arg Ser Ile Asn Glu Ile Gln
1               5                   10                  15

Arg Gln Lys Arg Asn Arg Trp Phe Ile His Tyr Leu Asn Tyr Leu Gln
            20                  25                  30

Ser Leu Ala Tyr Gln Leu Phe Glu Trp Glu Asn Leu Pro Pro Thr Ile
            35                  40                  45

Asn Pro Ser Phe Leu Glu Lys Ser Ile His Gln Phe Gly Tyr Val Gly
            50                  55                  60

Phe Tyr Lys Asp Pro Val Ile Ser Tyr Ile Ala Ser Asn Gly Ala Leu
65                  70                  75                  80

Ser Gly Gln Arg Asp Val Tyr Asn Gln Ala Thr Val Phe Arg Ala Ala
                85                  90                  95

Ser Pro Val Tyr Gln Lys Glu Phe Lys Leu Tyr Asn Tyr Arg Asp Met
            100                 105                 110

Lys Glu Glu Asp Met Gly Val Val Ile Tyr Asn Asn Asp Met Ala Phe
            115                 120                 125

Pro Thr Thr Pro Thr Leu Glu Leu Phe Ala Ala Glu Leu Ala Glu Leu
            130                 135                 140
```

```
Lys Glu Ile Ile Ser Val Asn Gln Asn Ala Gln Lys Thr Pro Val Leu
145                 150                 155                 160

Ile Arg Ala Asn Asp Asn Asn Gln Leu Ser Leu Lys Gln Val Tyr Asn
                165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
        195                 200                 205

Lys Leu Asn Ala Gln Lys Asn Ala Val Trp Asn Glu Met Met Thr Phe
210                 215                 220

Leu Gly Ile Lys Asn Ala Asn Leu Glu Cys Lys Glu Arg Met Val Thr
225                 230                 235                 240

Asp Glu Val Ser Ser Asn Asp Glu Gln Ile Glu Ser Ser Gly Thr Val
                245                 250                 255

Phe Leu Lys Ser Arg Glu Glu Ala Ser Glu Lys Ile Asn Glu Leu Tyr
            260                 265                 270

Gly Leu Asn Val Lys Val Lys Phe Arg Tyr Asp Ile Val Glu Gln Met
        275                 280                 285

Arg Arg Glu Leu Gln Gln Ile Glu Asn Val Ser Arg Gly Thr Ser Asp
290                 295                 300

Gly Glu Thr Asn Glu His His His His His
305                 310                 315

<210> SEQ ID NO 44
<211> LENGTH: 304
<212> TYPE: PRT
<213> ORGANISM: Artificial Sequence
<220> FEATURE:
<223> OTHER INFORMATION: Delta1-14/gp10-Strep-II fusion protein

<400> SEQUENCE: 44

Ile Gln Arg Gln Lys Arg Asn Arg Trp Phe Ile His Tyr Leu Asn Tyr
1               5                   10                  15

Leu Gln Ser Leu Ala Tyr Gln Leu Phe Glu Trp Glu Asn Leu Pro Pro
                20                  25                  30

Thr Ile Asn Pro Ser Phe Leu Glu Lys Ser Ile His Gln Phe Gly Tyr
            35                  40                  45

Val Gly Phe Tyr Lys Asp Pro Val Ile Ser Tyr Ile Ala Cys Asn Gly
        50                  55                  60

Ala Leu Ser Gly Gln Arg Asp Val Tyr Asn Gln Ala Thr Val Phe Arg
65                  70                  75                  80

Ala Ala Ser Pro Val Tyr Gln Lys Glu Phe Lys Leu Tyr Asn Tyr Arg
                85                  90                  95

Asp Met Lys Glu Glu Asp Met Gly Val Val Ile Tyr Asn Asn Asp Met
                100                 105                 110

Ala Phe Pro Thr Thr Pro Thr Leu Glu Leu Phe Ala Ala Glu Leu Ala
            115                 120                 125

Glu Leu Lys Glu Ile Ile Ser Val Asn Gln Asn Ala Gln Lys Thr Pro
        130                 135                 140

Val Leu Ile Arg Ala Asn Asp Asn Asn Gln Leu Ser Leu Lys Gln Val
145                 150                 155                 160

Tyr Asn Gln Tyr Glu Gly Asn Ala Pro Val Ile Phe Ala His Glu Ala
                165                 170                 175

Leu Asp Ser Asp Ser Ile Glu Val Phe Lys Thr Asp Ala Pro Tyr Val
            180                 185                 190
```

Val Asp Lys Leu Asn Ala Gln Lys Asn Ala Val Trp Asn Glu Met Met
            195                 200                 205

Thr Phe Leu Gly Ile Lys Asn Ala Asn Leu Glu Lys Lys Glu Arg Met
            210                 215                 220

Val Thr Asp Glu Val Ser Ser Asn Asp Glu Gln Ile Glu Ser Ser Gly
225                 230                 235                 240

Thr Val Phe Leu Lys Ser Arg Glu Glu Ala Cys Glu Lys Ile Asn Glu
            245                 250                 255

Leu Tyr Gly Leu Asn Val Lys Val Phe Arg Tyr Asp Ile Val Glu
            260                 265                 270

Gln Met Arg Arg Glu Leu Gln Gln Ile Glu Asn Val Ser Arg Gly Thr
            275                 280                 285

Ser Asp Gly Glu Thr Asn Glu Trp Ser His Pro Gln Arg Phe Glu Lys
            290                 295                 300

<210> SEQ ID NO 45
<211> LENGTH: 293
<212> TYPE: PRT
<213> ORGANISM: Artificial Sequence
<220> FEATURE:
<223> OTHER INFORMATION: GP10/DELTA285-309-STREP-II fusion protein

<400> SEQUENCE: 45

Met Ala Arg Lys Arg Ser Asn Thr Tyr Arg Ser Ile Asn Glu Ile Gln
1               5                   10                  15

Arg Gln Lys Arg Asn Arg Trp Phe Ile His Tyr Leu Asn Tyr Leu Gln
            20                  25                  30

Ser Leu Ala Tyr Gln Leu Phe Glu Trp Glu Asn Leu Pro Pro Thr Ile
            35                  40                  45

Asn Pro Ser Phe Leu Glu Lys Ser Ile His Gln Phe Gly Tyr Val Gly
50                  55                  60

Phe Tyr Lys Asp Pro Val Ile Ser Tyr Ile Ala Cys Asn Gly Ala Leu
65                  70                  75                  80

Ser Gly Gln Arg Asp Val Tyr Asn Gln Ala Thr Val Phe Arg Ala Ala
            85                  90                  95

Ser Pro Val Tyr Gln Lys Glu Pro Lys Leu Tyr Asn Tyr Arg Asp Met
            100                 105                 110

Lys Glu Glu Asp Met Gly Val Val Ile Tyr Asn Asn Asp Met Ala Phe
            115                 120                 125

Pro Thr Thr Pro Thr Leu Glu Leu Phe Ala Ala Glu Leu Ala Glu Leu
            130                 135                 140

Lys Glu Ile Ile Ser Val Asn Gln Asn Ala Gln Lys Thr Pro Val Leu
145                 150                 155                 160

Ile Arg Ala Asn Asp Asn Asn Gln Leu Ser Leu Lys Gln Val Tyr Asn
            165                 170                 175

Gln Tyr Glu Gly Asn Ala Pro Val Ile Phe Ala His Glu Ala Leu Asp
            180                 185                 190

Ser Asp Ser Ile Glu Val Phe Lys Thr Asp Ala Pro Tyr Val Val Asp
            195                 200                 205

Lys Leu Asn Ala Gln Lys Asn Ala Val Trp Asn Glu Met Met Thr Phe
            210                 215                 220

Leu Gly Ile Lys Asn Ala Asn Leu Glu Lys Lys Glu Arg Met Val Thr
225                 230                 235                 240

Asp Glu Val Ser Ser Asn Asp Glu Gln Ile Glu Ser Ser Gly Thr Val
            245                 250                 255

```
Phe Leu Lys Ser Arg Glu Glu Ala Cys Glu Lys Ile Asn Glu Leu Tyr
            260                 265                 270

Gly Leu Asn Val Lys Val Lys Phe Arg Tyr Asp Ile Trp Ser His Pro
        275                 280                 285

Gln Arg Phe Glu Lys
    290

<210> SEQ ID NO 46
<211> LENGTH: 35
<212> TYPE: DNA
<213> ORGANISM: Artificial Sequence
<220> FEATURE:
<223> OTHER INFORMATION: oligonucleotide

<400> SEQUENCE: 46
ttatagggat agttgtaagc taaagaatac gttac                          35

<210> SEQ ID NO 47
<211> LENGTH: 35
<212> TYPE: DNA
<213> ORGANISM: Artificial Sequence
<220> FEATURE:
<223> OTHER INFORMATION: oligonucleotide

<400> SEQUENCE: 47
gtaacgtatt ctttagctta caactatccc tataa                          35

<210> SEQ ID NO 48
<211> LENGTH: 62
<212> TYPE: DNA
<213> ORGANISM: Artificial Sequence
<220> FEATURE:
<223> OTHER INFORMATION: oligonucleotide

<400> SEQUENCE: 48
taatacgact cactattaga acggcatcaa ggtgaactca agattttgta tgttggggat    60
ta                                                                  62

<210> SEQ ID NO 49
<211> LENGTH: 50
<212> TYPE: PRT
<213> ORGANISM: Artificial Sequence
<220> FEATURE:
<223> OTHER INFORMATION: oligonucleotide

<400> SEQUENCE: 49

Ala Ala Gly Ala Ala Cys Gly Gly Cys Ala Thr Cys Ala Ala Gly Gly
 1               5                  10                  15

Thr Gly Ala Ala Cys Thr Thr Cys Ala Ala Gly Ala Thr Ala Ala Thr
            20                  25                  30

Thr Gly Ala Cys Ala Gly Cys Ala Gly Gly Cys Ala Ala Thr Cys Ala
        35                  40                  45

Ala Cys
    50
```